(12) United States Patent
Tran et al.

(10) Patent No.: US 6,309,532 B1
(45) Date of Patent: *Oct. 30, 2001

(54) METHOD AND APPARATUS FOR CAPACITIVE DEIONIZATION AND ELECTROCHEMICAL PURIFICATION AND REGENERATION OF ELECTRODES

(75) Inventors: Tri D. Tran, Livermore; Joseph C. Farmer, Tracy; Laura Murguia, Manteca, all of CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/289,876

(22) Filed: Apr. 12, 1999

Related U.S. Application Data

(63) Continuation-in-part of application No. 08/737,687, filed on Nov. 15, 1996, now Pat. No. 5,954,937, which is a continuation-in-part of application No. 08/246,692, filed on May 20, 1994, now Pat. No. 5,425,858.

(51) Int. Cl.[7] .............................. B01D 15/08; C02F 1/461
(52) U.S. Cl. ......................... 205/687; 204/267; 204/269; 204/278.5; 204/551; 204/554; 205/688
(58) Field of Search .................................. 204/551, 554, 204/555, 647, 660, 661, 663, 267, 269, 278.5; 360/500; 205/687, 688

(56) References Cited

U.S. PATENT DOCUMENTS

| 2,555,487 | 6/1951 | Haugaard et al. ................... 204/180 |
| 2,741,591 | 4/1956 | Dewey, II et al. .................. 204/180 |
| 2,853,448 | 9/1958 | Heiskell, Jr. ........................ 204/299 |
| 3,324,026 | 6/1967 | Waterman et al. ................... 204/302 |
| 3,450,624 | 6/1969 | Natelson .............................. 204/299 |
| 3,451,918 | 6/1969 | Kolin .................................... 204/299 |
| 3,640,813 | 2/1972 | Nerenberg ............................ 204/299 |
| 3,658,674 | 4/1972 | Benak ............................... 204/180 R |

(List continued on next page.)

OTHER PUBLICATIONS

W. J. Blaedel and J. H. Strohl, "Continuous Quantitative Electrolysis," Analytical Chemistry, vol. 36, No. 7, pp 1245–1251, Jun. 1964.

James L. Hern and John H. Strohl, "Modified Graphites for Chelation and Ion Exchange," Analytical Chemistry, vol. 50, No. 14, pp 1954–1959, Dec. 1978.

(List continued on next page.)

Primary Examiner—Kathryn Gorgos
Assistant Examiner—Michael J Feely

(57) ABSTRACT

An electrically regeneratable electrochemical cell (30) for capacitive deionization and electrochemical purification and regeneration of electrodes includes two end plates (31, 32), one at each end of the cell (30). A new regeneration method is applied to the cell (30) which includes slowing or stopping the purification cycle, electrically desorbing contaminants and removing the desorbed contaminants. The cell (30) further includes a plurality of generally identical double-sided intermediate electrodes (37–43) that are equidistantly separated from each other, between the two end electrodes (35, 36). As the electrolyte enters the cell, it flows through a continuous open serpentine channel (65–71) defined by the electrodes, substantially parallel to the surfaces of the electrodes. By polarizing the cell (30), ions are removed from the electrolyte and are held in the electric double layers formed at the carbon aerogel surfaces of the electrodes. The cell (30) is regenerated electrically to desorb such previously removed ions.

30 Claims, 26 Drawing Sheets

U.S. PATENT DOCUMENTS

| | | | |
|---|---|---|---|
| 3,846,274 | 11/1974 | Gifford | 204/299 |
| 3,847,773 | 11/1974 | Snyder | 204/180 R |
| 4,049,534 | 9/1977 | Posner | 204/299 R |
| 4,057,482 | 11/1977 | Candor | 204/299 R |
| 4,159,235 | 6/1979 | Kammel et al. | 204/272 |
| 4,560,445 | 12/1985 | Hoover et al. | 204/15 |
| 4,743,373 | 5/1988 | Rai et al. | 210/198.3 |
| 5,192,432 | 3/1993 | Andelman | 210/198.2 |
| 5,196,115 | 3/1993 | Andelman | 210/198.2 |
| 5,200,068 | 4/1993 | Andelman | 210/198.2 |
| 5,360,540 | 11/1994 | Andelman | 210/198.2 |
| 5,384,685 | 1/1995 | Tong et al. | 361/503 |
| 5,415,768 | 5/1995 | Andelman | 210/198.2 |
| 5,425,858 | 6/1995 | Farmer | 204/149 |
| 5,538,661 | 7/1996 | Otowa | 204/550 |
| 5,547,581 | 8/1996 | Andelman | 210/656 |
| 5,620,597 | 4/1997 | Andelman | 210/198.2 |
| 5,748,437 | 5/1998 | Andelman | 361/302 |
| 5,779,891 | 7/1998 | Andelman | 210/198.2 |
| 5,954,937 * | 9/1999 | Farmer | 205/687 |

OTHER PUBLICATIONS

Industrial Electrochemistry, published by Chapman and Hal, New York, NY, pp 290–291, Month not available.

Robert F. Antrim et al, "Electrochromatography—A Preliminary Study of the Effect of Applied Potential on a Carbonaceous Chromatographic Column," Analytica Chimica Acta, 164, pp 283–286, Month not available.

M. Mitchell Waldrop, "What You Find When Looking for a Soccer Ball," Research News, p 61, Jan. 12, 1990.

J. C. Farmer et al, "Capacitive deionization of $NH_4ClO_4$ solutions with carbon aerogel electrodes," Journal of Applied Electrochemistry 26 pp 1007–1018, Month not available.

Joseph C. Farmer et al, "Desalination with Carbon Aerogel Electrodes," UCRL–ID–125298 Rev. 1, Dec. 4, 1996, Lawrence Livermore National Laboratory, Livermore, CA 94550.

Joseph C. Farmer et al, Electrosorption of Chromium Ions on Carbon Aerogel Electrodes as a Means of Remediating Ground Water, Energy & Fuels, vol. 11, No. 2, pp 337–347, Month not available.

* cited by examiner

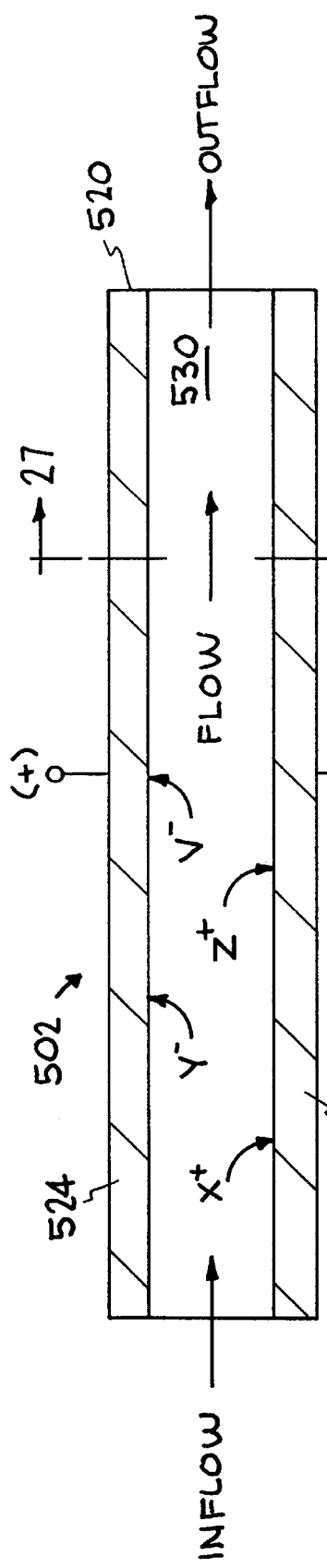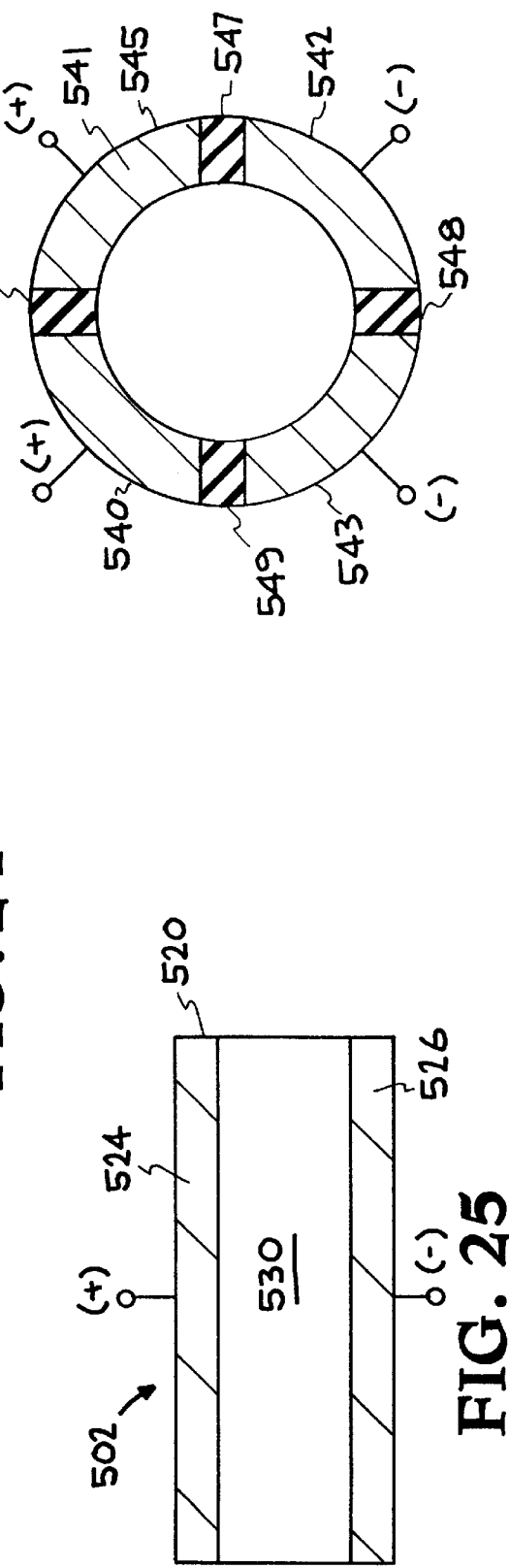
FIG. 24
FIG. 25
FIG. 27

METHOD AND APPARATUS FOR CAPACITIVE DEIONIZATION AND ELECTROCHEMICAL PURIFICATION AND REGENERATION OF ELECTRODES

COPENDING APPLICATIONS

This Application is a continuation-in-part of U.S. patent application Ser. No. 08/737,687, filed Nov. 15, 1996, now U.S. Pat. No. 5,954,937, which is a continuation-in-part application of U.S. patent application Ser. No. 08/246,692, filed May 20, 1994, now U.S. Pat. No. 5,425,858, and titled, METHOD AND APPARATUS FOR CAPACITIVE DEIONIZATION, ELECTROCHEMICAL PURIFICATION, AND REGENERATION OF ELECTRODES. Such applications are incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to an electrochemical separation method and apparatus for removing ions, contaminants and impurities from water, fluids, and other aqueous process streams, and for placing the removed ions back into solution during regeneration.

2. Background Art

The separation of ions and impurities from electrolytes has heretofore been generally achieved using a variety of conventional processes including: ion exchange, reverse osmosis, electrodialysis, electrodeposition, and filtering. Other methods have been proposed and address the problems associated with the conventional separation processes. However, these proposed methods have not been completely satisfactory and have not met with universal commercial success or complete acceptance. One such proposed ion separation method is a process for desalting water based on periodic sorption and desorption of ions on the extensive surface of porous carbon electrodes.

The conventional ion exchange process generates large volumes of corrosive secondary wastes that must be treated for disposal through regeneration processes. Existing regeneration processes are typically carried out following the saturation of columns by ions, by pumping regeneration solutions, such as concentrated acids, bases, or salt solutions through the columns. These routine maintenance measures produce significant secondary wastes, as well as periodic interruptions of the deionization process. Secondary wastes resulting from the regeneration of the ion exchangers typically include used anion and cation exchange resins, as well as contaminated acids, bases and/or salt solutions.

In some instances, the secondary radioactive wastes are extremely hazardous and can cause serious environmental concerns. For instance, during plutonium processing, resins and solutions of $HNO_3$ become contaminated with $PuO_2^{++}$ and other radioisotopes. Given the high and increasing cost of disposal of secondary wastes in mined geological repositories, there is tremendous and still unfulfilled need for reducing, and in certain applications, eliminating the volume of secondary wastes.

Another example is the use of the ion exchange process for industrial purposes, such as in the electroplating and metal finishing industries. A major dilemma currently facing the industry relates to the difficulties, cost considerations and the environmental consequences for disposing of the contaminated rinse solution resulting from the electroplating process. A typical treatment method for the contaminated rinse water is the ion exchange process.

Other exemplary processes which further illustrate the problems associated with ion exchange include residential water softening and the treatment of boiler water for nuclear and fossil-fueled power plants. Such water softeners result in a relatively highly concentrated solution of sodium chloride in the drinking water produced by the system. Therefore, additional desalination devices, such as reverse osmosis filters are needed to remove the excess sodium chloride introduced during regeneration.

Therefore, there is still a significant and growing need for a new method and apparatus for deionization and subsequent regeneration, which significantly reduce, if not entirely eliminate secondary wastes in certain applications. The new method and apparatus should enable the separation of any inorganic or organic ion or dipole from any ionically conducting solvent, which could be water, an organic solvent, or an inorganic solvent. For example, it should be possible to use such a process to purify organic solvents, sudh as propylene carbonate, for use in lithium batteries and other energy storage devices. Furthermore, it should be possible to use such a process to remove organic ions, such as formate or acetate from aqueous streams.

The new method and apparatus should further be adaptable for use in various applications, including without limitation, treatment of boiler water in nuclear and fossil power plants, production of high-purity water for semiconductor processing, removal of toxic and hazardous ions from water for agricultural irrigation, and desalination of sea water.

In the conventional reverse osmosis systems, water is forced through a membrane, which acts as a filter for separating the ions and impurities from electrolytes. Reverse osmosis systems require significant energy to move the water through the membrane. The flux of water through the membrane results in a considerable pressure drop across the membrane. This pressure drop is responsible for most of the energy consumption by the process. The membrane will also degrade with time, requiring the system to be shut down for costly and troublesome maintenance.

Therefore, there is a need for a new method and apparatus for deionization and ion regeneration, which substitute for the reverse osmosis systems, which do not result in a considerable pressure drop, which do not require significant energy expenditure, or interruption of service for replacing the membrane(s).

U.S. Pat. No. 3,883,412 to Jensen describes a method for desalinating water. Another ion separation method relating to a process for desalting water based on periodic sorption and desorption of ions on the extensive surface of porous carbon electrodes is described in the Office of Saline Water Research and Development Progress Report No. 516, March 1970, U.S. Department of the Interior PB 200 056, entitled "The Electrosorb Process for Desalting Water", by Allan M. Johnson et al., ("Department of the Interior Report") and further in an article entitled "Desalting by Means of Porous Carbon Electrodes" by J. Newman et al., in J. Electrochem. Soc.: Electrochemical Technology, March 1971, Pages 510–517, ("Newman Article"). A comparable process is also described in NTIS research and development progress report No. OSW-PR-188, by Danny D. Caudle et al., "Electrochemical Demineralization of Water with Carbon Electrodes", May, 1966.

The Department of the Interior Report and the Newman Article review the results of an investigation of electrosorption phenomena for desalting with activated carbon electrodes, and discuss the theory of potential modulated ion sorption in terms of a capacitance model. This model desalination system 10, illustrated in FIG. 1, includes a stack of alternating anodes and cathodes which are further shown in FIG. 2, and which are formed from beds of carbon powder or particles in contact with electrically conducting screens (or sieves). Each cell 12 includes a plurality of anode screens 14 interleaved with a plurality of cathode screens 16, such that each anode screen 14 is separated from the adjacent cathode screen 16 by first and second beds 18, 20, respectively, of pretreated carbon powder. These two carbon powder beds 18 and 20 are separated by a separator 21, and form the anode and cathode of the cell 12. In operation raw water is flown along the axial direction of the cells 12, perpendicularly to the surface of the electrode screens 14, 16, to be separated by the system 10 into waste 23 and product 25.

However, this model system 10 suffers from several disadvantages, including:

1. The carbon powder beds 18 and 20 are used as electrodes and are not "immobilized".

2. Raw water must flow axially through these electrode screens 14 and 16, beds of carbon powder 18 and 20, and separators 21, which cause significant pressure drop and large energy consumption.

3. The carbon bed electrodes 18 and 20 are quite thick, and a large potential drop is developed across them, which translates into lower removal efficiency and higher energy consumption during operation.

4. Even though the carbon particles "touch", i.e., adjacent particles are in contact with each other, they are not intimately and entirely electrically connected. Therefore, a substantial electrical resistance is developed, and significantly contributes to the process inefficiency. Energy is wasted and the electrode surface area is not utilized effectively.

5. The carbon beds 18 and 20 have a relatively low specific surface area.

6. The carbon powder bed electrodes 18 and 20 degrade rapidly with cycling, thus requiring continuous maintenance and skilled supervision.

7. The model system 10 is designed for one particular application, sea water desalination, and does not seem to be adaptable for other applications.

Numerous supercapacitors based on various porous carbon electrodes, including carbon aerogel electrodes, have been developed for energy storage applications, and are illustrated in the following:

"Double Layer Electric Capacitor", Nippon Electric Co., Japanese Patent application No. 91-303689, 05211111.

"Electric Double-layer Capacitor", Matsushita Electric Industrial Co., Ltd., Japanese Patent application No. 83-89451, 59214215.

Tabuchi, J., Kibi, Y., Saito, T., Ochi, A., "Electrochemical Properties of Activated Carbon/Carbon Composites for Electric Double-layer Capacitor in New Sealed Rechargeable Batteries and Supercapacitors", presented at the 183$^{rd}$ Electrochemical Society meeting, Honolulu, Hawaii, May 16–21, 1993.

"Electrical Double-layer Capacitor, Uses Porous Polarized Electrode Consisting of Carbonized Foamed Phenol Resin", Mitsui Petrochem Ind., Japanese Patent application No. 3,141,629.

Delnick, F. M., Ingersoll, D., Firsich, D., "Double-Layer Capacitance of Carbon Foam Electrodes", SAND-93-2681, Sandia National Laboratory, international seminar report on double layer capacitors and similar energy storage systems, Dec. 6–8, 1993.

Mayer, S. T., Pekala, R. W., Kaschnitter, J. L., "The Aerocapacitor: An Electrochemical Double-layer Energy-Storage Device", J. Electrochemical Society, vol. 140(2) pages 446–451 (February 1993).

U.S. Pat. No. 5,260,855 issued to Kaschmitter et al.

None of these energy storage devices is designed to permit electrolyte flow and most require membranes to physically separate the electrodes. Other electrode materials have been developed for electrolytic cells, e.g. composites of activated carbon powder and an appropriate polymeric binder, as described by Wessling et al., in U.S. Pat. No. 4,806,212. Even though such materials are made from activated carbon powders with very high specific surface areas (600 $m^2$/gm), much of the surface is occluded by the binder.

Therefore, there is still a significant unfulfilled need for a new method and apparatus for deionization and regeneration, which, in addition to the ability to significantly reduce, if not completely eliminate, secondary wastes associated with the regeneration of ion exchange columns, do not result in a considerable pressure drop of the flowing process stream, and do not require significant energy expenditure. Furthermore, each electrode used in this apparatus should be made of a structurally stable, porous, monolithic solid. Such monolithic electrodes should not become readily entrained in, or depleted by the stream of fluid to be processed, and should not degrade rapidly with cycling. These electrodes should have a very high specific surface area; they should be relatively thin, require minimal operation energy, and have a high removal efficiency. The new method and apparatus should be highly efficient, and should be adaptable for use in a variety of applications, including, but not limited to seawater desalination.

It would be highly desirable to provide a new class of electrosorption media that may be less susceptible to poisoning and degradation than carbon-based materials, for use in capacitive deionization and regeneration methods and apparatus.

It is likely that continued direct exposure of the electrosorption medium to the electrolytes and chemical regenerants could further degrade the electrodes. Therefore, there is a need for a new separation process that protects the electrosorption medium from the damaging effect of the electrolytes and chemical regenerants, and which does not require the use of chemical regenerants but only makes such regenerants optional.

Ion exchange chromatography is an analytical method which involves the separation of ions due to the different affinity of the solute ions for the exchanger material. It is a liquid-solid technique in which the ion exchanger represents the solid phase. In ion-exchange separation, the solid phase or column is usually a packed bed of ion exchanger in finely comminuted form; the anion or cation exchanger must be appropriate as the solid phase for the sample of interest. The mobile phase is a solvent such a water with one or more additives such as buffers, neutral salts or organic solvents.

In ion-exchange chromatography the ion-exchanging suppressor column must be periodically regenerated. This is a time-consuming procedure and during the time that the stripper column is being regenerated, the apparatus is not available for use. To minimize the frequency of regeneration, the volume ratios of the suppressor column with respect to the separator column should be kept as low as possible, typically at a ratio of 1:1. This essentially doubles the cost of the ion-exchange materials required.

U.S. Pat. No. 4,672,042 to Ross, Jr. et al., describes an exemplary ion-chromatography system. Two separate exchange columns, anionic and cationic, are required, which increases the cost of the chromatograph, and essentially doubles the cost of the ion exchange or packing material required. Solid ion exchange column packings are used, which limit the applications of the chromatograph and require a significantly higher energy to operate compared to a single hollow column.

Several attempts have been made to select an appropriate ion-exchange composition for the solid phase, e.g. U.S. Pat. No. 5,324,752 to Barretto et al.; U.S. Pat. No. 4,675,385 to Herring; U.S. Pat. No. 5,294,336 to Mizuno et al.; U.S. Pat. No. 4,859,342 to Shirasawa; U.S. Pat. Nos. 4,952,321 and 4,959,153 to Bradshaw et al.

However, these devices and methods are specifically designed for particular applications, and a single chromatograph cannot be used universally in various applications. Additionally, these conventional devices require the use of multiple columns.

Therefore, there is still a significant unfulfilled need for a new and versatile chromatograph and method of operation, which uses a single column for simultaneous anionic and cationic types chromatography. This new chromatograph should control the elution time of the species being analyzed, should have reduced overall cost of manufacture, operation and maintenance, should use electrical and/or chemical regeneration and should use the same column (or stack of cells) for both anions and cations.

SUMMARY OF THE INVENTION

In one embodiment, the separation process or apparatus is used for the deionization of water and the treatment of aqueous wastes, referred to as capacitive deionization (CDI). Unlike conventional ion exchange processes, no chemicals, whether acids, bases, or salt solutions, are required for the regeneration of the system; instead, electricity is used. However, in the present invention, regeneration of the separation process or system allows for special chemical treatment combined with the electrical regeneration.

A stream of electrolyte to be processed, which contains various anions and cations, electric dipoles, and/or suspended particles, is passed during a deionization (i.e., purification) cycle through a stack of electrochemical capacitive deionization cells, i.e., a battery of connected, spaced apart, anode/cathode pairs, each of the pairs operable as an electrochemical cell. (As referred to herein, a cell can include one or more single anode/cathode pairs capable of operating as a battery of cells). Each of these cells includes carbon aerogel electrodes having exceptionally high specific surface areas (for example, 400–1000 $m^2$/gm). By polarizing the cell, non-reducible and non-oxidizable ions are removed from the fluid stream electrostatically and held in the electric double layers formed at the surfaces of the electrodes. Some metal cations are removed by electrodeposition. Electric dipoles also migrate to and are trapped at the electrodes. Small, suspended particles are removed by electrophoresis. Therefore, the fluid stream leaving the cell is purified.

As the electrodes become saturated, the rate of fluid flow through the cell is slowed or stopped during a regeneration cycle and the electrodes shorted or reversed polarized. The system is held under such regeneration conditions for a time sufficient to desorb a desired portion of the previously adsorbed and/or absorbed electrolytes (e.g., ions) from the electrodes. The desorbed portion of waste electrolytes is flushed out of each cell with "regenerant" solution (e.g., influent waste fluid, deionized water, reused regenerant solution, and the like) at a rate typically above the rate of electrostatic removal during the purification cycle. Relatively few of these "fast" flushing cycles are required for desired levels of regeneration of the electrodes. Under such "slow flow or stopped flow" conditions, the saturated or partially saturated electrodes may be exposed to a mild oxidizing agent, such as hydrogen peroxide, to remove adsorbed organics, bacteria, microbes, etc., and other contaminants, which can also be fast flushed.

In the present CDI process, energy is expended using electrostatics to remove salt and other impurities from the fluid, and, as a result, is more efficient, usually at least three times more efficient and can be orders-of-magnitude more energy efficient than conventional processes such as reverse osmosis. Furthermore, the pressure drop in the capacitive deionization cells is dictated by channel flow between parallel surfaces of monolithic, microporous solids (i.e., the electrodes); hence, it is insignificant compared to that needed to force water through the permeable membrane required by the reverse osmosis process.

One feature of the CDI separation system is that no expensive ion exchange membranes are required for the separation of the electrodes. All the anodes and cathodes of the electrode pairs can be connected either fluidically and/or electrically in series or parallel. The system is modular, and the system capacity can be increased to any desired level by expanding the cell(s) to include a greater number of electrode pairs.

Some advantages of the present invention include, but are not limited to the following:

1. Unlike conventional processes where water is forced through a membrane by pressure gradient, or where fluid is flown through a packed bed, the CDI separation methods and systems do not require the electrolyte to flow through any porous media such as membranes or packed beds. In the present system, electrolyte flows in open channels formed between two adjacent, planar electrodes, which are geometrically parallel. Consequently, the pressure drop is much lower than conventional processes. The fluid flow can be gravity fed through these open channels, or a pump can be used.

2. The CDI system does not require membranes, which are both troublesome and expensive, which rupture if overpressured, which add to the internal resistance of the capacitive cell, and which further reduce the system energy efficiency.

3. The electrodes in the CDI system are composed of immobilized sorption media, such as monolithic carbon aerogel, which is not subject to entrainment in the flowing fluid stream. Thus, material degradation due to entrainment and erosion is considerably less than in conventional packed carbon columns.

4. The present systems and methods are inherently and greatly energy efficient. For instance, in both evaporation and reverse osmosis processes, water is removed from salt, while in the present systems, salt is removed from water, thus expending less energy.

5. The present systems and methods present superior potential distribution in the thin sheets of carbon aerogel;

most of the carbon aerogel is maintained at a potential where electrosorption is very efficient.

6. The present systems and methods allow for more effective regeneration of the electrodes. The electrosorption capacity of the electrodes can be increased by effective use of static (i.e., stopped flow) conditions or slow flow (i.e., slower than the flow rate of the purification cycle) conditions at short circuit or optionally reverse polarization conditions. Either influent waste stream (such as raw fluid), deionized water, or other regenerant solutions, preferably having a lower ionic concentration than the influent raw fluid, can be employed for flushing out the desorbed contaminants at such conditions. (Regenerant solutions having a higher ionic concentration than the influent raw fluid can also be employed with success.)

7. The present regeneration systems and methods take advantage of convenient activation and/or reactivation of the electrodes with chemical regenerants such as dilute oxidants. Such chemical regenerants can be effective at static or slow flow conditions at either short circuit or reversed polarity conditions.

The above and further features and advantages of the present invention are realized by a new electrically regeneratable electrochemical cell for capacitive deionization and electrochemical purification and regeneration of electrodes. The cell components can be corrosion resistant and include two end plates, one at each end of the cell, as well as two end electrodes that are arranged one at each end of the cell, adjacent to the end plates. An insulator layer is interposed between each end plate and the adjacent end electrode.

Each end electrode includes an electrosorption medium having a high specific surface area and sorption capacity. In the preferred embodiment, the electrosorption medium is formed of carbon aerogel composite. The cell, i.e., battery of cells, further includes one or more intermediate electrodes that are disposed between the two end electrodes. As the electrolyte enters the cell, it flows through a continuous open serpentine channel defined by the electrodes, substantially parallel to the surfaces of the electrodes. The majority (preferably a plurality) of the intermediate electrodes are located within the cell such that neither end of the open channel defined therebetween opens to the exterior of the cell or battery, but opens to either a subsequent or prior open channel defined by the electrodes. By polarizing the cell, ions are removed from the electrolyte and are held in the electric double layers formed at the carbon aerogel surfaces of the electrodes. As the cell is saturated with the removed ions, the cell is regenerated electrically and/or chemically, thus significantly minimizing secondary wastes. The minimizing of wastes is substantially improved with the stopped or slow flow regeneration method compared to a method wherein the flow through the cell(s) is continuous during regeneration.

BRIEF DESCRIPTION OF THE DRAWINGS

FIG. 24 is a longitudinal cross sectional view of a cell used in the chromatograph of FIG. 23.

FIG. 25 is a lateral cross sectional view of a first embodiment of the cell of FIG. 24, taken along line 25—25.

FIG. 27 is a lateral cross sectional view of a second embodiment of the cell of FIG. 24, taken along line 25—25.

DETAILED DESCRIPTION OF THE PREFERRED EMBODIMENTS

Figure 3:
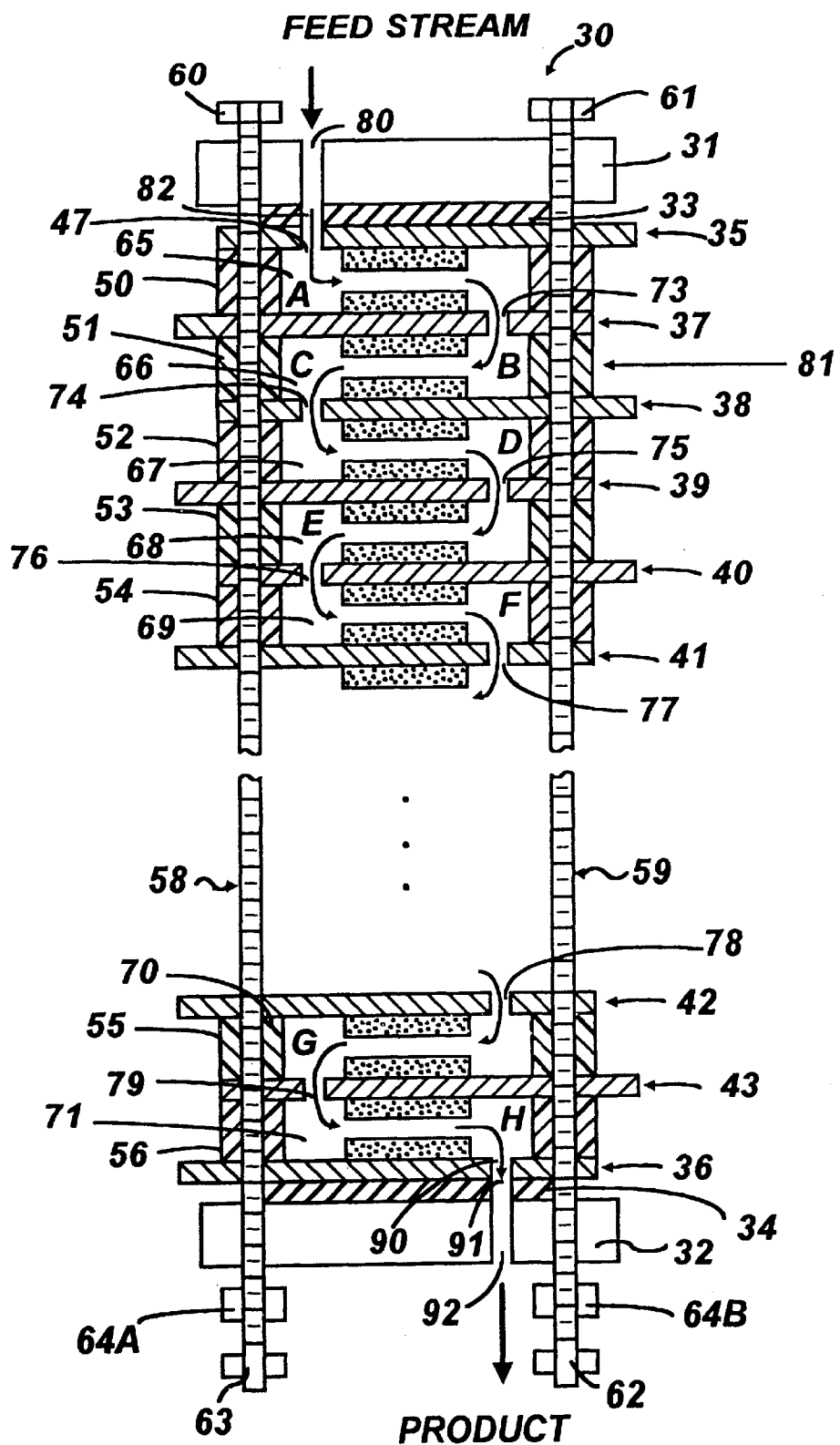
FIG. 3 is a schematic, sectional, elevational view of an electrochemical cell.

FIG. 3 illustrates a battery of cells shown as an electrochemical cell 30 which generally includes two oppositely disposed, spaced-apart end plates 31 and 32, one at each end of the cell 30, and two generally identical single-sided end electrodes 35, 36, one at each end of the cell 30, adjacent to the end plates 31 and 32, respectively. An insulator layer 33 is interposed between the end plate 31 and the end electrode 35. Similarly, an insulator layer 34 is interposed between the end plate 32 and the end electrode 36. Each single-sided electrode 35, 36 includes a single sheet of carbon aerogel composite bonded to one side of a titanium or functionally equivalent metal-containing sheet with a conductive epoxy or other appropriate bonding material.

A plurality of generally identical double-sided intermediate electrodes 37–43 are spaced-apart and equidistally separated from each other, between the two end electrodes 35, 36. Each double-sided electrode, i.e., 37, includes two sheets of carbon aerogel composite bonded to both sides of a titanium sheet with conductive epoxy. While FIG. 3 illustrates only seven double-sided intermediate electrodes 37–43, a different number of intermediate electrodes can alternatively be used. For instance, the capacity of the cell 30 can accommodate at least 192 intermediate electrodes, such that the total anode (or cathode) surface area can, in this case, be approximately $2.7 \times 10^8$ cm$^2$. Ultimately, the system could be expanded to include an unlimited number of electrode pairs having an unlimited active area for accumulation of ionic species.

The end electrodes 35, 36 and the intermediate electrodes 37–43 are generally similar in design, construction and composition, but each intermediate electrode has two sheets of carbon aerogel composite bonded to both sides of a titanium sheet with conductive epoxy, whereas each end electrode has only one sheet of carbon aerogel composite bonded to one side of a titanium sheet with conductive epoxy. Other porous conductive, monolithic materials can be used for the carbon aerogel composite.

Figure 4A:
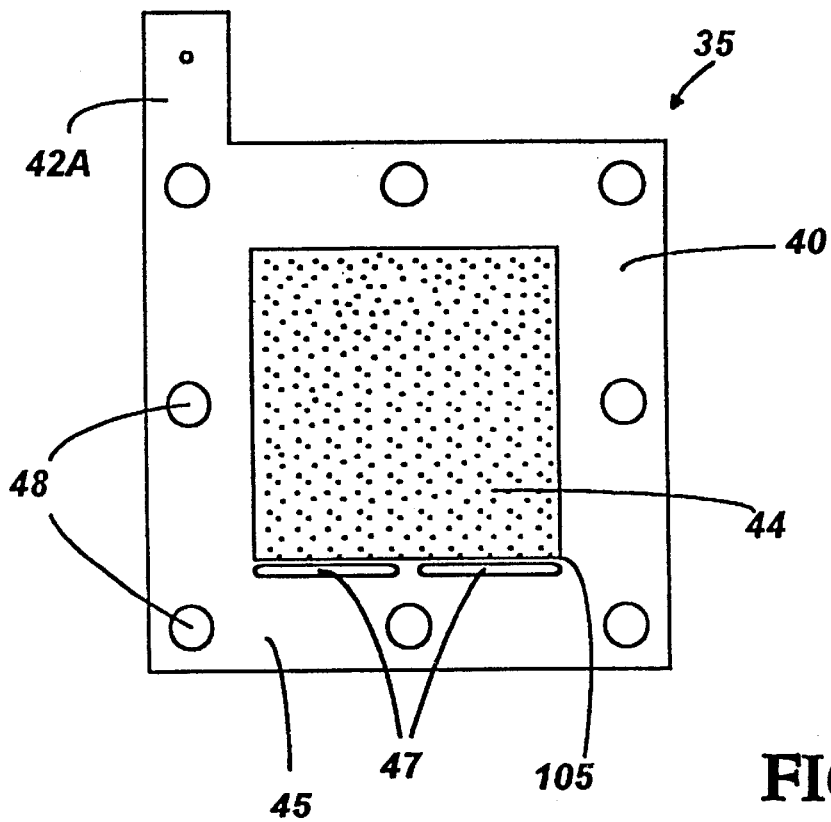
FIG. 4A is a greatly enlarged top plan view of a capacitive electrode, adapted for use in the electrochemical cell of FIG. 3.

FIG. 4A shows end electrode 35, which includes a generally flat, thin rectangularly shaped, corrosion resistant (e.g., capable of withstanding the deleterious effects of oxidants employed during regeneration), metallic (e.g., titanium) sheet, structural support 40. A tab 42A extends integrally from one side of the structural support 40, for connection to the appropriate pole of a D.C. power source (not shown). A thin sheet 44 of high specific area, porous, conductive, monolithic material (i.e., carbon aerogel composite) is bonded to the surface of the structural support 40, and can be either a cathode or an anode. The structural support 40 further includes a series of generally identical apertures 47 for providing a passage to the electrolyte, through the end electrode 35.

Preferably, the thin layer of high specific area material 44 is composed of a composite material formed by impregnating a carbon cloth with carbon aerogel, wherefore, the thin layer 44 will also be referred to as carbon aerogel composite electrode 44. The new use of this carbon aerogel composite electrode 44 relies primarily on the unique open-cell nanostructure of the carbon aerogel material, including its interconnected porosity, ultrafine pore sizes and huge surface area. This carbon aerogel composite material is described in more detail in an article entitled "Carbon Aerogel Composite Electrodes", by Joseph Wang et al., in Anal. Chem. 1993, vol. 65, pages 2300–2303, and in U.S. Pat. No. 5,260,855 by James L. Kaschmitter et al. entitled "Supercapacitors Based on Carbon Foams". Another method of producing a porous carbon foam is described in U.S. Pat. No. 5,358,802 to Mayer et al.

Carbon aerogels are synthesized by the polycondensation of resorcinol and formaldehyde (in a slightly basic medium), followed by supercritical drying and pyrolysis (in an inert atmosphere). This fabrication process results in unique open-cell carbon foams that have high porosity, high surface area (400–1000 m$^2$/g), ultrafine cell/pore sizes (less than 50 nm), and a solid matrix composed of interconnected colloidal-like particles or fibrous chains with characteristic diameters of 10 nm. The porosity and surface area of aerogels can be controlled over a broad range, while the pore size and particle size can be tailored at the nanometer scale. The carbon aerogels further offer both low density and ultrasmall cell size.

The use of the carbon aerogel composite electrode 44 presents a significant improvement over conventional devices, since in these latter devices only part of the specific area is effective for removing ions, and the remaining area is not effective because of the potential gradients across the electrodes. By using thin sheets of carbon aerogel composite as electrodes 44, substantially the entire surface area of these monolithic microporous electrodes is effective in the removal of ions, due to the desirable potential distribution in the aerogel. Furthermore, such electrodes are corrosion resistant.

While the best mode of the present invention utilizes thin sheets of carbon aerogel composite as electrodes, beds of carbon aerogel particles can alternatively be used to form electrodes. Such beds of carbon aerogel particles have much higher specific area and sorption capacity than beds of conventional carbon powder, and therefore they are superior electrodes for capacitive deionization.

In FIG. 3, the end electrodes 35, 36 and the adjacent intermediate electrodes 37–43 are separated by means of thin sheets of insulating material, such as rubber gaskets 50–56. Each gasket has a large, square aperture in the center to accommodate adjacent carbon aerogel composite electrodes 44. As shown in FIGS. 4A,B the structural support 40 includes a plurality of peripheral holes 48. When the cell 30 is to be assembled, the peripheral holes 48 are coaligned with corresponding peripheral holes in the insulation layers 33, 34 and the rubber gaskets 50–56, and a plurality of threaded rods 58, 59 are inserted through these coaligned holes, and are tightened by conventional means, such as nuts 60–63. Non-compressible, insulating, hollow, cylindrical spacers or compression rings 50A can be inserted in the peripheral holes of the rubber gaskets 50–56, and used to control the spacing of adjacent electrodes. A plurality of compression sleeves 64A, 64B can be added to provide additional force for sealing. Although the use of rubber gaskets is suitable, functionally equivalent sealing and/or spacing materials are also employed, particularly those materials that are corrosion resistant.

Figure 4B:
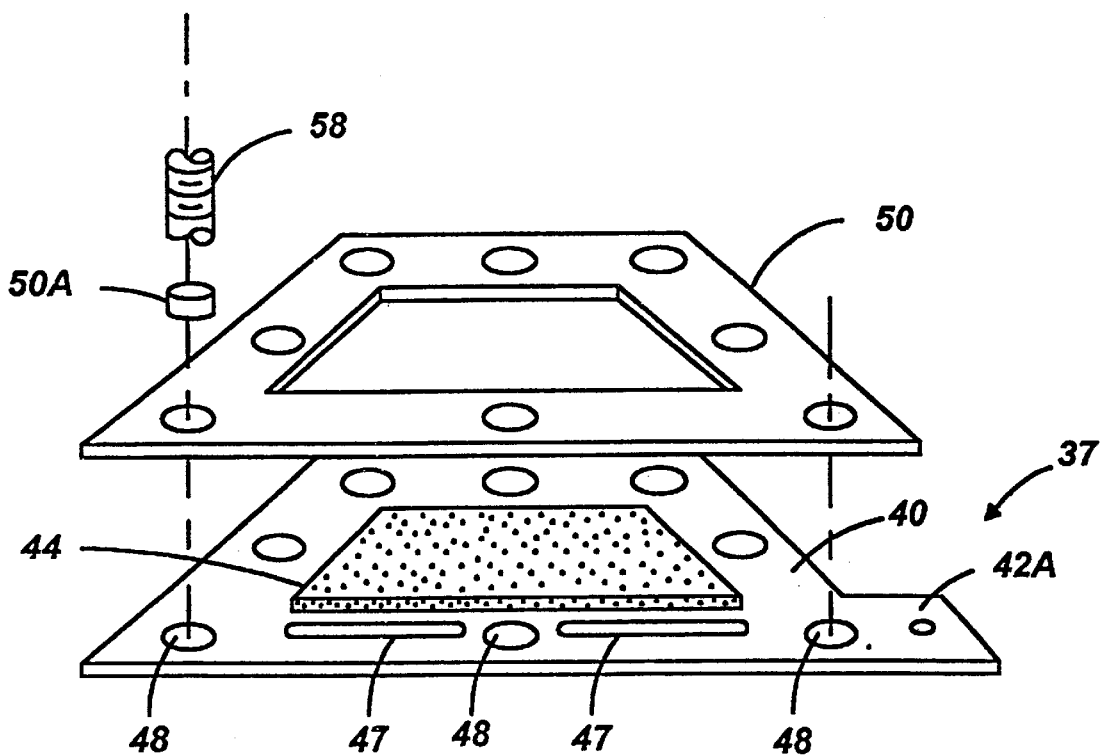
FIG. 4B is a greatly enlarged exploded view of a rubber gasket used in conjunction with the capacitive electrode of FIG. 4A.

While only two threaded rods 58, 59 are shown in FIG. 3, in this particular example, eight threaded rods are used to tighten the cell 30 to a leak proof state. These eight rods are designed to fit through the eight peripheral holes 48 in the structural support 40, as well as through the corresponding peripheral holes in the rubber gaskets 50–56 fitted with hollow-cylindrical spacers 50A (FIG. 4B).

Once the cell 30 is assembled, a plurality of chambers 65–71 are formed between the end and intermediate electrodes 35–43. These chambers 65–71 are adapted to fluidly communicate with each other via a plurality of apertures 73–79 in the structural supports of the intermediate electrodes 37–43, respectively. These apertures 73–79 are not coaligned, and may be either holes or slits. They are positioned so that the fluid path therethrough, within the chambers 65–71, is forced to flow across all the exposed surfaces of the carbon aerogel composite electrodes 44. In FIG. 3, the fluid first flows from left-to-right, then from right-to-left, and so on.

In operation, and merely for illustration purposes, the anodes and the cathodes of the cell 30 are interleaved in an alternating way. In this respect, every other electrode is an anode, starting with the end electrode 35, and ending with the intermediate electrode 43, and the remaining intermediate electrodes 37, 39, 41, 42 and the end electrode 36 are cathodes. As such, each pair of adjacent electrodes (anode and cathode) forms a separate capacitive deionization/regeneration unit.

The stream of raw fluid or electrolyte to be processed enters the cell 30 through a plurality of superposed, coaxially registered, generally circularly or rectangularly shaped openings, including an aperture 80 in the end plate 31, one or more apertures 82 in the insulation layer 33, and the apertures 47 in the end electrode 35. The fluid flows through the first chamber 65 as indicated by the arrow A, is substantially parallel to the electrode surface. By polarizing the first deionization/regeneration unit, ions are removed from the fluid stream electrostatically, and are held in the electric double layers formed at the carbon aerogel surfaces of the electrodes 35 and 37. This will purify the fluid stream, at least partially.

The fluid stream then flows through the aperture 73 into the next chamber as indicated by the arrow B, where additional ions are removed by the polarization of the second deionization/regeneration unit 81 formed by the intermediate electrodes 37 and 38, thus further purifying the fluid stream. The fluid stream continues to travel through the remaining deionization-regeneration units, indicated by the arrows C through G, and is progressively purified. Thereafter, as indicated by the arrow H, the purified fluid stream exits the cell 30 via a plurality of coaxially aligned apertures 90, 91, 92 in the end electrode 36, insulator layer 34, and the back plate 32, respectively.

The fluid stream leaving the cell 30 is purified since the contamination ions have been removed and collected by the cell 30. One important characteristic of the novel configuration of the cell 30 is that the fluid stream does not flow through the porous electrodes, but rather in an open channel, with a relatively low pressure drop (e.g., less than 10 psig), and with minimal energy consumption for pumping. The energy expended to operate the cell 30 is minimal. In this respect, the fluid stream does not necessarily need to be pressurized by a pump to cause it to flow through the cell 30; gravity can be used, if desired.

Also, if the inventive deionization process was used for water desalination, the energy expended is that which is necessary to remove salt from water, whereas in conventional desalting processes, such as evaporation and reverse osmosis, the energy is expended to remove the water from salt. As a result, the present process can be orders-of-magnitude more energy efficient than conventional processes.

Additionally, the pressure drop in the capacitive deionization cell 30 is insignificant compared to that needed for reverse osmosis. Also, contrary to conventional deionization processes, the electrodes have a very high and immobilized specific surface area and a high removal efficiency, and the carbon aerogel particles are not entrained by the fluid stream.

As the CDI cell 30 is saturated with the removed ions, the capacitive units become fully charged, and a sensor (not shown) indicates that such condition has been reached, and that the cell 30 is ready for regeneration. Contrary to conventional chemical regeneration processes, the present regeneration process is carried out electrically, thus eliminating the secondary wastes. The regeneration process takes place by disconnecting the power supply, by interconnecting the anodes and the cathodes, by electrically discharging all electrodes 35–43 (i.e., "shorting" the cell), and by flowing a suitable fluid stream of water or another suitable solution through the cell 30, along the same path described above in connection with the deionized stream of raw fluid. As a result, the capacitive units are discharged through, and release the previously removed ions into the flowing fluid stream, until the cell 30 is fully regenerated, at which time, the regeneration process is stopped and the deionization process restarts. The timing control of the deionization-regeneration process may be manual or automated.

In a preferred embodiment during regeneration of the cell, the suitable stream of water or another suitable solution is "fast flushed" through the cell to remove desorbed species (e.g., previously removed ions) from the electrodes. Fast flushing during the regeneration cycle involves flowing such a stream through the cell (30) at a faster rate than the fluid flow rate during the purification. An increased fast flush regeneration flow rate is usually greater than about 2 times, and preferably greater than 4 times as fast as the rate of the purification cycle.

A crucial aspect of the regeneration process occurs subsequent to purification and prior to fast flushing. When the power supply is disconnected from the cell and optionally the cell shorted or even the electrode polarity reversed, the flow through the cell is stopped more than momentarily, and preferably for a period of time sufficient to allow at least a portion of the previously accumulated species on the electrodes to be released into the solution from the electrode surfaces. The "stopped flow" time interval can be very short in duration, such as at least or greater than 5 seconds for at least 5 minutes, for at least 15 minutes, or may be relatively long, such as 30 minutes, or an hour or more, depending on the desired amount of regenerated species. Of course, the regeneration cycle does not need to completely stop the flow of fluid through the cell, i.e., can undergo a "slow flow" mode wherein the above regeneration is initiated by simply reducing the rate of fluid flow from that during the purification cycle. Typically, the slow flow mode is conducted at less than 90%, and preferably less than 50% of the purification cycle fluid flow rate.

The overall shape and dimensions of the cell 30 are determined by the mode of use and application of the CDI systems. In a preferred embodiment, the end plates 31 and 32 are identical, rectangularly shaped, and made of 316 stainless steel or another appropriate corrosion resistant alloy. The end plates, unlike the electrodes, are not polarized. However, other shapes can be used; e.g., if the cell 30 were cylindrically shaped, the end plates 31 and 32 are circular, or if the cell 30 were conically shaped, one of the end plates 31, 32 can have a smaller size than the other plate, and the size of the electrodes therebetween gradually increases from one end plate to the other.

The insulator layers 33 and 34, as well as 50–56 are preferably made of an elastic, compressible, insulating, non-leachable material, that is preferably corrosion resistant. For example, Teflon, Viton, Neoprene and similar materials are suitable materials for specific applications.

However, other suitable materials can be used. The structural supports 40 (FIGS. 4A, 4B) of the end electrodes 35, 36 and the intermediate electrodes 37–43 are preferably made of titanium, or, alternatively they can be selected from a suitable group of materials such as coated, corrosion-resistant, iron-chromium-nickel based alloys. Suitable coatings include gold, platinum, iridium, platinum-iridium alloys, Fe—Cr—Ni—Mo alloys such as C276 (UNS), C4 (UNS), C22 (UNS 00622), tungsten-stabilized alloys, or other corrosion resistant materials such as ceramics. Ceramics which can be utilized to coat metallic electrodes or serve as the electrodes, include $TiO_2$, $Al_2O_3$, $SiO_2$, $ZrO_2$, yterium-stabilized $ZrO_2$, and other ceramic oxides, and combinations thereof. Particularly effective ceramics are prepared by a high velocity oxyfuel process producing non-porous (less than about 2% porosity), dense coatings or substrates for the electrodes. Other ceramics can be prepared by plasma spraying processes (18–20% porosities) and reactive ion sputtering.

In one example, the back plates are similarly sized and rectangularly shaped, and have the following dimensions: length 8.38 (20) cm; width 7.87 (10) cm; and thickness 0.16 cm. However, other dimensions can alternatively be used. The tab 42A, used to make electrical connection with the electrode, extends integrally from the structural support 40, and is generally, but not necessarily rectangularly shaped. In the above example, the tab 42A has the following dimensions: length 1.78 cm; width 2.03 cm; and thickness 0.16 cm.

As shown in FIGS. 4A and 4B, the structural support 40 includes a plurality of (in this example eight) peripheral holes 48 through which the threaded rods 58, 59 pass, for aligning the electrodes 35–43. Several elongated apertures 47 are shown co-aligned outside, along, and adjacent to one side 105 of the sheets of aerogel carbon composite 44. These apertures 47 are sized so as to distribute the flow uniformly across the sheet of carbon aerogel composite with minimal pressure drop (usually less than 20 psi for a multicell battery). The number, position and size of these apertures 47 can vary with the desired mode of use and application of the cell 30.

The carbon aerogel composite electrode 44 is shown as having a square shape, and as being centrally positioned relative to the structural support 40. In the present example, the carbon aerogel composite electrode 44 has a side dimension of 6.86 cm, a projected area of approximately 25 $cm^2$, and a thickness of about 0.0127 cm. The electrode 44 can also be circular, rectangular, or triangular.

While the electrode 44 is preferably made of carbon aerogel composite, any monolithic, porous solid that has sufficient electrical conductivity and corrosion resistance (chemical stability) to function as an electrode, can alternatively be used. Such alternative materials include porous carbon electrodes typically used in fuel cells, reticulated vitreous carbon foams, porous metallic electrodes made by powder metallurgy, packed columns of powder (i.e., packed beds of carbon powder, tungsten carbide powder, various conductive oxides including tin oxide and iridium oxide), a mixture of these and other materials, electrolcatalysts such as Pt, Ir, $SnO_2$, or porous electrodes, that are made by microfabrication techniques, including photolithography, electroforming, physical vapor deposition (evaporation, sputtering, etc.) and etching, and conductive sponges of any type.

The electrode 44 could also be fabricated as a packed bed of carbon aerogel particles, having significantly higher specific surface area than the conventional packed carbon bed described in the Department of Interior Report and the Newman Article. This design offers the advantage of greatly enhanced capacity for electrosorption of ions, adsorption of organics, and capture of fine particles, but would require flow through porous media.

Although any volume of raw fluid can be purified and regenerated and the apparati fabricated accordingly such as large volumes in commercial applications, in the specific example illustrated in FIG. 3, the chambers 65–71 have a volume of about 300 ml, which corresponds to the minimum possible liquid volume required for regeneration in this specific case. In other embodiments, the chambers 65–71 can have different volumes, such that the minimum possible liquid required for regeneration can be further reduced.

Figure 5:
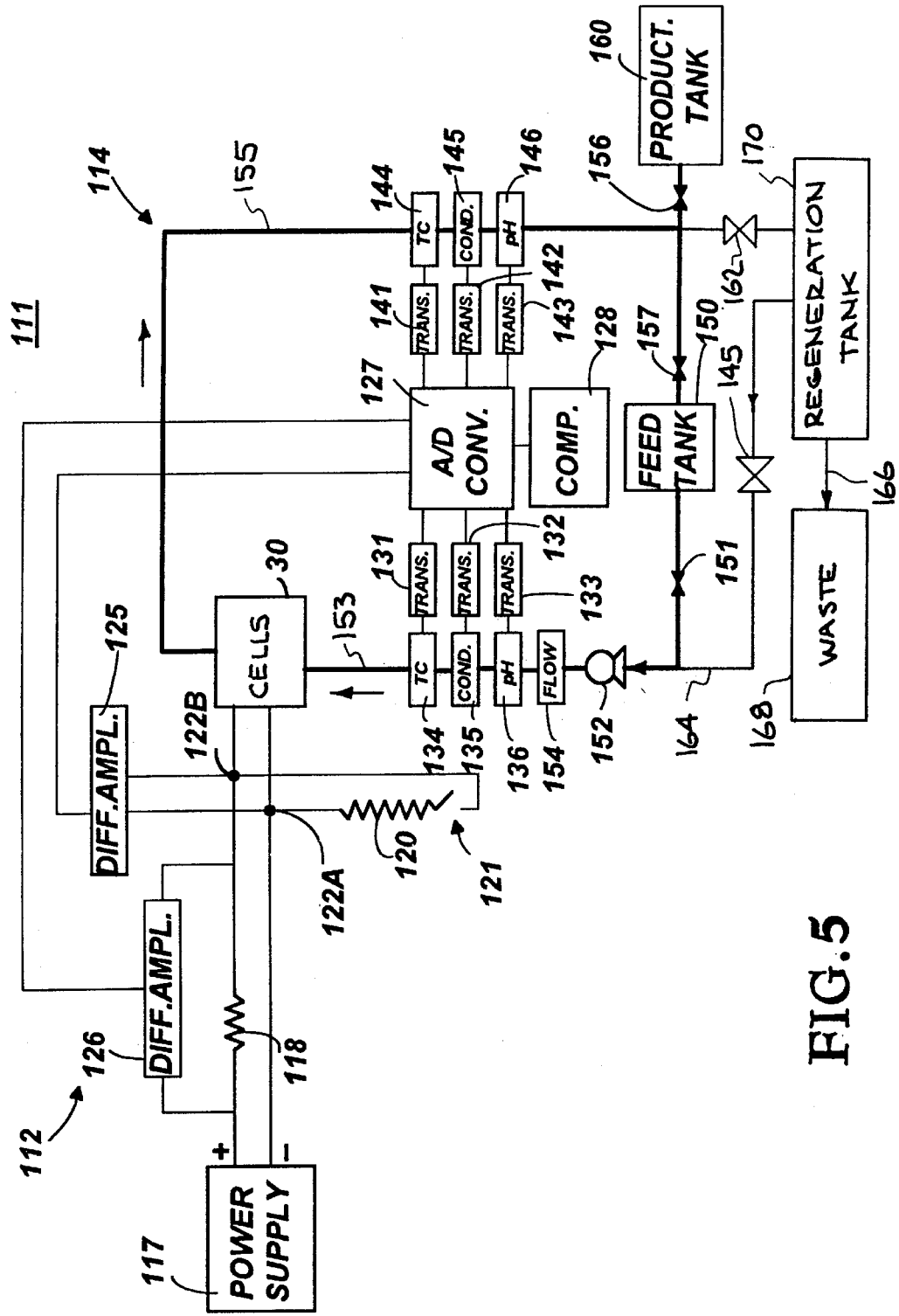
FIG. 5 is a block diagram of a first embodiment of a capacitive deionization-regeneration system using one or a battery of electrochemical cell(s) shown in FIG. 3.

FIG. 5 illustrates a first embodiment of a capacitive deionization-regeneration system 111 which generally includes one or a stack of sequential (i.e., serial) electrochemical cell 30 (FIG. 3), an electrical circuit 112, and a fluid circuit 114, such that the fluid circuit 114 regulates the flow of the fluid stream through the cell 30, under the control of the electrical circuit 112. Although reference to cell 30 is used for illustration herein, cell 30 can also be multiple anode/cathode pairs considered herein as a battery of cells.

Electrical circuit 112 includes a voltage controlled programmable D.C. power supply 117 which provides a constant D.C. voltage across the adjacent pairs of electrodes 35–43 (FIG. 3). A resistive load 120 and a switch 121 are connected in parallel, across the positive and negative terminals 122A, 122B, respectively, of the power supply 117, and are used to discharge, or regenerate the electrochemical cell 30.

The electrical circuit 112 further includes a control system, as a triggering device to initiate regeneration. This control system utilizes on-line conductivity cells, ion selective electrodes, pH electrodes, polarographic sensors, impedance sensors, optical transmission cells, light scattering sensors, chromatographs, mass spectrometers, and/or nuclear radiation detectors. The components that can be triggered by this on-line control system include power supplies, valves and pumps.

A differential amplifier 126 is connected across a shunt resistor 118, and is further connected to an analog-to-digital converter 127 and a computer 128. The shunt resistor 118 is used to measure the current flowing from the power supply 117 to the cell 30, for monitoring and control. Differential amplifier 126 can monitor the transient current flowing through shunt resistor 118. Integration of the transient current by computer 128 enables accurate control of the deionization/regeneration cycles. The differential amplifier 126 amplifies the voltage across the shunt resistor 118 to a level that is monitorable by the analog-to-digital converter 127 and the computer 128 (e.g., digital computer). Although not shown, computer 128 is connected to control the power supply 117. Another differential amplifier 125 is connected across the terminals 122A, 122B of the power supply 117, via the shunt resistor 118, and operates as a buffer between the power supply 117 and the analog-to-digital converter 127, for protecting the analog-to-digital converter 127.

The differential amplifier 125 is connected across the terminals of the cell 30, is used to monitor the voltage across the terminals, and serves as a buffer between the cell 30 and the A/D converter 127. In operation, as the cell 30 is used to deionize the electrolyte, the switch 121 is open. Purification can be accomplished by electrodeposition, electrophoretic deposition, electrochemically-driven chemisorption, double-layer charging, or any other suitable physiochemical mechanism. In order to start the regeneration process, the power supply 117 is turned off, reduced, or disconnected, and the switch 121 is closed, for providing a path for the discharge current. One or more additional differential amplifiers (not shown) monitor the transient current flow through resistor 120 during discharge. Switch 121 can be activated by computer 128 via appropriate relay circuitry (not shown). Resistor 120 can also be an external load, such as another storage battery, electronics, or electrical machinery. Thus, any electrochemical energy stored in cell 30 can be reclaimed during the regeneration or discharge portion of a deionization/regeneration cycle.

The analog-to-digital converter 127 is connected to the inlet stream of the fluid circuit 114, via a plurality of sensors, such as a thermocouple 134, a conductivity probe 135, and a pH sensor 136, via respective transducers 131, 132, 133. The thermocouple 134 enables the monitoring of the temperature of the inlet stream, in order to prevent the overheating of the electrolyte, and further enables the calibration of the conductivity probe 135. Conductivity probe 135 is an on line sensor which monitors the conductivity of the inlet stream. The pH sensor measures the pH level of the inlet stream. The transducers 131, 132, 133 convert the measurements of the thermocouple 134, conductivity probe 135 and pH sensor 136 into voltages that are readable by and compatible with the analog-to-digital converter 127. A flow rate meter 154 measures the flow rate of the inlet stream.

The fluid circuit 114 includes a feed and recycle tank 150 which contains the raw fluid to be processed by the cell 30. The fluid stored in the feed and recycle tank 150 can be replaced with a continuous inflow of raw fluid. A valve 151 is fluidly connected between the feed and recycle tank 150 and a pump 152. The speed of the pump 152 is used to control the flow rate of an inlet stream 153 to the cell 30. An outlet stream 155 is respectively connected, via two valves 156, 157, to a product tank 160 for storing the purified fluid, and to the feed and recycle tank 150. Valves 156 and 157 are used to select the mode of operation: batch mode or complete recycle; continuous mode or once through. Although not shown, cell 30 can include more than one inlet and outlet streams.

Similarly to the inlet stream 153, the analog-to-digital converter 127 is also connected to the outlet stream 155 of fluid circuit 114, via three transducers 141, 142, 143, a thermocouple 144, a conductivity probe 145, and a pH sensor 146.

In the continuous mode of operation, the raw fluid or electrolyte to be deionized is initially stored in the feed and recycle tank 150, and the valve 157 is closed. The pump 152 is activated for pumping the fluid from the feed and recycle tank 150 through an open valve 151 to the cell 30 via inlet stream 153, where the fluid stream is deionized and purified. The purified effluent is then routed through outlet stream 155 to the product tank 160 via the open valve 156. In certain applications, it would be desirable to recycle the fluid stream more than once, in order to obtain the desired level of purification, in which case, the valve 156 is closed, and the valve 157 is opened, in order to allow the fluid stream to be recycled through the cell 30.

The purified feed solution in outlet stream 155 leaves cell 30, passing through temperature sensor 144, electrical conductivity sensor 145 and pH sensor 146, until a targeted breakthrough is detected by the sensors. If the solution being purified is an ionizable salt, it is preferred to detect breakthrough with a combination of electrical conductivity and pH sensors. However, if the contaminant is a heavy metal, radioisotope, or organic material, different sensors may be used in conjunction with, or in lieu of electrical conductivity and pH sensors. For example, dissolved heavy metals can be detected with spectrophotometry, polarography, cyclic voltammetry, stripping voltammetry, ion specific electrodes, X-ray fluorescence, atomic absorption spectroscopy, or other suitable on-line detection methods. Similarly, dissolved radioisotopes can be detected by sensing emitted neutron, gamma, beta, or alpha radiation. For example, on-line neutron and gamma ray spectroscopy can be used. If neutron, gamma ray or x-ray fluorscence detection is used, the sensors can be placed directly on cell 30, instead of on outlet stream 155. Radiation (or other) sensors placed directly on cell 30 can provide a more immediate detection of breakthrough than sensors placed on outlet stream 155, thereby providing more time for response of the control circuitry. Such advance notice can lower the probability of product contamination with unpurified feed solution during breakthrough. This feature is especially important in cases where radioactive solutions are being processed. Direct placement of radiation (or other aforementioned) sensors on cell (30) can also enable the accumulation of contaminants to volumetric concentrations above their respective detection limits, thereby enabling detection. In this application, the process is referred to as "electrochemical intensification" of the detected signal. Organics can be detected with spectrophotometry, Raman spectroscopy, polarography, cyclic voltammetry, enzyme-based electrochemical sensors, liquid or gas chromatography, total organic analyzers, AC impedance spectroscopy, tuned-frequency impedance, capacitance probe, or any other appropriate on-line detection method. Colloidal particles, microbial cells, or other suspended solid-phase particles can be detected with on-line light absorption and scattering equipment. In specific regard to light scattering, either Raleigh or Mie scattering can be used, depending upon particle size. After sensing the onset of breakthrough with sensors on outlet stream 155, or sensors directly on cell 30, flow to the product tank (160) is stopped by automatically closing valve (156).

Conventional regeneration involves a discharging of an electrically charged desalination stack or battery of cells while the regenerating solution is continuously passed through the cells and the concentrated waste outleted from the battery is collected. In the invention, the total amount of waste solution resulting from the regeneration process of the invention is minimized by the slowed or stopped flow operation and/or oxidative chemical treatment of the raw fluid stream. Although the regenerant solutions, having conductivities larger than those of the raw fluid stream, can be recycled to obtain the desired level of purification, a minimum production of waste solution contributes to significant reduction in the complexity, energy requirements, and thus cost of the overall deionization (desalination) process. The process of the invention effects a substantial reduction of secondary waste compared to that of the continuous operation, e.g., at least 20, 50, or 100 volume % or more reduction of waste.

In the process of the invention, when the cell 30 is saturated or it is determined to regenerate the cell, the deionization process can be automatically interrupted, either stopped or slowed down as the regeneration process starts. For this purpose, the power supply 117 is disconnected, reduced, or polarity reversed and a regeneration tank 170, fed deionized or partially deionized fluid from outlet line 156 through an open valve 162 when valve 157 to feed tank 150 is closed, is fluidly connected to the pump 152 via recycle line 164 and to the cell 30 via inlet stream 153. The regeneration tank contains a suitable regenerant solution (only a relatively small amount is needed and can have the same composition as the feed stream, for instance raw water), or alternatively, pure water (e.g., deionized water) or mixtures thereof can be used. The regenerant solution is passed from regeneration tank 170 through the cell 30, and the regeneration process takes place by placing the removed ions back into the regeneration solution. A relatively concentrated solution of the removed ions placed back into regeneration tank 170 during the regeneration process can eventually be passed via regeneration tank outlet 166 to a waste container 168 for disposal or recycle as desired. Although not shown in FIG. 5, outlet recycle lines from waste container 168 and/or product tank 160 can be inletted to cell 30 (usually through pump 152) to provide a source or partial source of regenerant during the regeneration process. The valves and pumps can be controlled by computer 128 and appropriate circuitry during the regeneration process.

In operation, cell 30 is regenerated after stopping product flow by closing valve 156. Valve 145, which separates regeneration tank 170 and pump 152 is opened. Regenerant solution then flows through pump 152, various inlet sensors 154, 136, 135, and/or 134, the cell 30, various outlet sensors 144, 145, and/or 146, and back into regeneration tank 170, thereby forming a closed fluidic loop with complete recycle. With regenerant solution flowing continuously through cell 30 in this closed fluidic loop, the electrodes are either discharged or reverse polarized in a manner to accomplish regeneration. In this closed fluidic loop, the rate of flow during the regeneration cycle can be faster or slower than that during the deionization cycle. The high Reynolds number that can be maintained in this closed fluidic loop enables the system to maintain high rates of mass transfer into the fluid phase from the electrode surfaces while operating with a fluid volume which is small in comparison to the feed and product solutions. Good mass transfer minimizes the time required for regeneration in some cases, thereby reducing the time required for regeneration and increasing the overall generation of product. In this sense, regeneration is the process whereby contaminants immobilized on the surfaces of the electrodes are forced to reenter the fluid phase by appropriate potential and current control. The extent of regeneration is detected with the various pH and conductivity sensors, or other appropriate sensors previously discussed.

In some cases operation with a closed fluidic loop may be desirable, however, in other cases, such as those addressed by the present invention, a stopped, reduced or slow flow operation is preferred for the best results during regeneration. In the case in systems where regeneration is rate limited by surface kinetics instead of fluid-phase mass transfer, the present invention is preferred. If regeneration is controlled by surface kinetics, stopped flow allows more time for immobilized contaminants to leave the electrodes and reenter the regenerant solution. Thus, higher contaminant concentrations can be achieved in this regenerant solution than would be otherwise possible. Since such contaminated regenerant solutions eventually exit cell 30 as a secondary waste solution, higher contaminant concentrations translate into smaller volumes of secondary wastes. Such described operations enable the system to achieve higher contaminate concentrations in the regenerant solution, thereby reducing the volume of secondary waste, associated disposal costs, and environmental impact. (The primary waste is often the feed solution being treated.)

In an alternative mode of operation, regenerative solution from regeneration tank 170 can be directed to cell 30 via flow outlet stream 155 in a "backflush" mode. This mode of operation enables the system to maintain a large concentration gradient across cell 30. Such stratification can enable the system to achieve greater product quality than would otherwise be possible.

In a preferred embodiment during the regeneration portion of a deionization/regeneration cycle, a suitable regenerant solution is passed in sufficient quantity to replace the overall fluid volume of the cell, and the fluid flow then stopped for a desorption period to allow partial or essentially complete release of the previously removed ions from the electrosorptive media materials attached to the electrodes. Such a desorption period is normally completed prior to restarting the fluid flow and/or the fast flushing process. During the slow flow mode rather than the stopped mode, one of ordinary skill in the art can adjust the regeneration flow rate (and fluid volume) through the cell to achieve the desired degree of regeneration of the electrodes.

In the event the electrodes become saturated with organic contaminants, it is possible to clean and regenerate the carbon composite electrode 44, or other porous monolithic electrodes by passing solutions of chemically and electrochemically regenerated oxidants, including but not limited to Ag(II), Co(III), Fe(III), ozone, hydrogen peroxide, and various bleaches such as $ClO^-$, through the electrochemical cell 30. Other effective regenerant solution components include organic acids, surfactants, and chelating agents.

As indicated in an example hereinafter described, a 3% hydrogen peroxide solution can effectively restore capacity to a degraded capacitive deionization (desalination) electrochemical cell previously employed to purify a very brackish aqueous solution of water, such as a solution extracted from backwaters located in Alameda County, California. The fluid volume of electrochemical cell 30 and/or others is replaced with hydrogen peroxide regeneration solution from sources such as from product tank 160, regeneration tank 170 and/or waste container 168 and fluid flow stopped for about 1 hour prior to fast flushing. The results exhibited in the example are surprisingly better when combined with the stopped flow system of the invention compared to a system employing a continuous flow regeneration cycle.

Figure 12:
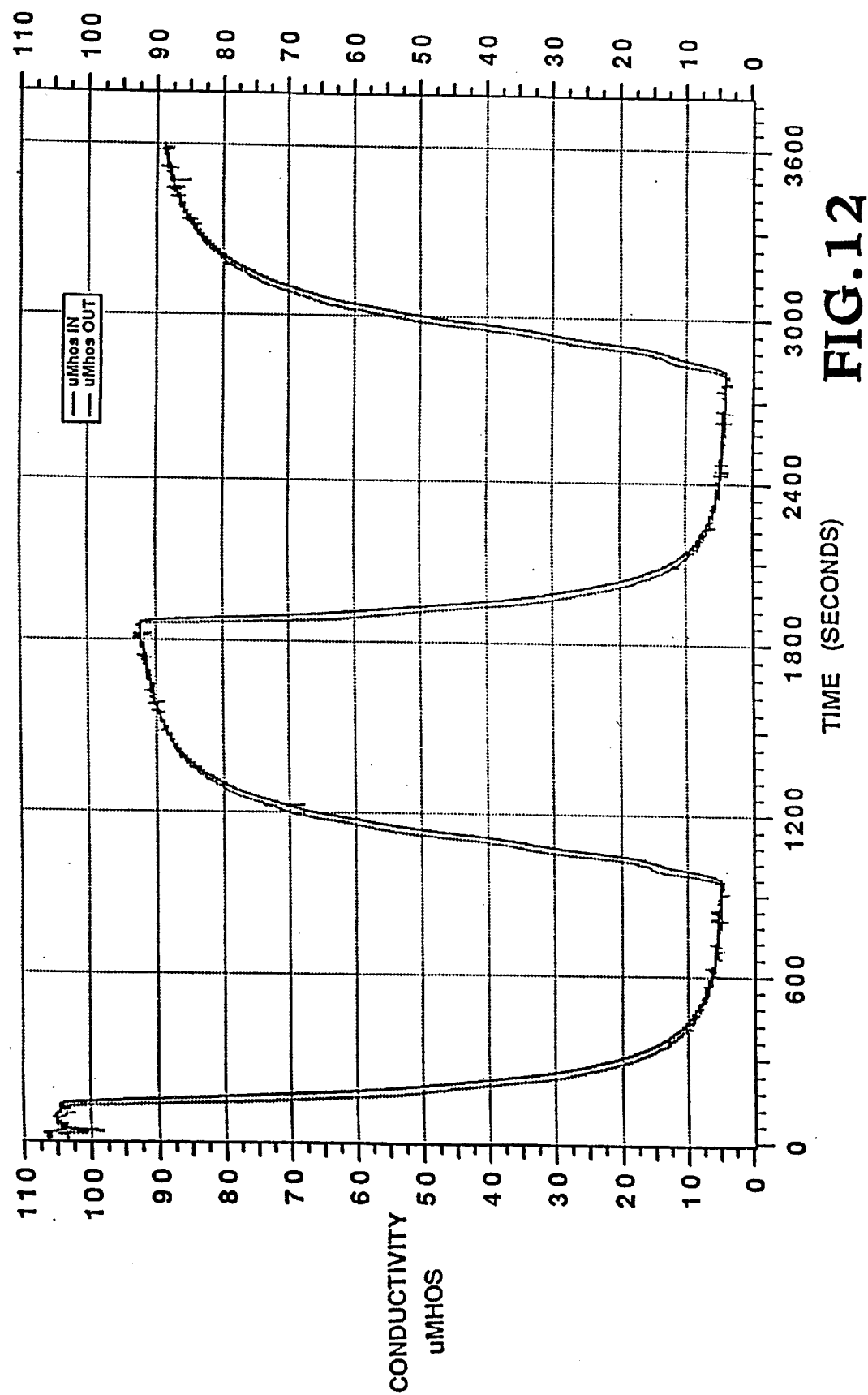
FIGS. 12 through 14 represent empirical timing charts using the capacitive deionization-regeneration system of FIG. 5.
Figure 13:
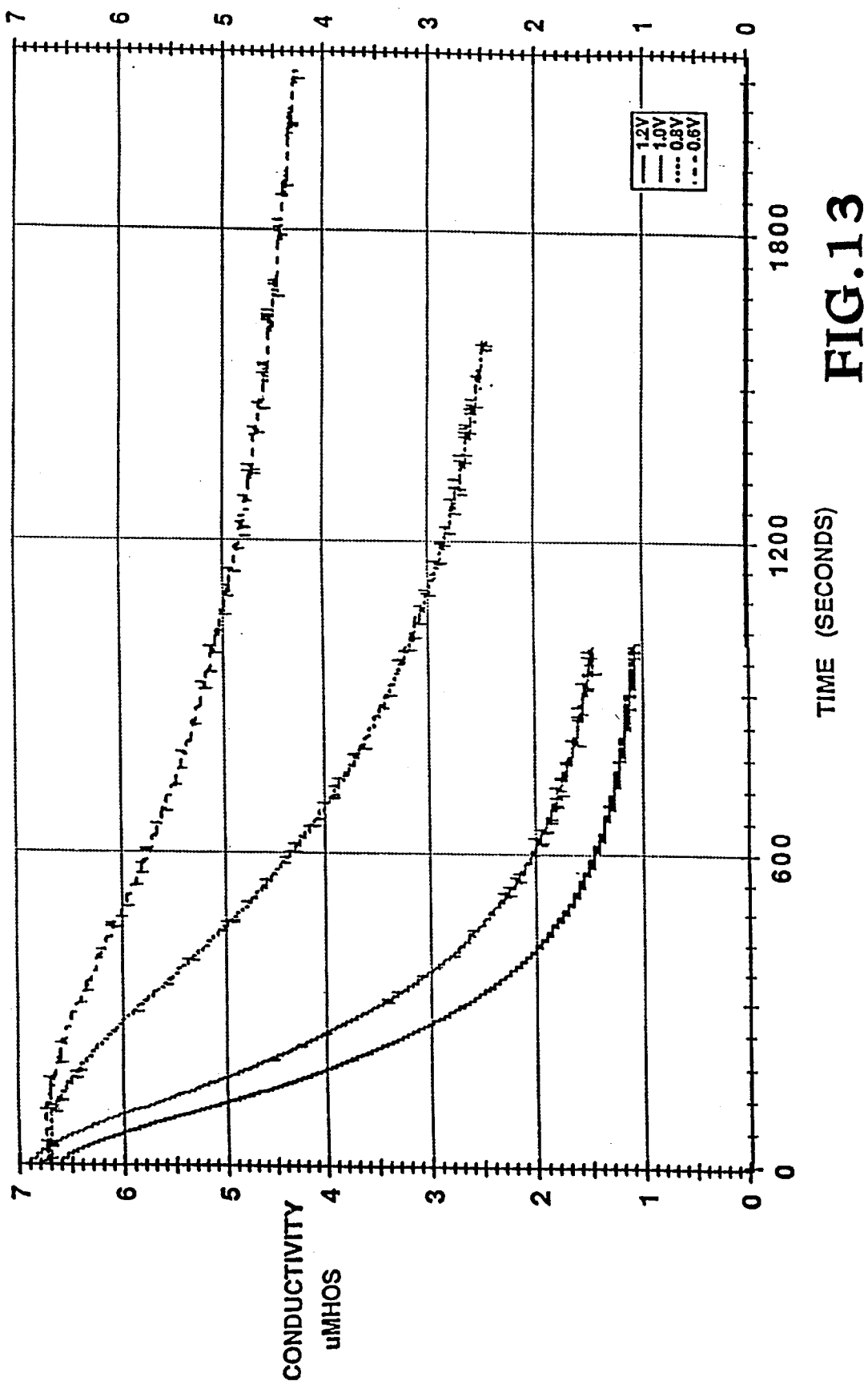
Figure 14:
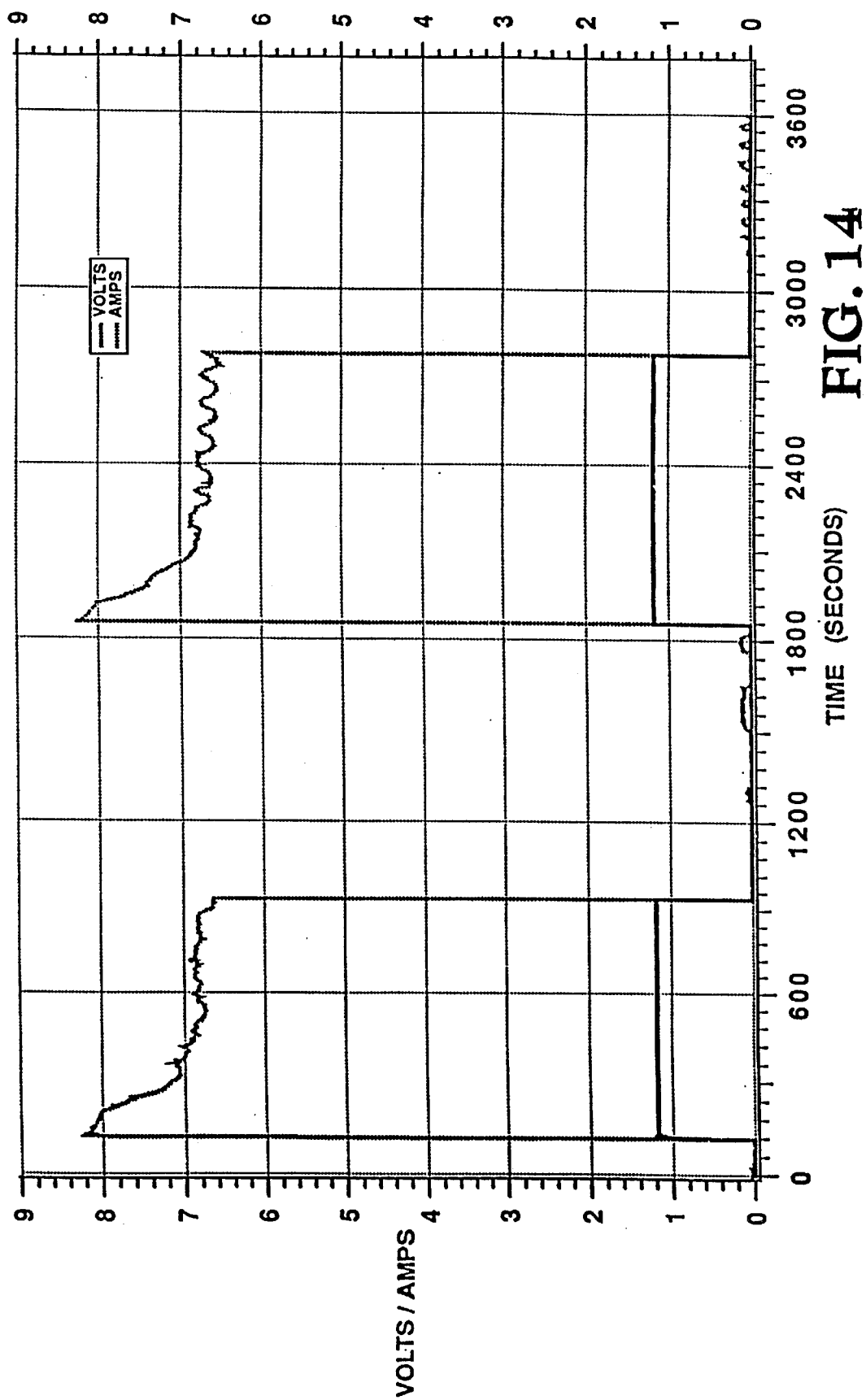

FIGS. 12 through 14 represent empirical timing charts using the capacitive deionization-regeneration system 111 of FIG. 5.

Figure 6:
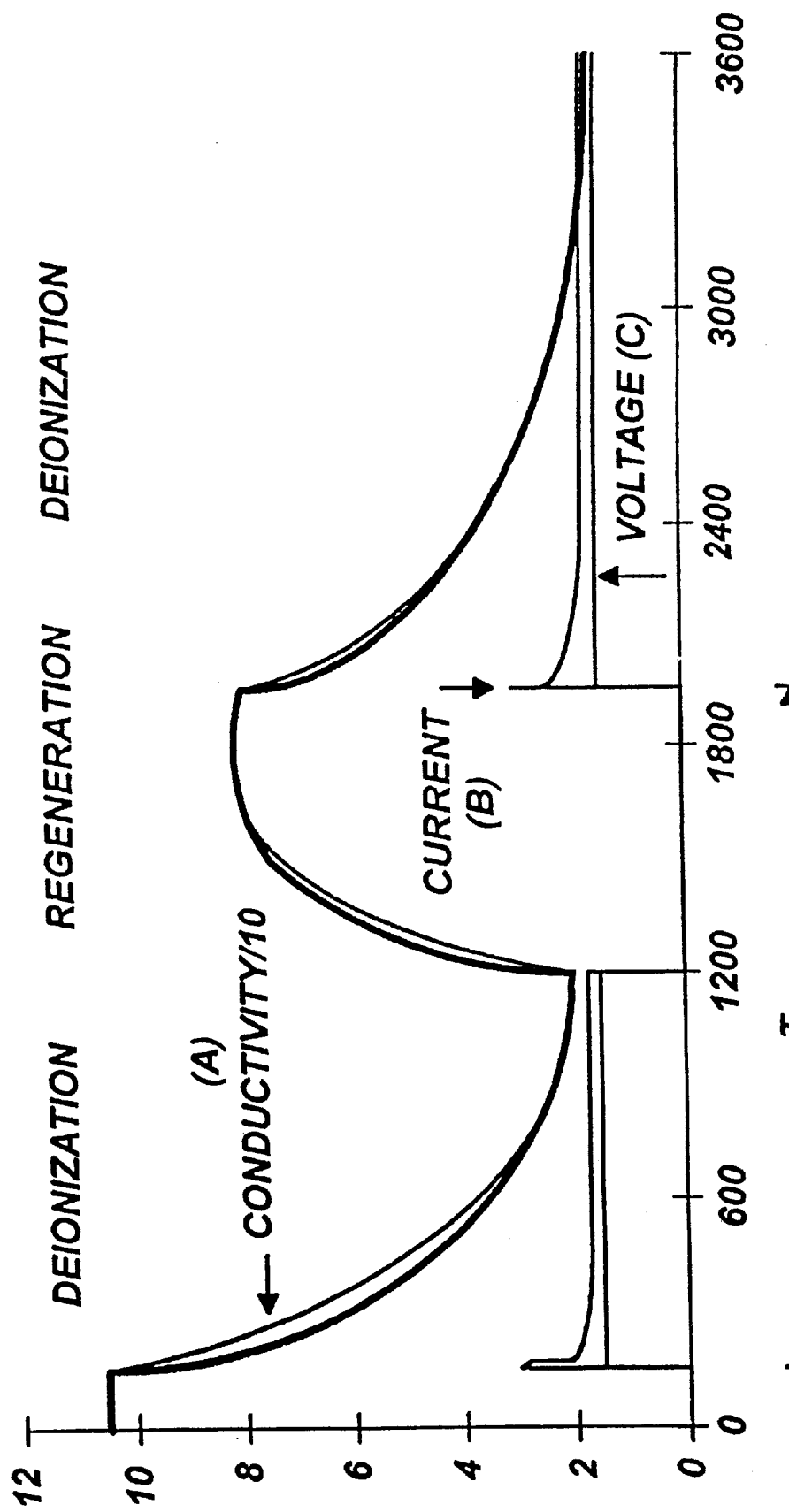
FIG. 6 includes three superposed timing charts illustrating the operation of the capacitive deionization-regeneration system of FIG. 5.

FIG. 6 includes three superposed timing charts A, B, C, illustrating the operation of the capacitive deionization-regeneration system 111 of FIG. 5, used for the deionization and regeneration of 100 micromhos NaCl solution. Chart A represents the conductivity of the electrolyte, and includes two curves, one illustrating the inlet stream conductivity and the other curve illustrating the outlet stream conductivty. Chart B represents the current flowing through the cell 30. Chart C represents the voltage across the cell 30. T represents the deionization-regeneration cycle.

Figure 7:
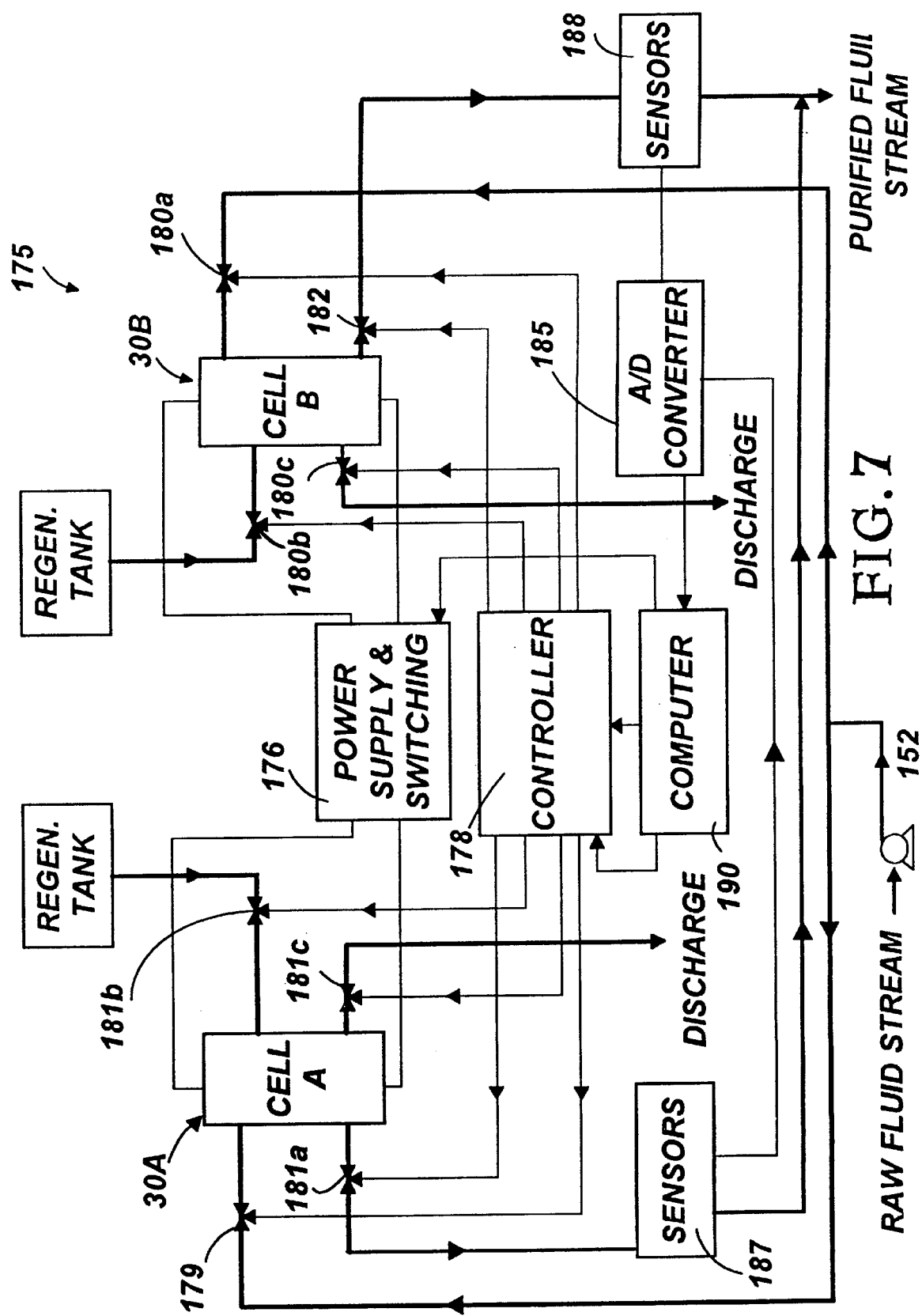
FIG. 7 is a block diagram of a second embodiment of the capacitive deionization-regeneration system using two parallel electrochemical cells, each formed of stacks of numerous electrodes, shown in FIG. 3.
Figure 8A:
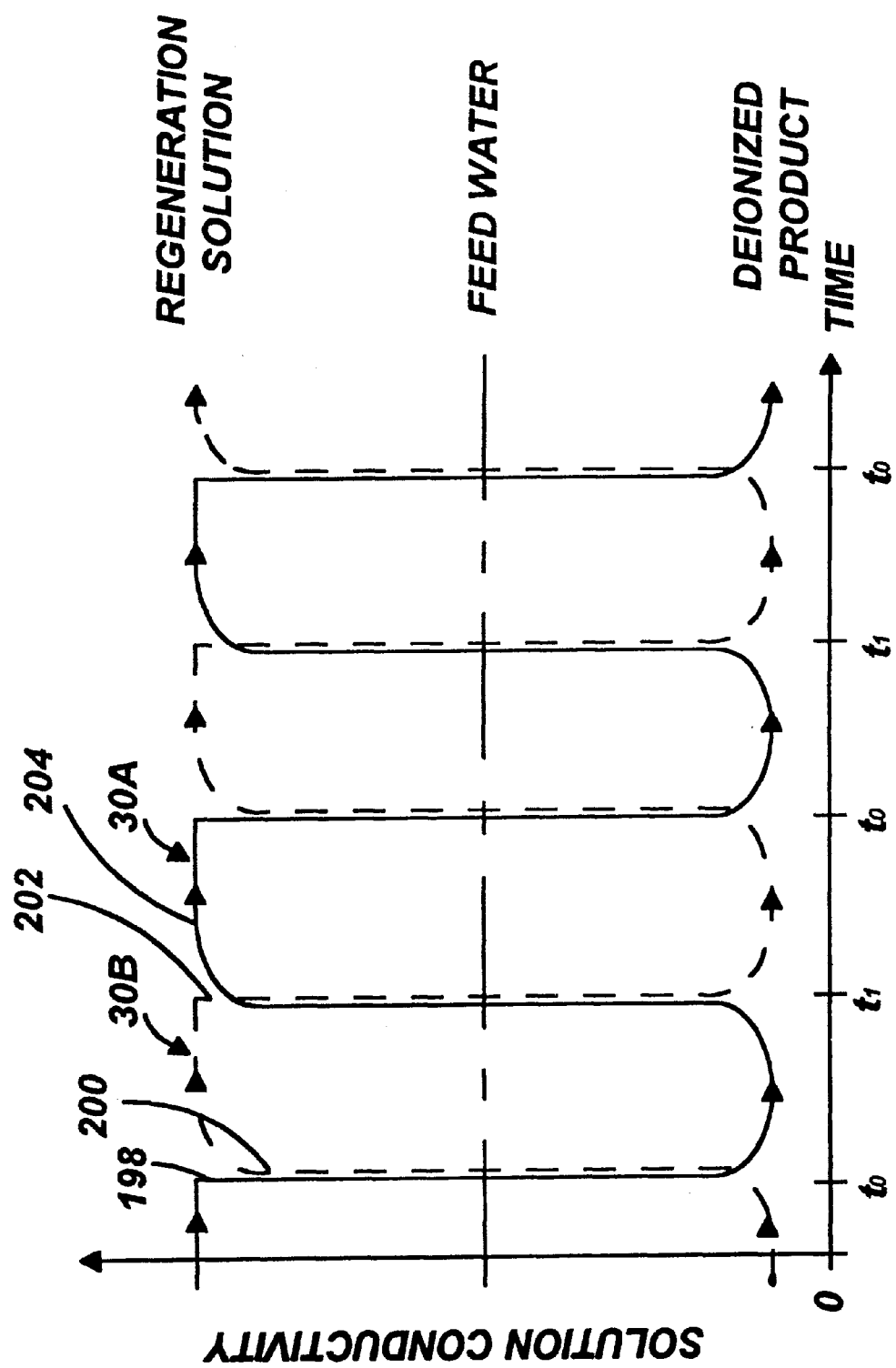
FIGS. 8A, B, C are three timing charts illustrating the operation of the capacitive deionization-regeneration system of FIG. 7.

FIG. 7 illustrates a second embodiment of the capacitive deionization-regeneration system 175 using at least two parallel electrochemical cells 30A and 30B, both similar to the cell 30 shown in FIG. 3. Of course, when more than two parallel cells are utilized, the operation is at phase differences other than 180 degrees, for example, three parallel cells at 120 degrees, etc. FIGS. 8A,B,C show an exemplary operation of the capacitive deionization system 175 using 100 micromhos NaCl solution. One of the main advantages of the system 175 is its ability to maintain a continuous deionization and regeneration operation. The system 175 is generally similar to the system 111, and uses two cells 30A and 30B, such that when one cell 30A or 30B is deionizing the fluid stream, the other cell is regenerating in the same manner as previously described herein, in preparation for the deionization, i.e., purification process. Therefore, the operation of the system 175 is cyclical and continuous. For each one of the cells 30A and 30B, each cycle includes two half cycles. The first half cycle is the deionization process, and the second half cycle is the regeneration process, such that the cycles of the cells 30A and 30B are essentially 180 degrees out of phase.

The system 175 includes a power supply and switching apparatus 176 connected across both cells 30A and 30B, for selectively operating these cells. While the preferred embodiment of the system 175 includes operating one cell for deionizing a fluid stream while the other cell is simultaneously being regenerated, both cells 30A and 30B can simultaneously perform the same process, i.e., deionization or regeneration.

A controller 178 regulates a plurality of inflow and outflow valves 179, 180a, 180b, 180c, 181a, 181b, 181c, and 182, for controlling the flow of the fluid stream to and from the cells 30A and 30B. An analog-to-digital converter 185 converts measurement signals from a plurality of conductivity and ion specific sensors 187, 188 disposed along the fluid circuit of the system 175, and transmits corresponding digital signals to a computer 190, which controls the controller 178, the power supply and switching apparatus 176, and thus the overall operation of the system 175. While only two sensors 187, 188 are shown, other sensors can also be included to provide additional feedback data to the computer 190.

Figure 8B:
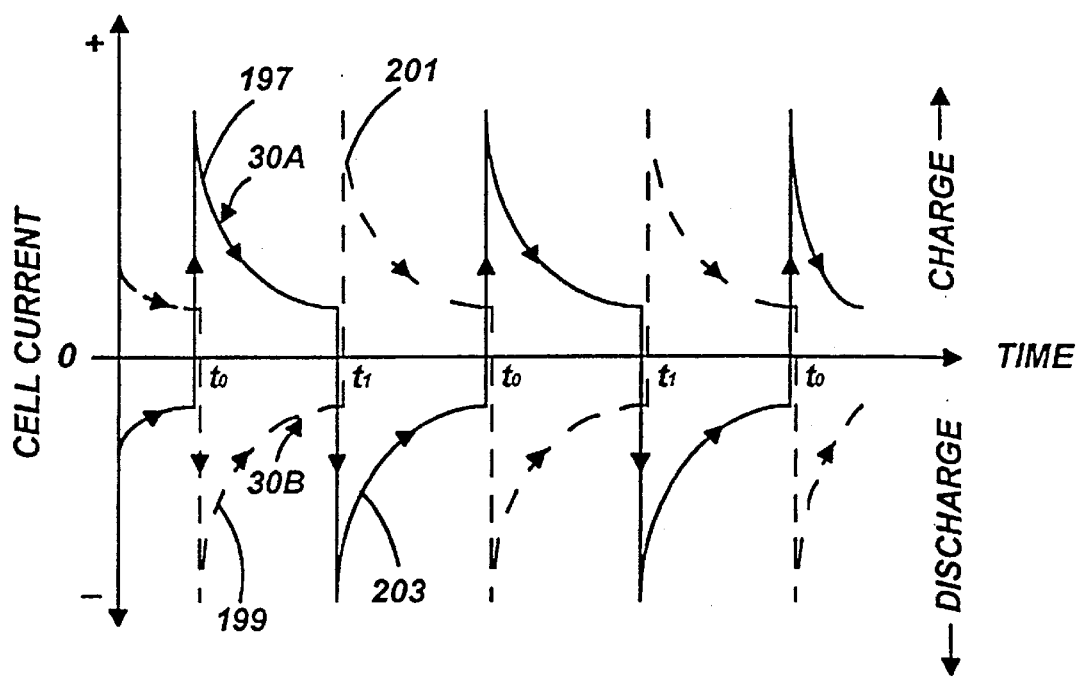
Figure 8C:
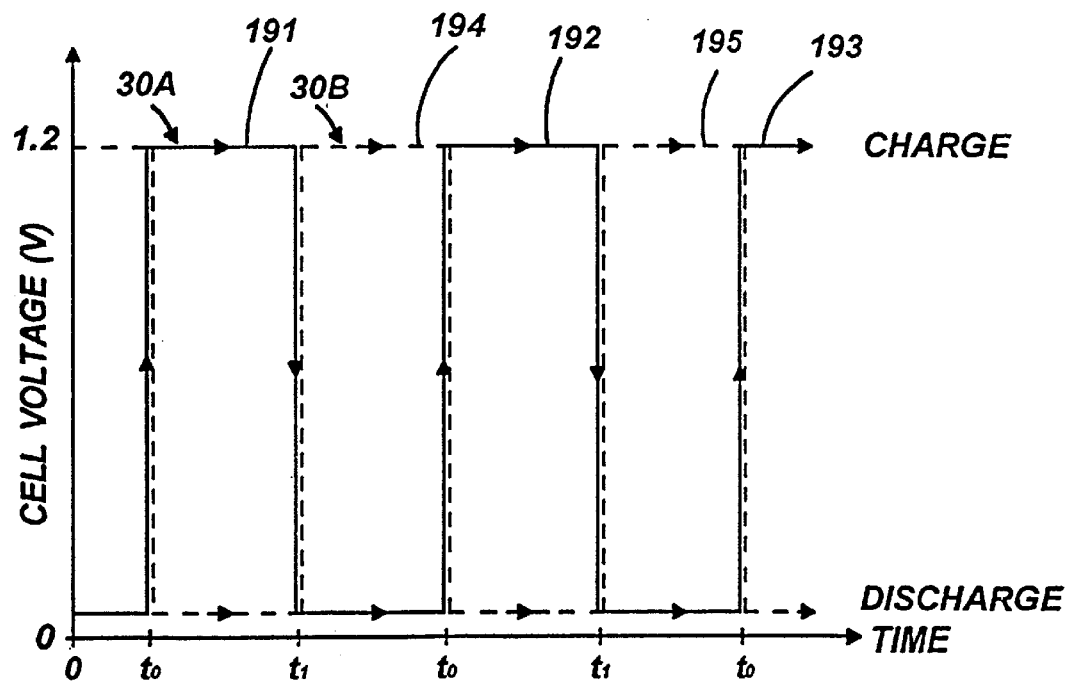

FIGS. 8A,B,C are three timing charts illustrating the operation of the capacitive deionization-regeneration system 175 of FIG. 7. In this case, no electrical power released during the regeneration of one cell is used by the other cell for deionization. FIG. 8A shows the conductivity (micromhos) versus time (seconds), of the effluent fluid streams flowing from the cells 30A and 30B. FIG. 8B shows the current (amperes) flowing through the cells 30A and 30B. FIG. 8C shows the voltage (volts) applied across each cell 30A, 30B. In the case of aqueous (water-based) streams, optimum performance is obtained with a voltage pulse having a preferred amplitude of 0.6–1.2 volts. Lower voltages diminish the capacity of the electrodes while significantly higher voltages cause electrolysis and associated gas evolution from the electrodes. However, in some instances, voltages above about 1.2 to as high as about 1.8 can be selectively applied without substantially electrolyzing the water. The solid lines in FIGS. 8A, B, C relate to the behavior of the cell 30A, while the phantom or broken lines relate to the behavior of the cell 30B.

In FIG. 8C, the solid line illustrates a series of square shaped voltage pulses 191, 192, 193 applied across the cell 30A, with a plateau value of about 1.2 volts, while the broken line illustrates a series of square shaped voltage pulses 194, 195 applied across the cell 30B, also with a plateau value of about 1.2 volts. It should however be understood that different voltages can be applied. Specifically, in the case of aqueous streams, the preferred voltages range between 0.6 and 1.2 volts. The range can be extended from about 0.01 to about 4.5 volts in other solvent systems, such as propylene carbonate, DMSO, crown ethers, and the like. In the case of water, potentials less than 0.6 volts can be applied. The voltage pulses applied to cells 30A and 30B are 180 degrees out of phase.

The voltage pulse 191 in FIG. 8C will cause the cell 30A to progress with the deionization process, as illustrated by the current curve 197 in FIG. 8B, and by the conductivity curve 198 in FIG. 8A. While the voltage pulse 191 in FIG. 8C is applied across the cell 30A, the anodes and cathodes of cell 30B are connected together through an external load (i.e., "shorting the cell"), causing cell 30B to regenerate, as illustrated by the current curve 199 in FIG. 8B, and by the conductivity curve 200 in FIG. 8A.

Thereafter, the voltage pulse 194 is applied across the cell 30B causing it to progress with the deionization process, as illustrated by the current curve 201 in FIG. 8B, and by the conductivity curve 202 in FIG. 8A. While the pulse 194 is applied across the cell 30B, the anodes and cathodes of cell 30A are connected together through an external load, causing cell 30A to regenerate, as illustrated by the current curve 203 in FIG. 8B, and by the conductivity curve 204 in FIG. 8A.

The foregoing deionization-regeneration cycle enables the system 175 to operate continuously without interruption, since, as one of the cells 30A, 30B becomes saturated, the other cell is almost or completely regenerated, and is ready to proceed with the deionization process. As a result, the purified fluid stream at the output of the system 175 is continuous. The operation of the system 175 might be particularly attractive in nuclear power plants for scavenging contaminants from boiler water.

To briefly summarize the operation of the system 175, during the deionization process, the corresponding cell, either 30A or 30B, is polarized so as remove ions from the fluid stream passing through it. The removal process can be by electric double layer charging, electrodeposition, electrosorption, electro phoretic deposition, or any other relevant means. At the beginning of the deionization process, the cell has been completely and electrically discharged; at the end of the deionization process, the cell has been completely and electrically charged. Subsequently, during the regeneration process, the corresponding cell, either 30A or 30B, capacitively discharges the electrode pairs forming it (shorting the cell), thereby placing ions into the fluid stream passing through it, greatly increasing the concentration of ions in that stream. At the beginning of the regeneration process, the cell has been completely and electrically charged; at the end of the regeneration process, the cell has been completely and electrically discharged.

Figure 9:
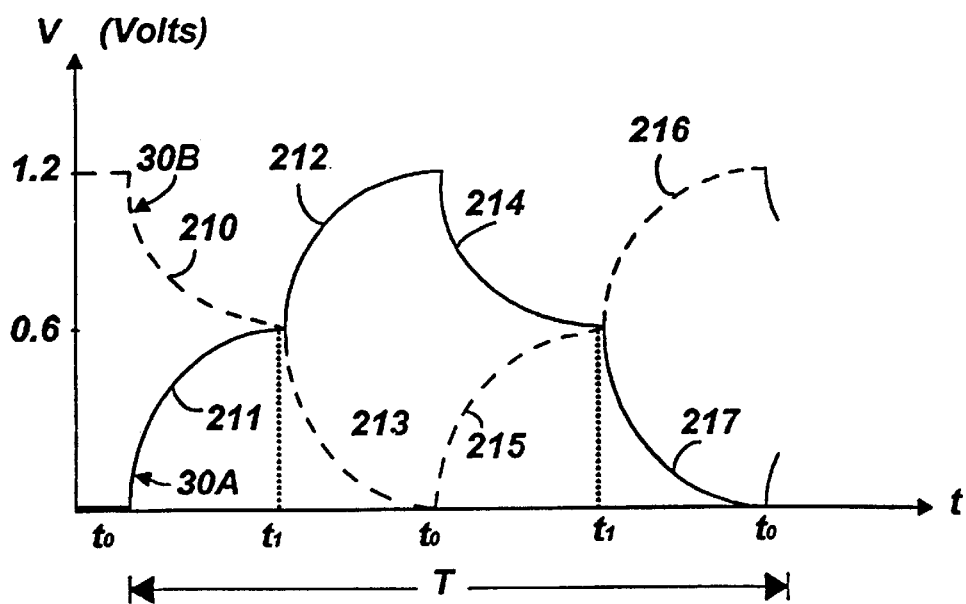
FIG. 9 is a timing chart illustrating the energy saving mode of the system shown in FIG. 7.

FIG. 9 illustrates another characteristic of the present invention when operated in a capacitive mode, namely an enhanced energy efficiency or energy saving mode. In this particular mode of operation, a timing chart is used to illustrate the potential across each of the cells 30A and 30B, where the solid lines relate to the behavior of the cell 30A, while the broken lines relate to the behavior of the cell 30B. Starting at time to, the cell 30B is fully charged and ready to be regenerated, while the cell 30A is fully discharged and ready to begin the deionization process.

While it would be possible to disconnect the cell 30B from the power supply 176, and to connect the power supply 176 to the cell 30A, it is now possible to save energy, and in certain applications, save a significant fraction of the energy required to operate the system 175. According to the present invention, at time to, the cells 30A and 30B can be connected, such that cell 30B is discharged through the cell 30A, as indicated by the curve 210, causing the cell 30A to be charged, as indicated by the curve 211. Electrical energy stored in the cell 30B is used to power the cell 30A during deionization in the cell 30A.

As soon as an equilibrium voltage is reached, for example, at approximately 0.6 volts at time $t_1$, the cell 30A is connected to the power supply 176 so that the charging process can be completed, as illustrated by the curve 212. Simultaneously, the cell 30B is completely discharged through an external load, as indicated by the curve 213. As a result, a significant portion of the energy required to charge the cell 30A is generated by the cell 30B, with the remaining energy supplied by the power supply 176.

Thereafter, at time $t_2$, the cell 30A is fully charged and is ready for regeneration, while the cell 30B is completely discharged, and is ready for the deionization process. The cells 30A and 30B are then connected, such that the cell 30A is discharged through the cell 30B, as illustrated by the curve 214, while the cell 30B is charged, as illustrated by the curve 215.

As soon as the equilibrium voltage is reached at time $t_3$, the cell 30B is connected to the power supply 176 so that the charging process can be completed, as illustrated by the curve 216, and the cell 30A is allowed to completely discharge through an external load, as illustrated by the curve 217. As a result, a significant portion of the energy required to charge the cell 30B is generated by the cell 30A, with the remaining energy supplied by the power supply 176.

Figure 10:
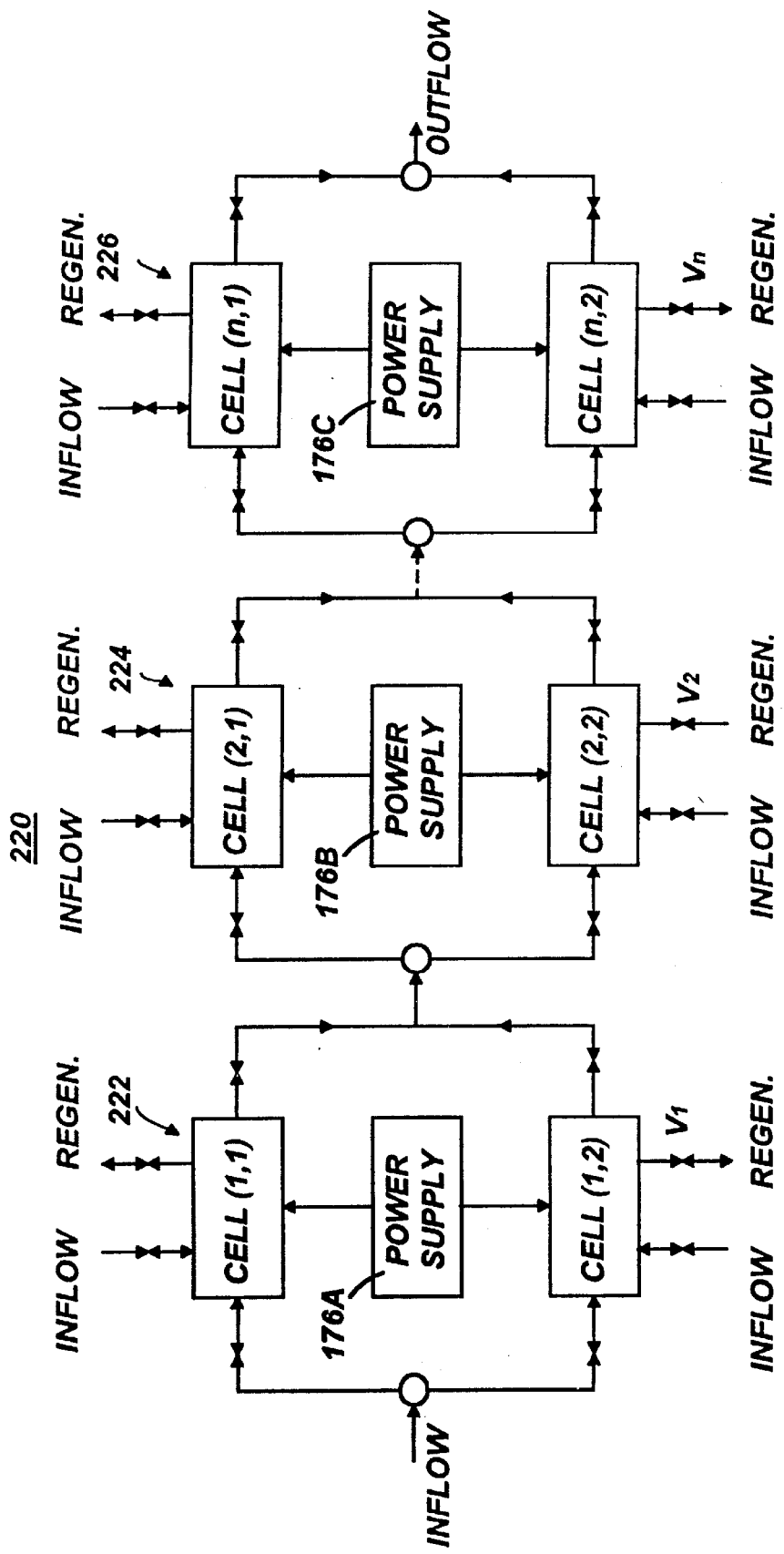
FIG. 10 is a block diagram representation of a third embodiment of a deionization-regeneration system.

FIG. 10 illustrates a third embodiment of a deionization-regeneration system 220 which includes a matrix of systems 222, 224, 226 similar to the system 175 (FIG. 7), which are connected in series. Each system includes at least one pair of cells which are connected and which operate as described in relation to the system 175. Thus, the system 222 includes cells (1,1) and (1,2); the system 224 includes cells (2,1) and (2,2); and the system 226 includes cells (n,1) and (n,2). Each of the systems 222, 224, 226 includes a power supply and switching system 176A, 176B, 176C, which is similar to the power supply and switching system 176 shown in FIG. 7.

In operation, when one cell, i.e., (1,1) of the pair of cells, i.e., 222, is performing the deionization process, the other cell, i.e., (1,2), is being regenerated. While only three systems 222, 224, 226, each including two cells, are shown, a different combination of systems or cells can be selected.

One novel application for the system 220 is the progressive and selective deionization and regeneration feature. Different potentials ($V_1$, $V_2$, $V_n$) are applied across each system (222, 224, 226, respectively) in order to selectively deionize the influent fluid stream, by having each system (222, 224, 226) remove different ions from the fluid stream. Thus, in this particular example, $V_1 < V_2 < V_n$, such that the system 222 is capable of removing reducible cations such as $Cu^{++}$; the system 224 is capable of removing reducible cations such as $Pb^{++}$; and the system 226 is capable of removing non-reducible and non-oxidizable ions such as $Na^+$, $K^+$, $Cs^+$, $Cl^-$, or other similar ions, which remain in their ionic state.

Figures 11A, 11B:
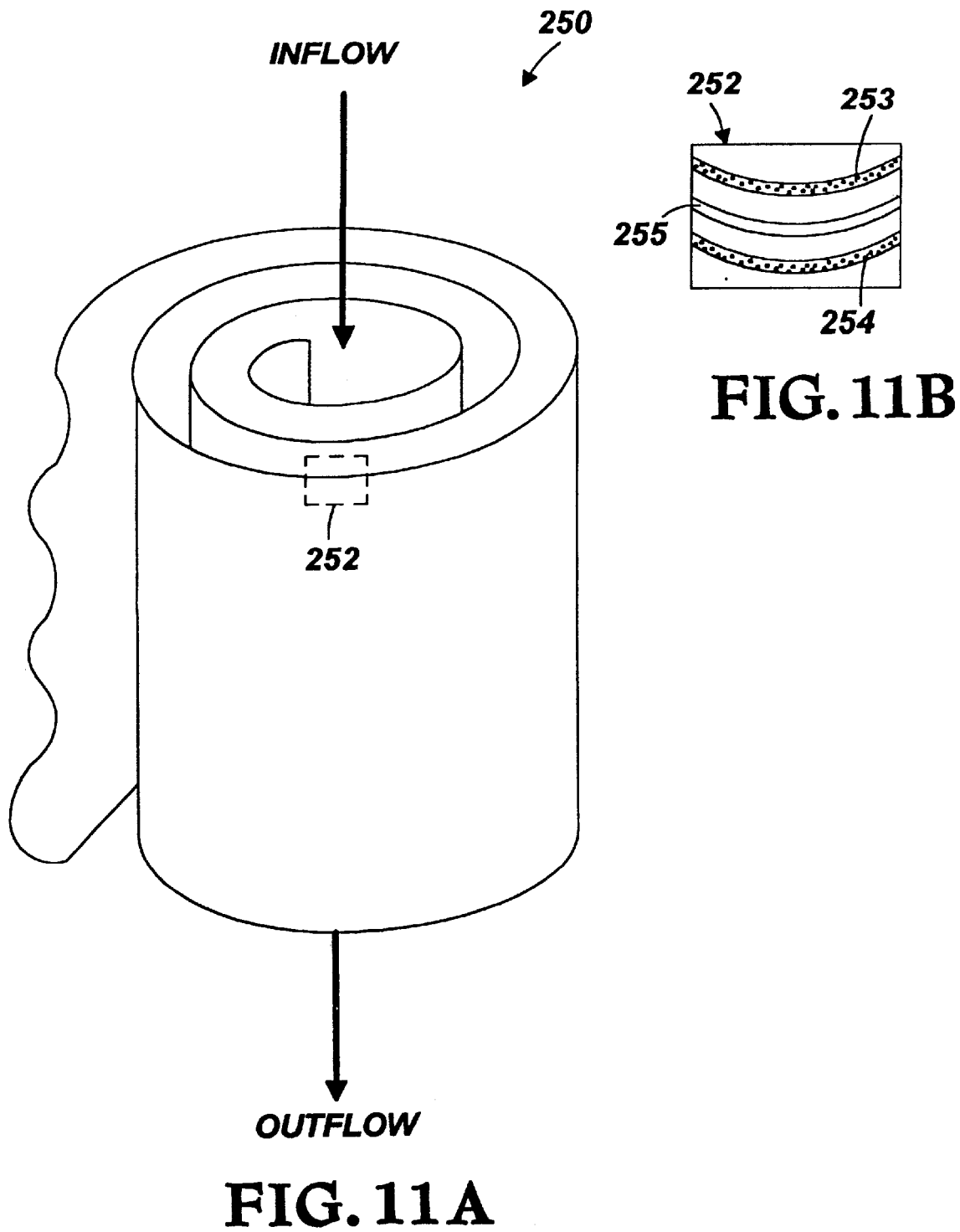
FIGS. 11A,B are a schematic isometric view and enlarged portion of another embodiment of an electrochemical cell.

FIGS. 11A, B, represent an electrochemical cell 250, and a portion 252 thereof. The cell 250 can be adapted for use as part of the capacitive deiorization-regeneration systems 111 and 175 of FIGS. 5 and 7, respectively. The cell 250 includes a plurality of electrodes 253, 254 that are separated by a porous separator such as membrane 255. The separator 255 is sandwiched between two adjacent electrodes 253, 254, and still allows an open channel to be formed and defined therebetween. The electrodes 253 and 254 are similar to the electrodes of cells 30, 30A and 30B described above. The electrodes 253, 254 and the separator 255 are rolled spirally together, so that the electrolyte flows in the open channels formed between the electrodes 253, 254, and exits the cell 250 with minimal or essentially no flow resistance, i.e., a pressure drop of less than 5 psig. While the cell 250 has been described as including two electrodes 253, 254 and one separator 255, additional electrodes and separators can be used.

Figure 15:
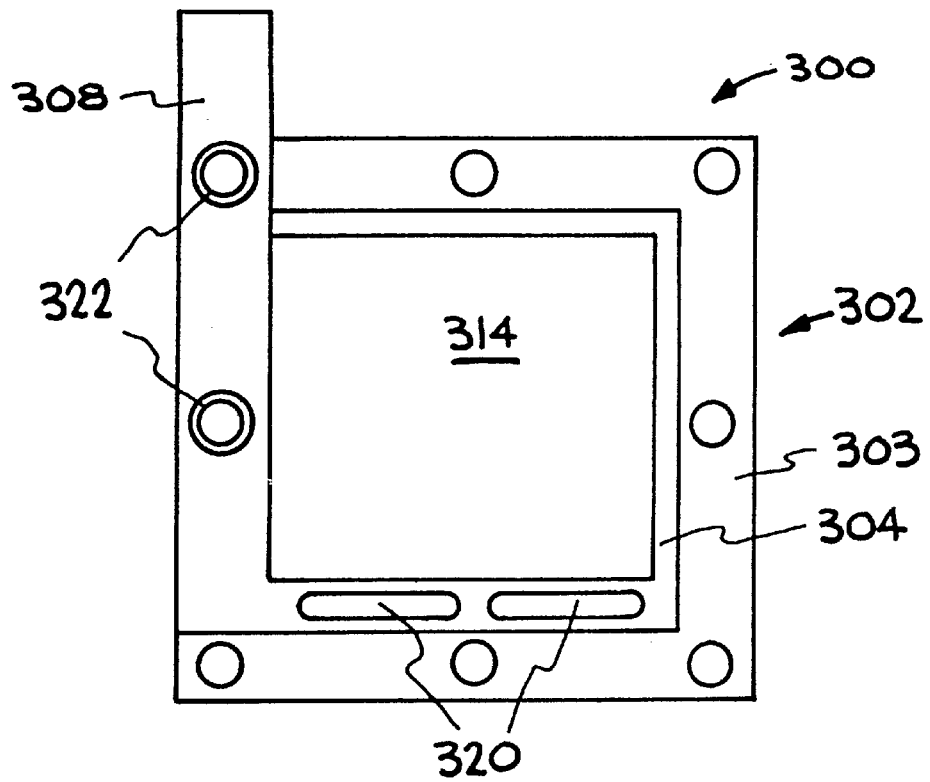
FIG. 15 is a greatly enlarged top plan view of another electrode.
Figure 16:
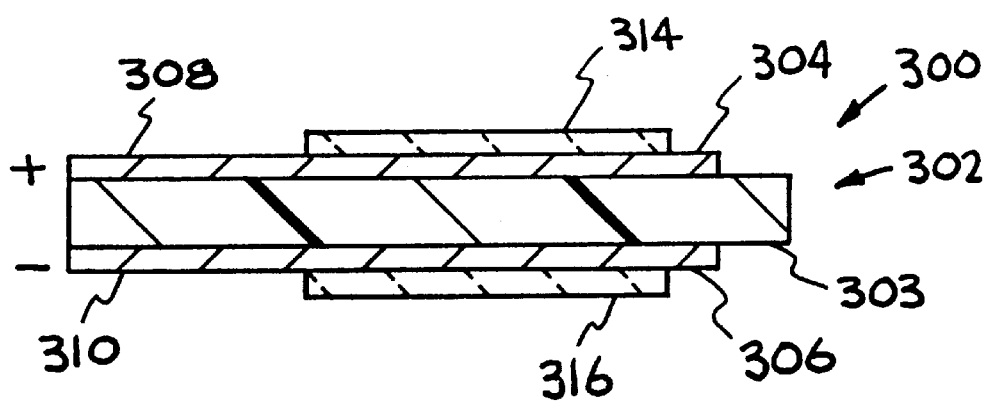
FIG. 16 is an enlarged side elevational view of the electrode of FIG. 15.

FIGS. 15 and 16 illustrate another double-sided electrode 300, for use in the cells and systems described herein. While a double-sided electrode will be described in detail for illustration purpose only, a single-sided electrode can be designed using the same or similar concepts.

Electrode 300 has a generally similar function to electrode 35 of FIG. 4A. Electrode 300 includes a substantially flat, thin, corrosion resistant, rectangularly shaped structural support member 302, which comprises a dielectric board, substrate, or sheet 303. In one embodiment, support member 302 is fabricated using printed circuit board technology for replacing the more expensive metallic (i.e., titanium) structural support 40 of FIG. 4A. Thus, support member 302 may be a metallized epoxy board formed by metallizing at least part of dielectric board 303 with a thin metallic layer or film 304. In another embodiment, dielectric board 303 includes a fiberglass epoxy board.

Metallic layer 304 may be composed of any suitable metal, such as titanium, and can be formed through alternative manufacturing processes, including sputtering the metal onto the surface of dielectric board 303 and chemical vapor deposition (CVD) of metallic film or layer 304 on the surface of dielectric board 303. The opposite side of dielectric board 303 is similarly metallized with a metallic layer 306.

A tab 308 extends integrally from one side of metallic layer 304, for connection to one pole of a D.C. power source. If tab 308 lacks structural rigidity required for specific applications, dielectric board 302 can be extended underneath tab 308 to provide the required mechanical support. Another tab 310 similarly extends integrally from the opposite metallic layer 306 to the other pole of the D.C. power source. Both tabs 308 and 310 could also have the same polarity.

A thin sheet 314 of high specific area, porous, conductive, monolithic material (e.g., carbon aerogel composite) is bonded to the surface of metallic layer 304. In one embodiment, sheet 314 is glued to metallic layer 304 with an electrically conductive epoxy. Conductive sheet 314 is substantially similar in composition to sheet 44 in FIG. 4A. Another thin conductive sheet 316 has a similar composition to that of conductive sheet 314, and is bonded to the opposite metallic sheet 306.

Structural support member 302 further includes a series of generally identical apertures 320 for providing a passage to the electrolyte through electrode 300, and peripheral holes 322, which are similar to apertures 47 and peripheral holes 48 in FIG. 4A.

Figure 17:
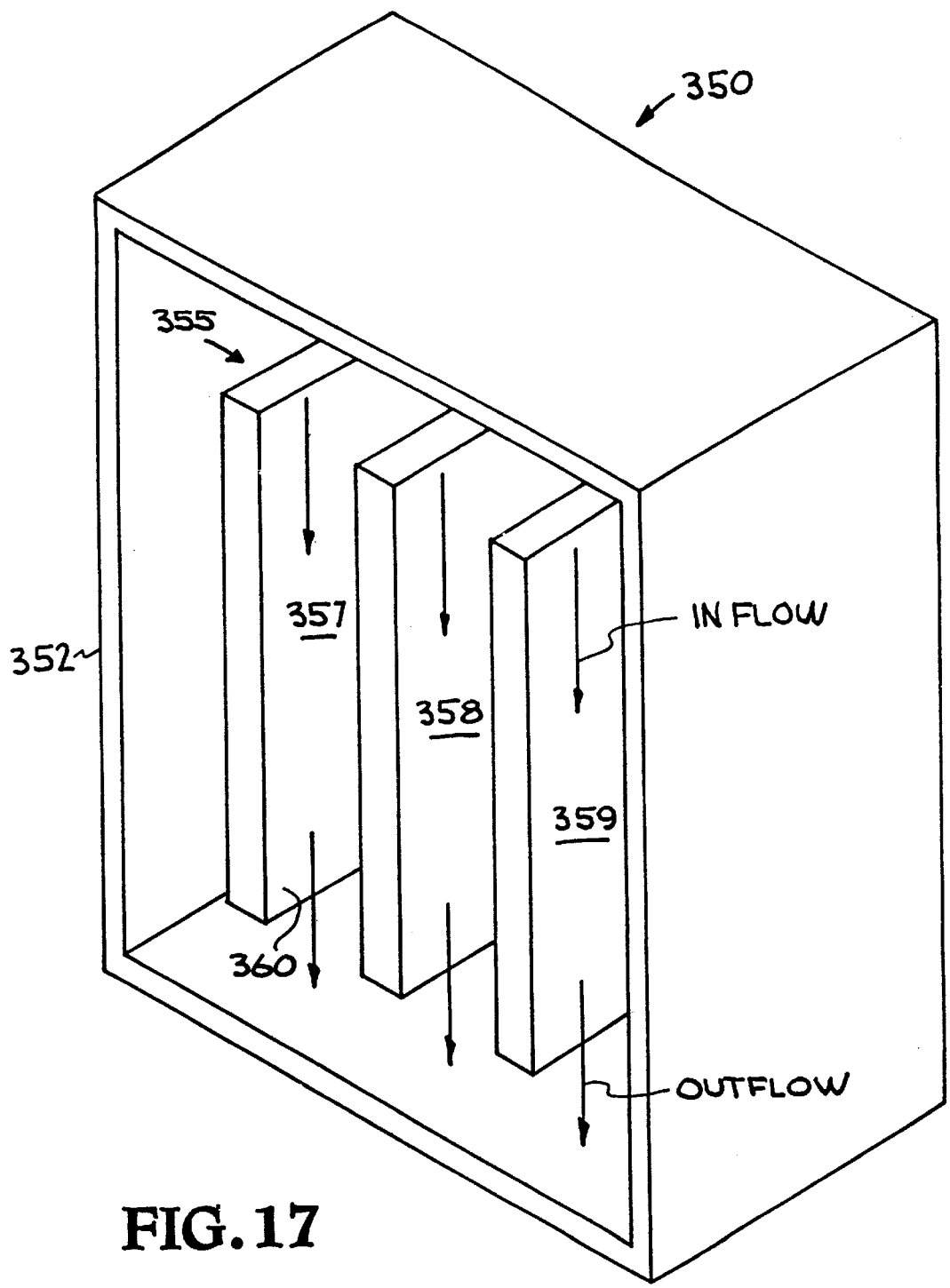
FIG. 17 is a partly sectional, schematic, isometric view of a cartridge.

FIG. 17 shows a cartridge 350 which includes a case 352 and a cell 355 enclosed therein. Cell 355 includes a plurality of electrodes 357, 358, 359, disposed in a parallel relationship relative to each other. While only three electrodes are shown, a different number of electrodes may be selected.

In one embodiment, the end electrodes 357, 359 are single-sided, while the intermediate electrode 358 is double-sided. Electrodes 357, 358, 359 may be generally similar in design, construction and composition to electrode 300 of FIGS. 15 and 16. In another embodiment, electrodes 357, 358, 359 do not include a structural support member 302. High specific surface area, porous, conductive, monolithic materials may be used alone as electrodes and are separated and maintained at a predetermined distance by either dielectric spacers or placement grooves in case 352, such that adjacent electrodes, e.g., 357, 358 define channels or clearances 360 therebetween. In these embodiments, electrodes 357, 358, 359 may form one or more integral cells, such as cell 355, that can be removed from, and replaced within case 352 to form a cell or cartridge 350.

In use, cell 355 is secured to, and placed within case 352, and is connected to a D.C. power source. A fluid stream is allowed to flow freely within channels 360, under the force of gravity, between electrodes 357, 358, 359, as indicated by the arrows labeled INFLOW and OUTFLOW. The basic operation of cartridge 350 has been explained above in relation to cell 30. A pump (not shown) may also be used. While cell 355 is illustrated as having three flat electrodes 357, 358, 359, other electrodes of different shapes may be used. For instance electrodes 357, 358, 359 may be positioned within case 352 so as to provide a serpentine flow (See FIG. 3).

One advantage presented by cartridge 350 is that cell 355, or even the entire cartridge 350, can be easily replaced for maintenance or other purposes. Additionally, cartridge 350 can be scaled to any desired size. Furthermore, the size and weight of cartridge 350 are reduced by eliminating the structural support 302 in FIG. 15.

Figure 18:
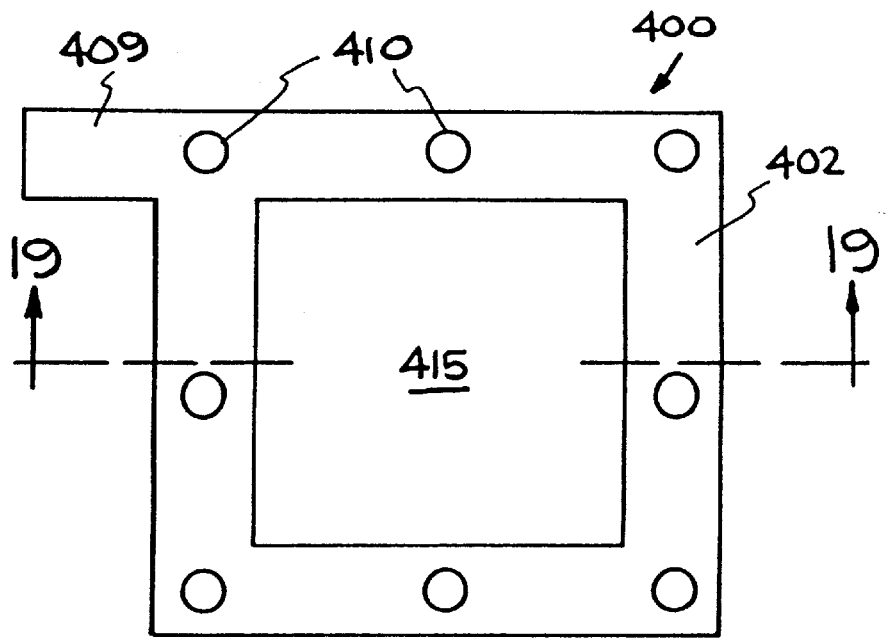
FIG. 18 is a top plan view of another electrode.
Figure 19:
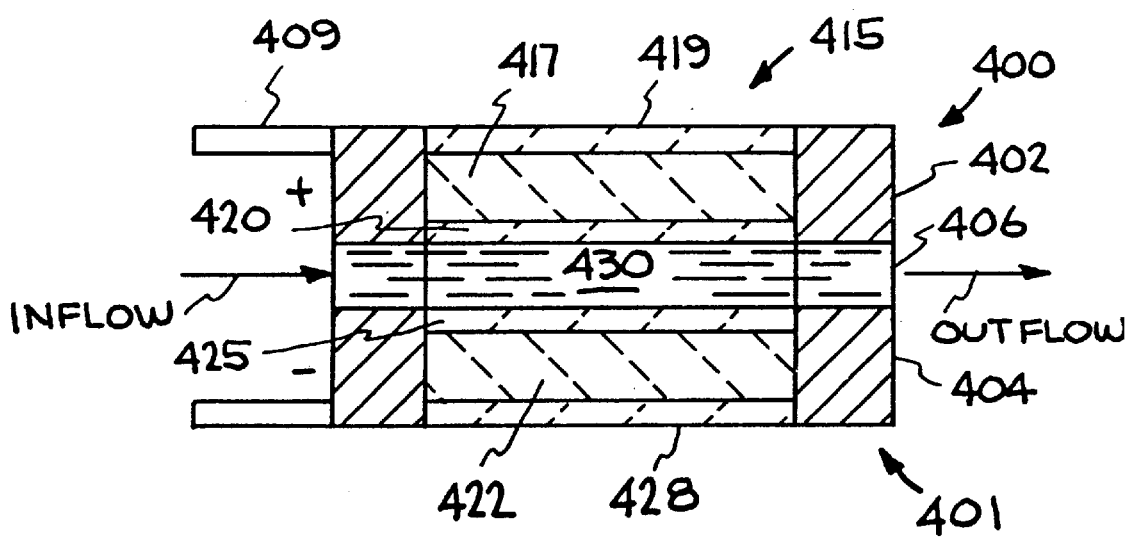
FIG. 19 is a cross-sectional view of the electrode of FIG. 18 taken along line 19—19.

FIGS. 18, 19 show two other electrodes 400, 401. Electrode 400 generally includes a flat, rectangularly shaped, centrally hollow, peripheral support member 402. Similarly, electrode 401 generally includes a flat, rectangularly shaped, centrally hollow, peripheral support member 404. Both electrodes 400, 401 are maintained at a predetermined separation distance by means of a dielectric separator 406. While only two electrodes 400 and 401 may be connected to form a cell, more than two electrodes can be combined to form a cell.

Support members 402, 404 are generally similar in composition and construction. Support member 402 is made of conductive material, such as titanium, and extends integrally from one of its sides into a tab 409 for connection to a pole of a D.C. power source. Support member 402 can be formed of a metallized epoxy board. A plurality of peripheral holes 410 are formed in support member 402 for assembling a cell, as before.

Electrode 400 further includes a refill cartridge 415 that fits within, and fills a central opening surrounded by peripheral support member 402. In general, cartridge 415 is rectangularly shaped, but other shapes can be used. Cartridge 415 may include a refill member comprised of a porous sponge 417 made by powder metallurgy. Sponge 417 can be made of titanium, platinum or other suitable metal. In a preferred embodiment, sponge 417 can be made of reticulated vitreous carbon (RVC) impregnated by resorcinal-formaldehyde carbon aerogel. Sponge 417 is coated on its upper and lower sides with two thin sheets 419, 420 of high specific area, porous, conductive, monolithic material, such as carbon aerogel composite. Sponge 417 could also be a packed volume of particulate carbon, carbon aerogel, or metal. Buckminster fullerene or "Bucky Balls" may also be used to fill the central opening.

Conductive sheets 419, 420 may be bonded, such as by gluing, to substantially the entire surface of the sponge upper and lower sides. Conductive sheets 419, 420 are electrically and physically connected to support member 402, so as to establish electrical contact with the corresponding pole of the D.C. power source.

Electrode 401 is generally similar in construction and composition to electrode 400, and includes a refill cartridge 422 coated with two conductive sheets 423, 425. In operation, electrode 400 is connected to one pole of the D.C. power source, while electrode 401 is connected to the other pole. A fluid stream is allowed to flow, either freely, under the force of gravity, or under minimal pressure, through a channel 430 defined between electrodes 400, 401, as indicated by the arrows labeled INFLOW and OUTFLOW. The basic operation of the cell or cartridge formed of at least electrodes 400, 401 has been explained above in relation to cell 30.

Figure 20:
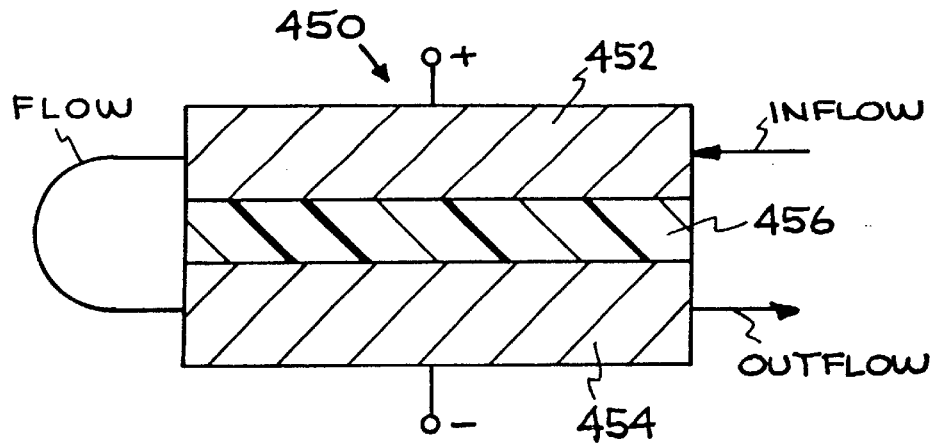
FIG. 20 is a cross-sectional side elevational view of yet another cartridge or cell.

FIG. 20 shows another cartridge or cell 450 which includes at least two substantially similar electrodes 452, 454 that are connected to opposite poles of a D.C. power source. Electrodes 452, 454 are maintained at a predetermined separation distance by a dielectric separator 456. While separator 456 is optional, electrodes 452, 454 are not allowed to be electrically connected.

Electrode 452 is porous and generally rectangularly shaped. Electrode 452 may be made of any spongeous, foamy or porous material, such as a metal sponge or reticulated vitreous carbon (RVC) impregnated with carbon aerogel or a similar high specific area, conductive, monolithic substance, in order to enhance the active surface area of electrode 452. Different electrodes may be impregnated with different compounds. For example, organic or inorganic anion or cation exchangers can be employed.

In use, cell 450 is connected to the D.C. power supply, and a fluid stream is allowed to flow, either freely, under the force of gravity, or under minimal pressure, through electrodes 452, 454, as indicated by the arrows labeled INFLOW, FLOW and OUTFLOW. The basic operation of cell 450 is similar to cell 30. The fluid stream flows through the large pores of electrodes 452 and 454. Carbon aerogel is used to coat the surfaces of the carbon foam.

Chemical regeneration may include the use of strong acids like HCl, $HNO_3$, $H_2SO_4$, $H_2S$, so that they dissolve solid metals that have become deposited on the surface of the (carbon aerogel) electrode, and remove other types of scale formation. Alternatively, chemical regeneration could include the use of strong bases capable of dissolving various types of scales and impurities in order to regenerate the electrodes. Chemical regeneration can involve the organic acids and/or chelating agents, such as EDTA, and the like, and others that allow the use of smaller portions of regenerant. Of course, the overall structural components of the herein described systems should encompass materials capable of withstanding any deleterious effects due to passing chemical regenerant compositions through or contacting them with the system components.

In one embodiment, a heavy organic solvent is used to dissolve heavy organic fouling, followed by a strong chemical oxidant such as ozone, hydrogen peroxide, Fenton's reagent, silver (II), cobalt (III), iron (III), or peroxydisulfate ($S_2O_8^{-2}$). These oxidants can oxidize very thin layers of organic contaminants that have been chemisorbed to the surface of the electrode, thereby regenerating the electrode, particularly in the stopped flow, slow flow and/or fast flush modes. Thus, an important aspect of the present invention is that the carbon electrodes are chemically resistant and regenerative. Additionally, the periodic reversal of the electrode potential will permit the electrode to regenerate very effectively. The regeneration of the electrode will prolong the effective life of the electrode and cell, and will lower the maintenance and operating cost. Periodic voltage reversal can be done while passing feed stream through the cell, or while passing chemical regenerant (acid, base, etc.) through the cell, particularly while employing the stopped flow, slow flow and/or fast flush modes.

According to the present invention, a new class of electrosorption media may be used in the present capacitive deionization and regeneration systems, cells and methods. These electrosorption media are less susceptible to poisoning and degradation than carbon-based materials, including carbon aerogel, reticulated vitreous carbon foam and carbon powder. They include a number of metallic carbides that can be in the form of powders, particles, foams, sponges, or porous solids made by flame spraying or powder metallurgy, sputtered thin films, or formed by other processes. These carbides include TiC, ZrC, VC, NbC, TaC, UC, MoC, WC, $MO_2C$, $Cr_3C_2$, $Ta_2C$, and similar carbides that are stable at high temperatures, chemically resistant, and highly conductive with a resistivity ranging between about 17 $\mu$ohm-cm and 1,200 $\mu$ohm-cm.

Figure 21:
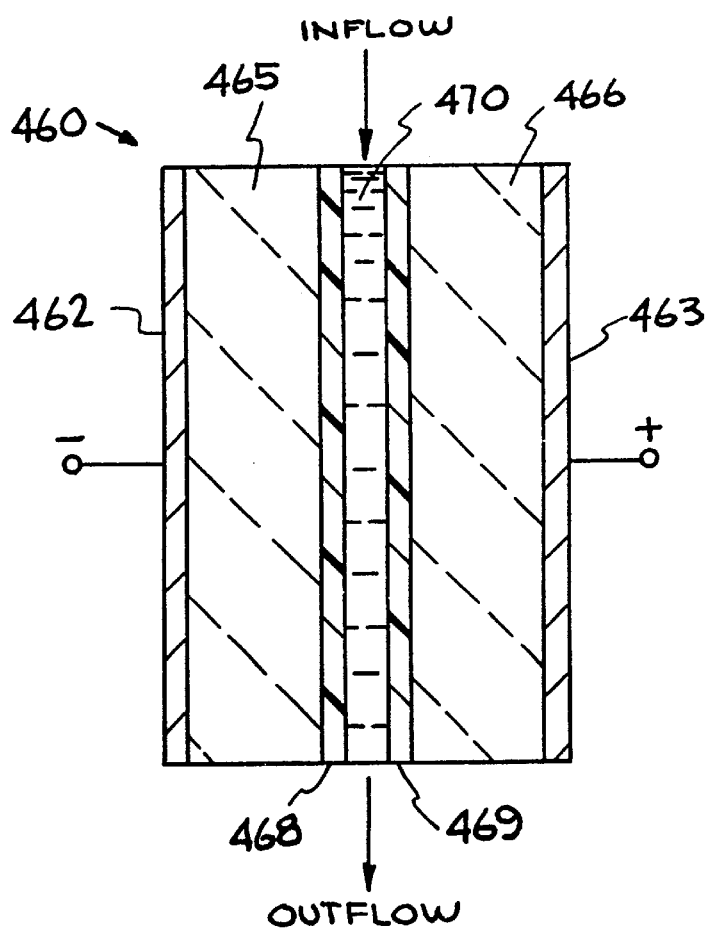
FIG. 21 is a side view of a cell formed of an electrosorption medium.

FIG. 21 shows a cell 460 that may be adapted for use in the capacitive cells and systems of the present invention. Cell 460 can be used in several other applications, such as in electrolyte capacitors for energy storage, and for load leveling in electric vehicles.

Cell 460 is mainly formed of two outer conductive plates 462, 463 connected to a D.C. power source. Two beds 465, 466 of a powdered or granular electrosorption medium selected from the above group, as well as activated carbon powder and various metallic powders, are retained against their corresponding plates 465, 466 by means of two porous or conductive membranes 468, 469, respectively.

A channel 470 is formed centrally between membranes 468, 469, to insure a free, unobstructed flow of fluid therethrough. The principle of operation of cell 460 is similar to that of capacitive deionization cells described herein.

Figure 22:
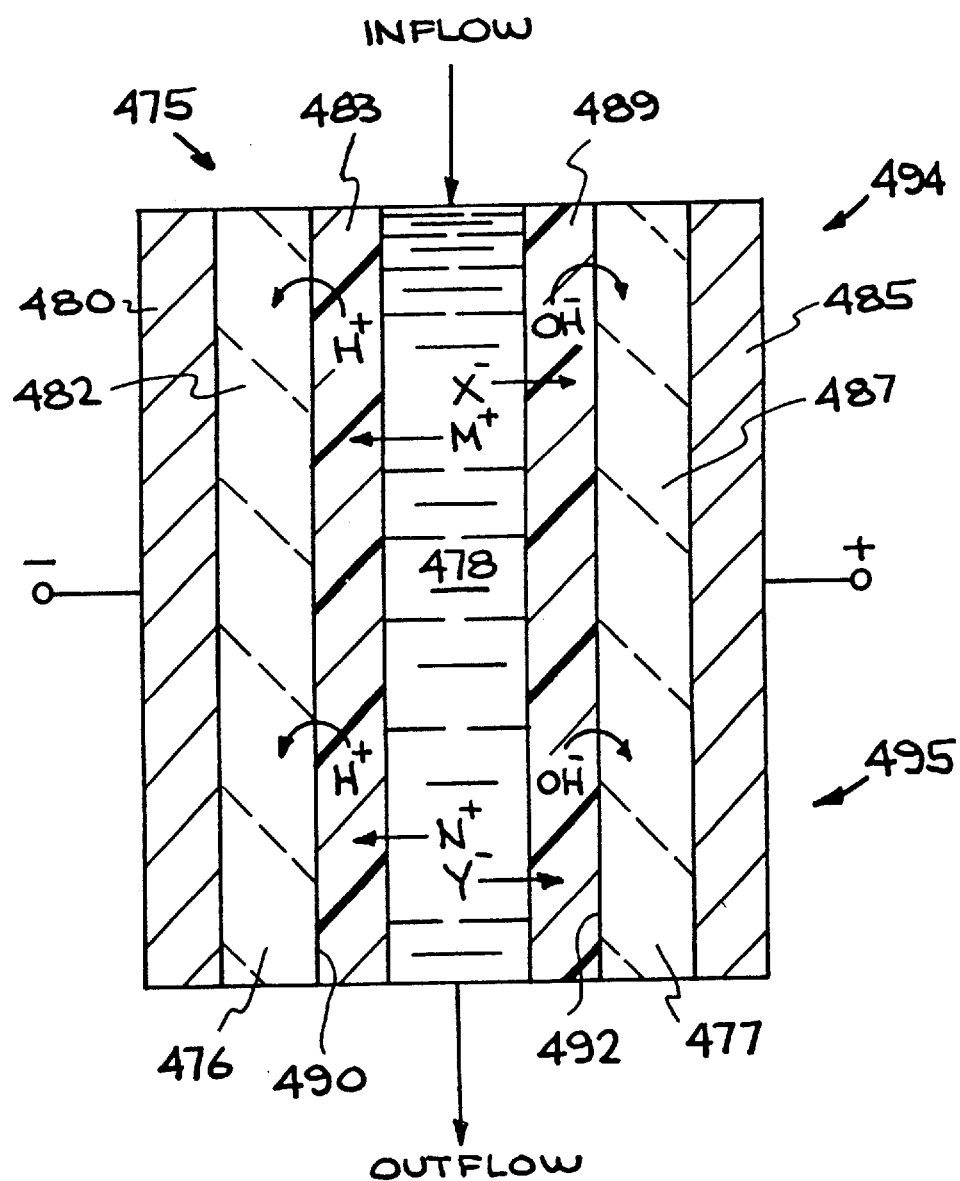
FIG. 22 is a cross-sectional view of another cell including a composite electrode for use in an electrochemically-regenerated ion exchange process.

FIG. 22 shows another cell 475 for use in an electrochemically-regenerated ion exchange (ERIE). Cell 475 includes two composite electrodes 476, 477 that define a central channel 478 therebetween. Cell 475 can also be modified for use with the capacitive deionization systems and cells disclosed herein. For example, the composite electrodes 476, 477 can be readily modified for use in cell 30 (FIG. 3). Moreover, while central channel 478 is illustrated as a straight planar channel, it may assume various shapes and designs, e.g. a serpentine path.

Electrode 476 is a cathode while electrode 477 is an anode. Electrode 476 includes an outer conductive plate 480, an electrosorptive bed 482 and a polymer coating 483. Conductive plate 480 is connected to the negative pole of a D.C. power source. Conductive plate 480 can be replaced by a suitable structural support member, e.g. a dielectric board, substrate, or sheet.

Bed 482 is formed of an electrosorption medium and is bonded to plate 480. Alternatively, bed 482 may be retained against plate 480 by means of coating 483. Bed 482 may be formed of any of the electrosorption media described above, including but not limited to high specific area, porous, conductive, monolithic material (e.g., carbon aerogel composite), porous metal (e.g., titanium or platinum), pack of column powder, reticulated vitreous carbon (RVC) impregnated in resorcinal/formaldehyde carbon aerogel, metallic carbides that can be in the form of powders, particles, foams, sponges, or porous solids (e.g., TiC, ZrC, VC, NbC, TaC, UC, MoC, WC, $MO_2C$, $Cr_3C_2$, $Ta_2C$).

Bed 482 is coated with a suitable cation exchange resin to form coating 483. For example, bed 482 is dip coated in a solution of Nafion. The Nafion solution infiltrates bed 482, and upon drying, it coats the active surface area of bed 482. The cation exchange resin may be selected from a group of polymers having negatively charged functional groups such as sulfonate ($—SO_3^-$), phosphonate ($—PO_3^{2-}$) and/or carboxylate ($—COO^-$). Inorganic cation exchange may also be used. The thickness of the coating 483 is determined by the specific application for which cell 475 is used.

Electrode 477 includes an outer conductive plate 485, an electrosorptive bed 487 and a polymer coating 489. Conductive plate 485 is connected to the negative pole of a D.C. power source, and is generally similar in design and construction to conductive plate 480. Bed 487 is also generally similar in composition and construction to bed 482. Bed 487 is coated with a suitable anion exchange resin to form coating 489. The anion exchange resin may be selected from a group of polymers having positively charged functional groups such as quaternary ($—NR_3$), tertiary ($—NR_2$), and/or secondary ($—NR$) amines. Inorganic anion exchangers may also be used. The thickness of the coating 483 is determined by the specific application for which cell 475 is used.

In use, an aqueous solution with mixture of radionuclides, heavy metals and inorganic salts is flowed through central channel 478 of cell 475. The radionuclides and heavy metals are removed from the flowing stream with similar selectivities as conventional ion exchangers. Chemicals can be employed, flow slowed or stopped, (with or without chemical regenerants) and/or polarizations reversed or shorted during the regeneration of cell 475.

During the polarization of cell 475, protons ($H^+$) migrate from coating 483 to the interface 490 between cation exchange resin coating 483 and bed 482, and are held in the electric double layer formed at interface 490. This proton migration frees active sites on coating 483 for adsorbing cations in the flowing stream. Cations ($M_1^+$ and $M_2^+$, e.g. $Na^+$) migrate into cation exchange resin coating 483 and are held at active sites therein. Simultaneously, hydroxyl ions ($OH^-$) migrate from coating 489 to the interface 492 between anion exchange resin coating 489 and bed 487, and are held in the electric double layer formed at interface 492. This migration of the hydroxyl ions frees active sites on coating 489 for adsorbing anions in the flowing stream. Anions ($X^-$ and $Y^-$, e.g. $Cl^-$, $NO_3^-$, $SO_4^{-2}$, or $CO_3^{-2}$) migrate into anion exchange resin coating 489 and are held at active sites therein.

During discharge (i.e., regeneration) of cell 475, such as by shorting conductive plates 480 and 485 or periodic polarization reversal, resin coatings 483 and 489 are regenerated, and protons and hydroxyl ions are liberated from interfaces 490 and 492, respectively. These protons and hydroxyl ions displace the cations and anions ($M_1^+$, $M_2^+$ and $X^-$, $Y^-$) into a regeneration solution, such as water having the same composition as the feed stream.

Although the present ionization of cell 475 and process of use minimizes, if not completely eliminates, the reliance on chemical regenerants, such regenerants can still be effectively utilized during regeneration in either the stopped-flow mode or the slow-flow mode and further in combination with the shorting of the electrodes or during polarization reversal. Cell 475 can be used for deionizing boiler water for ships and power plants, for fossil-fired and nuclear power plants, for the treatment of mixed and hazardous wastes, for domestic and industrial water softening, for the analysis and treatment of body fluids including blood dialysis, and for several other applications.

Cell 475 also enables the selective, simultaneous separation of cations and ions in a fluid or aqueous solution, with the same selectivity known for the ion exchange resin used as a coating. In the present illustration, this solution contains anions $X^-$ and $Y^-$, and cations $M_1^+$ and $M_2^+$. As the solution starts flowing through central channel 478 certain anions and cations, i.e., $X^-$ and $M_1^+$, respectively, saturate the proximal segment 494 of electrodes 477 and 476. As the resin coatings 489 and 483 in this proximal segment 494 become saturated, the remaining anions and cations, i.e., $Y^-$ and $M_2^+$ begin to saturate the distal segment 495 of electrodes 477 and 476. Ionic selectivities of the ion exchange resins, and hence the electrochemically-regenerated ion exchange (ERIE) process, are established by the relative coulombic attraction between various dissolved ions and the oppositely charged functional groups. The force of attraction is determined by the size, configuration, and charge of both the ions and the functional groups.

Thus this capacitive deionization system and method present significant improvements and advantages over other technologies. For instance, unlike ion exchange, acids, bases, or salt solutions, although optional for improved results, are not required for regeneration embodiments of the system. Regeneration is accomplished by electrically discharging or reversing polarization of the cells as well as providing static or slow-flow conditions. Therefore, no secondary waste is generated. Since no membranes or high pressure pumps are required, the present system offers operational advantages over electrodialysis and reverse osmosis. It is more energy efficient than competing technologies, and is substantially more energy efficient than thermal processes.

The present system can also be used to treat brackish water (800 to 3200 ppm), which is very important, particularly to coastal communities. Competing technologies for the treatment of brackish water are electrodialysis and reverse osmosis. Such typical processes can consume about 7.7 Wh/gal and about 5.3 to 8.5 Wh/gal, respectively. The present system can be much more energy efficient, and may require less than 1 Wh/gal, possibly 0.2–0.4 Wh/gal, depending upon energy recovery, cell geometry, and operation. The theoretical minimum energy for removal of ions from brackish water , based upon thermodynamics, is approximately 0.1 Wh/gal. The present system is more highly efficient and can approach this value.

The system eliminates costly and troublesome membranes. A carbon aerogel CDI system has additional cost advantages over electrodialysis and reverse osmosis since expensive and troublesome membranes are eliminated.

The system also reduces or eliminates wastes from chemical regeneration. A carbon aerogel CDI system could be used for home water softening, the treatment of hazardous and radioactive wastes, the deionization of boiler water for steam and power generation, and the production of ultra pure water for manufacturing. Industrial applications of ion exchange may require 100 pounds of acid for the regeneration of one pound of cation exchange resin, or 100 pounds of base for the regeneration of one pound of anion exchange resin. The present carbon aerogel CDI system uses electrical regeneration at static or slow flow conditions optionally coupled with chemical regenerants, thereby reducing or eliminating the need for such chemical regenerants and the associated wastes.

The present system is simpler and more energy efficient than continuous deionization which requires ion exchange resins, ion exchange membranes, and electrodes. A carbon aerogel CDI system requires only carbon aerogel electrodes. The polymeric ion exchange media used in Continuous Deionization are susceptible to chemical attack during the removal of scale and fouling. Carbon aerogel is resistant to chemical attack.

A carbon aerogel CDI system is superior to beds of activated carbon. Another electrochemical process known as Electric Demineralization, described in U.S. Pat. No. 3,755,135 to Johnson, uses flow-through packed beds of activated carbon as electrodes. However, problems associated with the use of such packed beds prevented the development of a viable commercial product. These problems included the irreversible loss of electrosorption capacity during operation, the relatively low specific surface area of the activated carbon appropriate for use in such flow-through beds, electric potential drop across beds, hydrodynamic pressure drop across beds, bed erosion due to the entrainment of carbon powder in the flowing stream, and the need for porous electrode separators. For illustration, a carbon aerogel CDI system with monolithic carbon aerogel electrodes offers advantages over a CDI system with flow-through packed beds of activated carbon. Slight drops in the electrosorption capacity of carbon aerogel electrodes are almost fully recoverable by periodic potential reversal. Thus, the system capacity can be maintained at a high level. Since the specific surface area of carbon aerogel (600–1000 $m^2/gm$) is significantly greater than that of activated carbon powder appropriate for use in a flow-through packed bed (230 $m^2/gm$ or 200–300 $m^2/gm$), a greater quantity of salt can be electrosorbed on carbon aerogel than on a comparable mass of activated carbon powder [A. M. Johnson, J. Newman, J. Electrochem. Soc. 118, 3 (1971) 510–517].

It has been experimentally demonstrated that in a CDI process having 384 pairs of carbon aerogel electrodes (768 individual electrodes) and a total activated surface area of $2.4 \times 10^6$ ft2 ($2.2 \times 10^9$ $cm^2$), less potential drop occurs in a thin sheet of carbon aerogel than in a relatively deep bed of activated carbon. Consequently, more ions can be electrosorbed on a unit of carbon aerogel surface area than on a comparable unit of activated carbon surface area. In deep packed beds of carbon, the potential can drop to levels where the electrosorption process is not very effective. Immobilization of the carbon in the form of aerogel has made it possible to construct systems that do not require porous membrane separators. Unlike activated carbon powder, monolithic sheets of carbon aerogel are not entrained in the flowing fluid stream. Water passes through open channels between adjacent anodes and cathodes, experiencing only a modest pressure drop of about 30 psi or less. In contrast, flow through a packed bed of activated carbon with comparable surface area experiences a significantly greater pressure drop $\geq 1000$ psi.

The CDI system has a simple, modular plate-and-frame cell construction. Electrochemical cells required for Continuous Deionization and Electric Demineralization are complicated by the need for particulate ion exchange resin and activated carbon, ion exchange membranes, electrode separators, and electrodes. The present CDI system requires simple, double-sided planar electrodes. Double-sided electrodes are made by gluing two sheets of the carbon aerogel composite to both sides of a titanium (or other equivalent metal-containing) plate that serves as both a current collector and a structural support. Conductive silver epoxy can be used for gluing. In one embodiment, the carbon aerogel composite has a very high specific surface area of $2.9$–$4.9 \times 10^6$ $ft^2/lb$ (600–1000 $m^2/gm$). Each sheet is 2.7 in$\times$2.7 in$\times$0.005 in (6.86 cm$\times$6.86 cm$\times$0.0125 cm) and has a total active surface of approximately 3,014 $ft^2$ ($2.8 \times 10^6$ $cm^2$). Two orifices are located along one side of the carbon aerogel electrode and admit water to the electrode gap. A pattern of holes are located around the perimeter of the titanium plate and accommodate 12 threaded rods that hold the cell stack together. The assembly of these components into a capacitive deionization cell is also very simple. The electrodes and headers are aligned by the threaded rods. An electrode separation of 0.02 in (0.05 cm) is maintained by cylindrical nylon spacers concentric with the threaded rods and a rubber compression seal. Even electrodes serve as cathodes while odd electrodes serve as anodes. Since the orifices in each electrode normally alternate from one side of the stack to the other, the flow path through the stack is serpentine. An experimental capacitive deionization cell configuration includes 384 pairs of carbon aerogel electrodes with a total active cathodic (or anodic) surface area of approximately $2.4 \times 10^6$ ft$^2$ ($2.2 \times 10^9$ cm$^2$). However, the system can be expanded to accommodate any desired concentration gradient across the stack, as well as any flow rate. Scale-up or scale-down for capacity and concentration can be readily accomplished.

The present CDI system uses materials, such as carbon aerogel, that are easy to make and commercially available. Monolithic sheets of this material can be made by infiltrating a resorcinol-formaldehyde solution into a porous carbon paper, curing the wetted paper between glass plates in a closed vessel, and then carbonizing in an inert atmosphere. This fabrication process results in unique open-cell carbon foams that have high porosities, high specific surface areas (600–1000 m$^2$/g), ultrafine cell and pore sizes ($\leq$50 nm), and a solid matrix composed of interconnected colloidal-like particles (fibrous chains) with characteristic diameters of 10 nm. The porosity and surface area of aerogels can be controlled over a broad range, while the pore size and particle size can be tailored at the nanometer scale.

The present capacitive deionization system uses materials, such as carbon aerogel, that are resistant to chemical attack. Fouling and scale formation are inevitable in process equipment used for desalination. Aggressive chemical treatments are required for rejuvenation. Therefore, it would be desirable to construct the capacitive deionization system out of materials that can withstand such chemical treatments. Carbon aerogel is relatively resistant to many of the chemicals now used for scale control, such as HCl. Unlike polymeric membranes and resins, carbon aerogel is also resistant to dissolution by organic solvents. Oxidants such as chlorine attack polyamide reverse osmosis membranes, but do not appear to be a significant problem in carbon aerogel systems. Similar problems are encountered with electrodialysis and Continuous Deionization.

The present capacitive deionization system has a fully-automated potential-swing operation. The Electric Demineralization process was operated in batch mode with no energy recovery. Capacitive deionization can, for instance, produce a continuous flow of product water by operating two stacks of carbon aerogel electrodes in parallel. One stack purifies while the other is electrically and/or chemically regenerated, preferably in the stopped flow or slow-flow modes with accompanying fast flushing. This mode of operation is referred to as "potential swing" and also enables energy recovery. For example, energy released during the discharge of one stack of electrodes (regeneration) can be used to charge the other stack (deionization). Such synchronous operation requires user-friendly automation.

One exemplary application of the present invention includes the design and manufacture of a deionization system for purifying radioactive water. For instance, one embodiment of the present system could be used to purify the waste water generated from washing fuel assemblies coated with metallic sodium residuals. The 500 gallons of waste water currently generated during the washing of each assembly include approximately 200 ppm sodium, trace quantities of other metals, trace quantities of some non-metal that can be removed by filtration, and trace quantities of radioactive constituents (primarily fuel cladding corrosion products). Grade B water purity would have to be achieved so that water could be recycled; (i.e., conductivity less than 20 microsiemens/cm).

Figure 23:
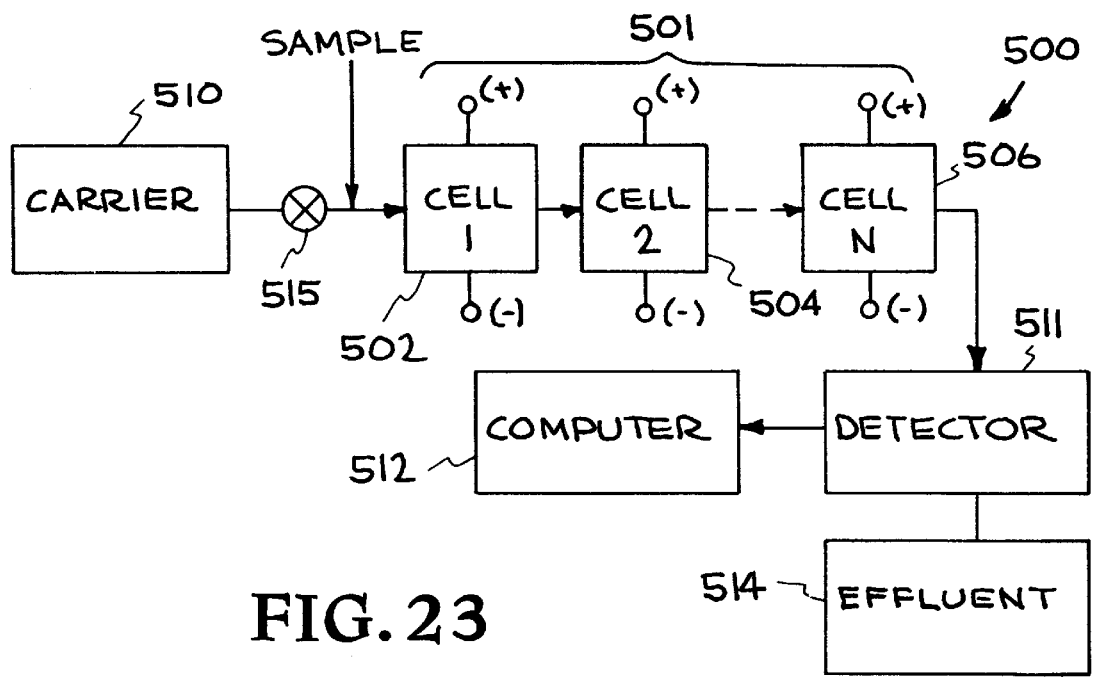
FIG. 23 is a block diagram of a first embodiment of an electrosorptive ion chromatograph.

FIG. 23 shows an electrosorptive ion chromatograph (EIC) 500 which can be used for analysis, treatment and processing of various fluids and/or aqueous solutions containing a variety of anions and cations. A carrier tank 510 and a pump 515 for drawing the carrier (e.g., deionized water) are connected to chromatograph 500 which includes a column 501, a detector or conductivity sensor 511, and a computer system 512. The solution at the output of detector 511 is collected in an effluent tank 514.

Unlike conventional ion chromatography where anions are analyzed with a column of anion exchange resin and cations with a column of cation exchange resin, EIC 500 can simultaneously analyze both anions and cations in a single column 501 that may include one or a series of electrochemical cells 502, 504, 506. Column 501 replaces conventional ion exchange columns with packing material. Furthermore, the selectivity of EIC 500 can be readily changed by altering the potential between the anodes and cells 502–506, compared with conventional ion chromatographs where selectivity is manipulated by changing the columns of ion exchange resin or the carrier.

In use, a sample is injected into a carrier stream from carrier tank 510, and passes through the single or series of cells 502–506. Each cell generally includes a pair of porous electrodes, i.e., an anode and a cathode. These cells have an anode and/or a cathode constructed according to the present invention. The electrodes are polarized, and draw ions from the flowing stream to the surface of the porous electrodes where they are held in the electric double layers.

Figure 26:
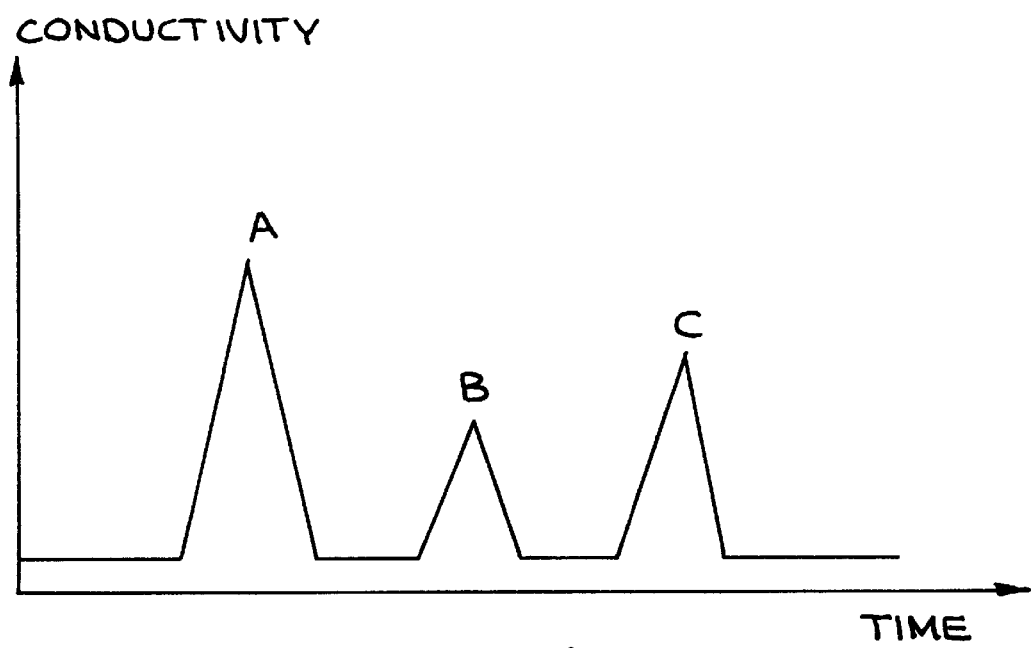
FIG. 26 is a conductivity-time graph representing the elution of three species A, B and C separated by the chromatograph of FIG. 23.

Each species of cation and anion has a different affinity for the porous electrodes, and has a characteristic elution time in the cells 502–506. The elution time can be used as a basis for identifying the ions. A conductivity sensor 511 or another type of detector at the output of exchange column 501 is used to detect ions as they leave column 501. The concentration of the ions is proportional to the area under the conductivity-time (concentration-time) peak. FIG. 26 illustrates three conductivity-time (concentration-time) peaks for three different ionic species A, B, C.

Computer system 512, with an analog-to-digital converter is connected to detector 511 to process data and to generate reports.

FIGS. 24 and 25 illustrate a single cell 502. In certain applications column 501 may include a single long cell. Cell 502 generally includes a hollow open-ended vessel 520 which allows the sample stream to flow therethrough in the direction of the arrows INFLOW, FLOW and OUTFLOW. In FIG. 25, vessel 520 has a rectangular cross section; however, the cross section of vessel 520 can have other shapes, as shown in FIG. 27.

A thin sheet 524 of high specific area, porous, conductive, monolithic material (e.g., carbon aerogel composite) is bonded to the inner surface of one side of cell 502. In one embodiment, sheet 524 is glued to cell 502 with an electrically conductive epoxy. Conductive sheet 524 is substantially similar in composition to sheet 44 shown in FIG. 4A.

Sheet 524 may also be bonded to at least part of the remaining three sides of cell 502. Sheet 524 may be coated with a coating (not shown) similar to that described in FIG. 22. Sheet 524 is connected to one pole of a D.C. power source to form an electrode. Another thin conductive sheet 526 has a similar composition to that of conductive sheet 524, and is bonded to the opposite, or another side of cell 502. Sheet 526 is connected to the other pole of the D.C. power source to form an electrode.

Figure 28:
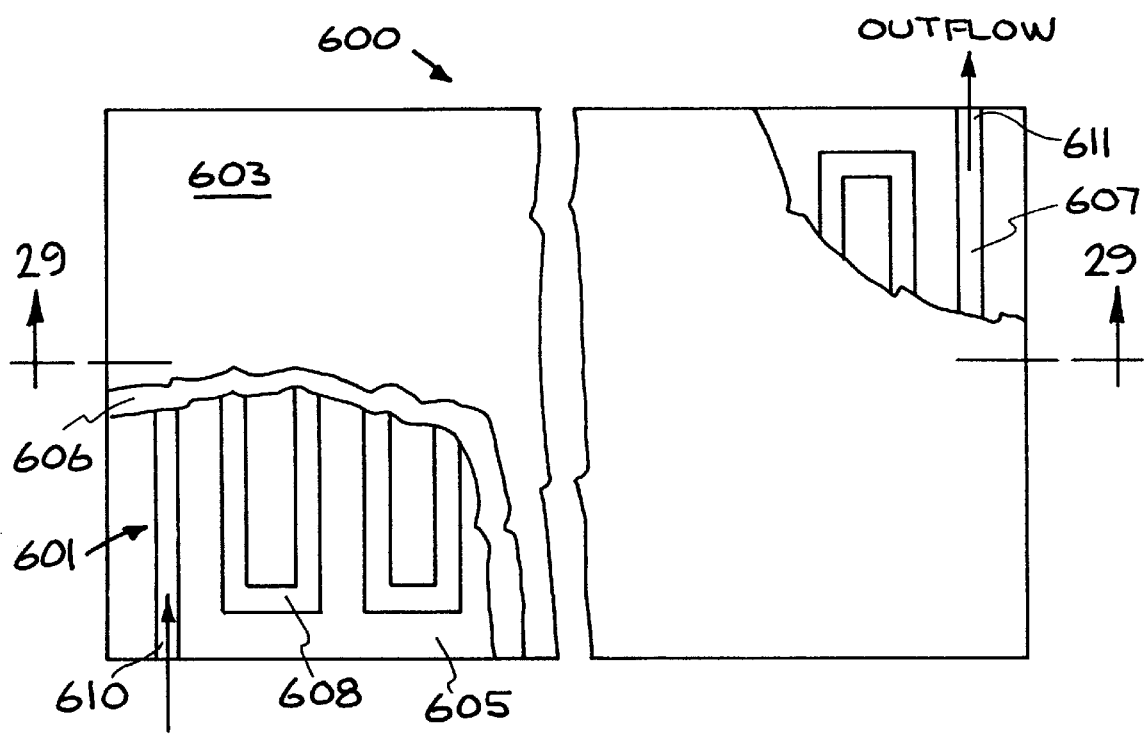
FIG. 28 is a fragmentary, top plan view of another embodiment of a cell used in a chromatograph.
Figure 29:
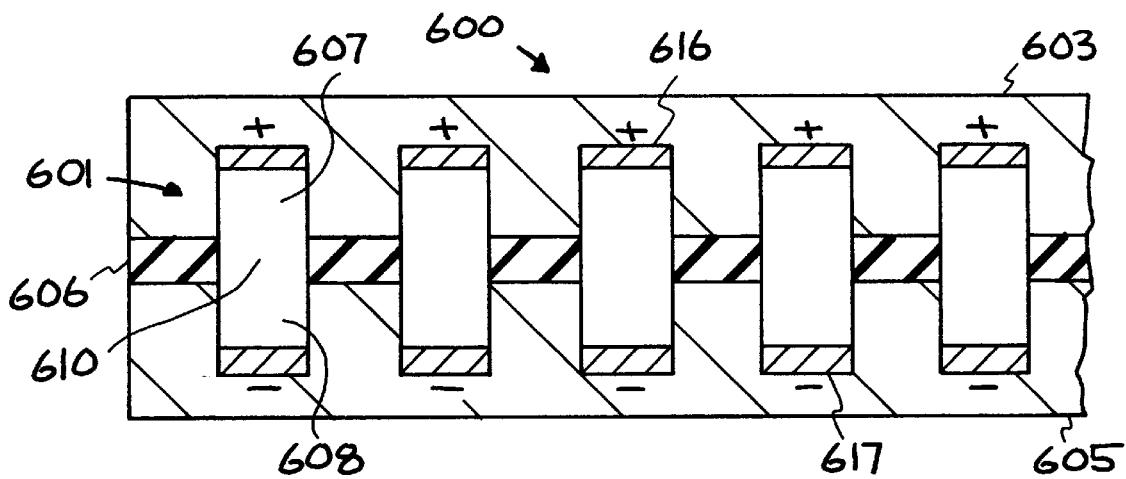
FIG. 29 is an enlarged cut away, cross sectional view of the cell of FIG. 28, taken along line 29—29.

Vessel 520 and sheets 524, 526 define a central channel 530 within cell 502, through which the sample stream flows. In one embodiment, channel 530 is very narrow so as to minimize the amount of the sample needed. In this example, channel 530 is straight; however, as shown in FIGS. 28 and 29, channel 530 can have other shapes, e.g. a serpentine pathway.

The general principle of operation of cell 502 has been explained above in relation to the capacitive deionization cells and systems. As the sample stream, which includes the carrier and the sample to be analyzed or processed, passes through the first cell 502, a voltage is applied across anode 524 and cathode 526, which causes the various ions in the sample to be eluted at different rates. Consequently, the species are separated.

FIG. 26 shows three species A, B and C. Species C interacts with electrodes 524, 526 to a greater extent than species A and B, and therefore, species C is retarded to a greater extent than species A and B. The extent of interaction between the species and electrodes 524, 526 is described in terms of an adsorption or electrosorption isotherm and is quantified in terms of an equilibrium constant "K" which can be controlled by varying the electrode material and the available electrode surface area available for adsorbing or interacting with the ions, to control the travel time of the species.

A significant advantage of the present chromatograph 500 is that the interaction between the ionic species and the electrodes 524, 526 is an electrostatic coulombic attraction rather than a chemical interaction. The degree of integration and the elution time can be controlled by simply changing the voltage between the anode and the cathode. In conventional ion chromatography, columns have to be changed to alter the degree of interaction.

Furthermore, the present chromatograph 500 enables the use of a single column 501 for simultaneous anionic and cationic types of chromatography. Conventional ion chromatography requires that different columns be used. Additionally, this new chromatograph 500 can be used for separating and processing biological cells, molecules and other matter without damage since the sample stream flows freely along channel 530. Chromatograph 500 can control the elution time of various species being analyzed, and has a reduced overall cost of manufacture, operation and maintenance because of the ability to combine and implement the anionic and cationic separation processes within a single column 501.

In another embodiment, the voltage gradient across electrodes 524, 526 is varied, so that the voltage is modulated or pulsed or is programmed to a desired pattern. As a result, the elution time of the species being analyzed can be varied, so as to minimize overlap between the conductivity-time graphs of the species. In other words, by varying the elution times of the species, the separations between the various peaks on detector 511 are increased, thus making it easier to distinguish and analyze the species.

In yet another embodiment, an ion selective electrode is used as part of cell 506, in addition to detector 511. This ion selective electrode is preferentially sensitive to specific ions, and may be formed of electrochemical cells from various forms of polarography, cyclic voltammetry, X-ray fluorescence, spectroscopy such as V, visible, vibrational, infrared.

FIG. 27 is a cross sectional view of cell 502 taken along line 25—25, and represents another design of cell 502. In this example, cell 502 is generally cylindrically shaped and has a generally circular section. Four electrodes 540–543 having similar composition to that of electrodes 524, 526, are bonded to the inner surface of a vessel 545, and are separated by four suitable insulation dividers 546–549. Each of these electrodes 540–543 is connected to a corresponding pole of the power source. As shown, electrodes 540, 541 act as anodes, while electrodes 542, 543 act as cathodes. The voltage gradient across one electrode pair (e.g., 540, 542) can be different from the voltage gradient across the other electrode pair (e.g., 541, 543). A cylindrical geometry would be advantageous for applications where high pressure operation is required.

FIGS. 28 and 29 illustrate a column cell 600 which operates pursuant to the same principles as cell 502 but differs with respect to the shape of the internal channel. While central channel 530 (FIG. 24) is straight, cell 600 defines a serpentine channel 601 through which the sample stream flows. Channel 601 is made as narrow but as long as possible, providing a long flow path in a small space, in order to minimize the amount of sample needed.

Cell 600 generally includes two oppositely disposed, substantially flat plates or substrates 603, 605 that are separated by an insulation layer 606 of a predetermined thickness. The first plate 603 includes a serpentine trough 607, and the second plate 605 includes a similar serpentine trough 608, such that when both plates 603, 605 are connected together, troughs 607, 608 and part of insulation layer 606 form channel 601, which defines a serpentine pathway. Channel 601 has a single inlet 610 and a single outlet 611 for the sample stream.

A thin conductive sheet 616 has a similar composition to that of conductive sheet 524 (FIG. 24), and is bonded to the inner surface of trough 607. A similar conductive sheet 617 is bonded to the inner surface of trough 608. These conductive sheets 616, 617 are connected to the poles of the D.C. power supply.

The teachings described herein, particularly as to the chromatograph columns, can also be used to design an electrochemical intensifier or concentrator. An electrochemical intensifier is a device used to concentrate dilute ionic solutions for subsequent measurement by any of a variety of analytical techniques, such as ion chromatography, ion selective electrodes, differential pulse polarography.

Figure 30:
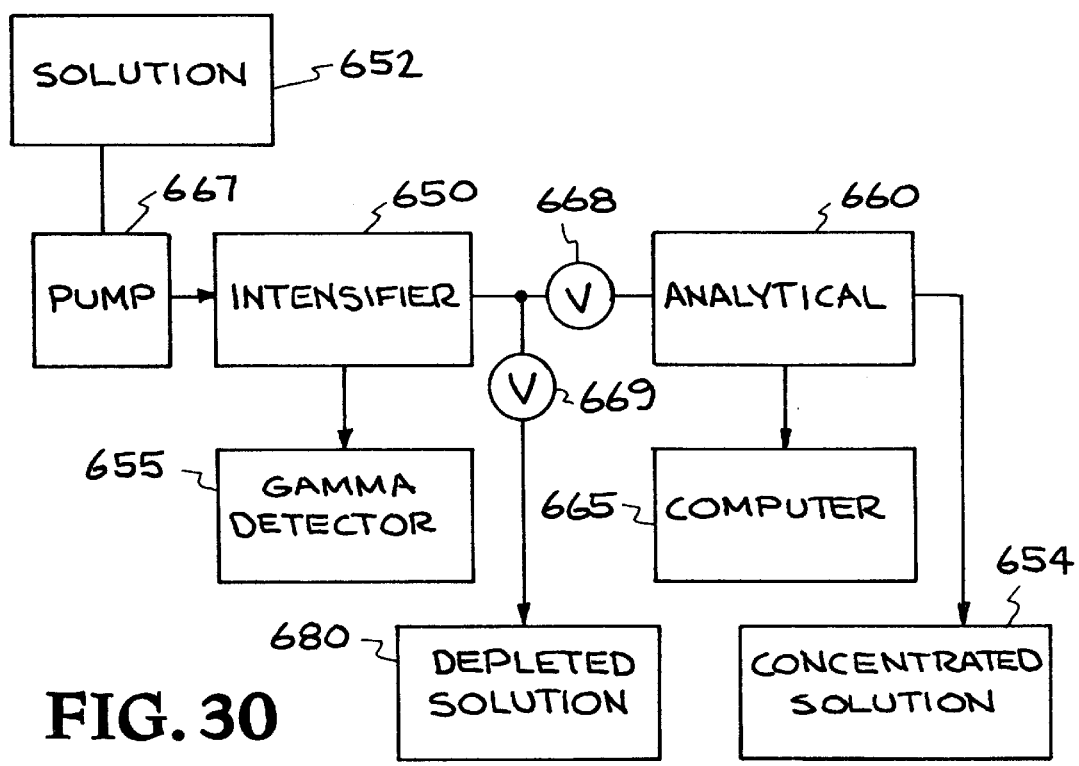
FIG. 30 is a block diagram of an intensifier.

An intensifier 650, illustrated in FIG. 30, generally includes a cell similar to the cells described above for the chromatographs. The porous anodes and cathodes remove ions from a relatively dilute solution 652 during a capacitive charging phase. Ions are removed from the dilute solution under the force of an imposed electric field (cell voltage gradient) and held in the double layers formed at the surfaces of the electrodes. Subsequently, ions are collected in a more concentrated solution 654 during a capacitive discharging or regeneration phase. The capacitive charging and discharging phases are as described above in relation to the CDI systems, cells and methods.

The species that are present in the dilute solution at levels below the detection limit of a particular analytical technique can be concentrated to a level where they become detectable. If the ions are radioactive, they can be measured as they accumulate on the porous electrodes. Similarly, X-ray fluorescence can be used to monitor heavy metals, or like materials, that accumulate on the electrodes. A gamma ray detector 655 may be used to monitor the radiation of radioactive material that accumulates on the electrodes or in the concentrated solution 654. An analytical or measurement instrument 660 is connected to the effluent solution at the output of intensifier 650, and is further connected to a computer 665 which processes the accumulated data and controls the operation of intensifier 650, a pump 667 that draws the dilute solution 652 into intensifier 650, a valve 668 that controls the flow of the effluent solution from intensifier 650 to the analytical instrument 660, and a valve 669 that controls the flow of the effluent to a tank 680 for storing the solution that has been depleted of ions or deionized by intensifier 650.

Figure 32:
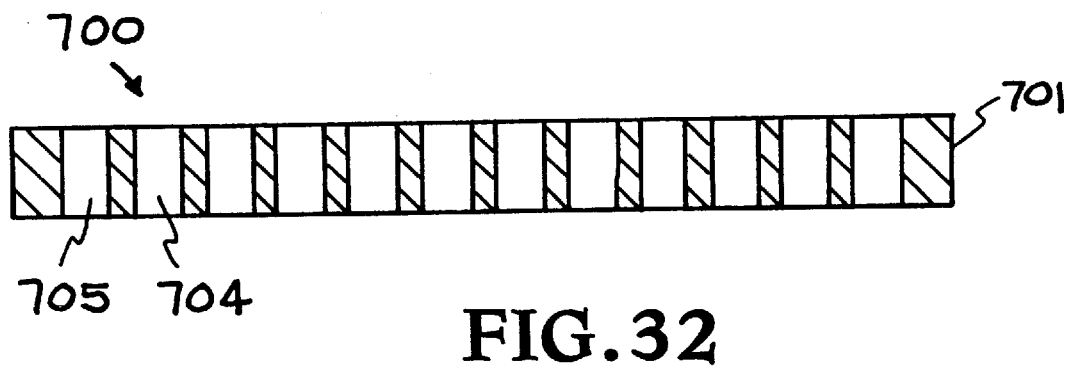
FIG. 32 is a cross-sectional view of the electrode 700 of FIG. 31 taken along line 32—32.
Figure 31:
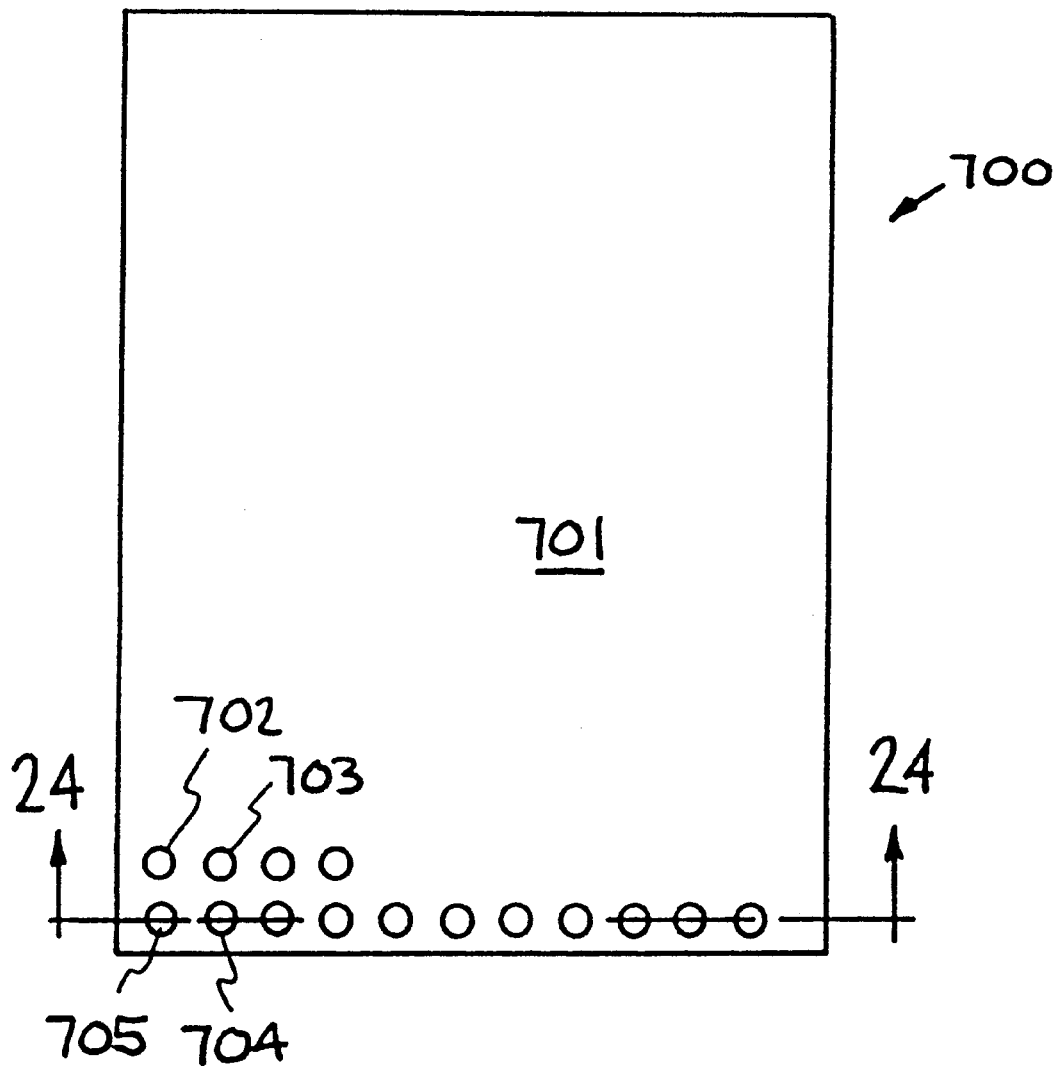
FIG. 31 is an isometric view of a single, monolithic, thin film electrode made by photolithography.

FIGS. 31, 32 show a single, monolithic, thin film electrode 700 made by photolithography. Electrode 700 has a very high specific surface area and may replace the various electrodes described above. For example, electrode 700 may replace electrode 44 (FIG. 4A), electrodes 253, 254 (FIG. 11B), electrode 314 (FIG. 15), electrode 357 (FIG. 17), electrodes 419, 420 (FIG. 19), electrodes 465, 466 (FIG. 21), beds 482, 487 (FIG. 22), sheets 524, 526 (FIG. 24), electrodes 540–543 (FIG. 27), and sheets 616, 617 (FIG. 29).

Electrode 700 is shown as a thin, flat, porous sheet, screen or film 701 made of any conductive metal, e.g., titanium, copper, platinum, tungsten, iridium, nickel or silver. The metal is selected to be corrosion resistant to the solution being processed. Using conventional photolithography, an array of very fine holes, i.e., 702–705 is formed on one surface of film 701. While only four holes 702–705 are shown, many more holes may be formed across the entire surface of film 701. It would be desirable to optimize the number of holes so as to increase the surface area of film 701. In one example, the diameter of one hole is about 0.1 micron, and film 701 will have a density of about $10^{10}$ holes per $cm^2$. If film 701 has a depth of about 25 microns, and holes 702–705 were to penetrate through most of the thickness of film 701, the volumetric specific surface area of film 701 would be about 64 $m^2/cm^3$. If the electrode includes a stack of ten (10) films, the volumetric specific surface area of the electrode would be about 640 $m^2/cm^3$, which is comparable to that of a carbon aerogel electrode.

In an electrode 700 comprised of a single film 701, holes 702–705 may or may not extend through film 701. While film 701 is shown as a thin flat screen, it can assume various configurations. Holes 702–705 can be cylindrical with a circular cross-section, square, or of any desired shape. Alternatively, holes 702–705 may be etched interconnected grooves.

Figure 33:
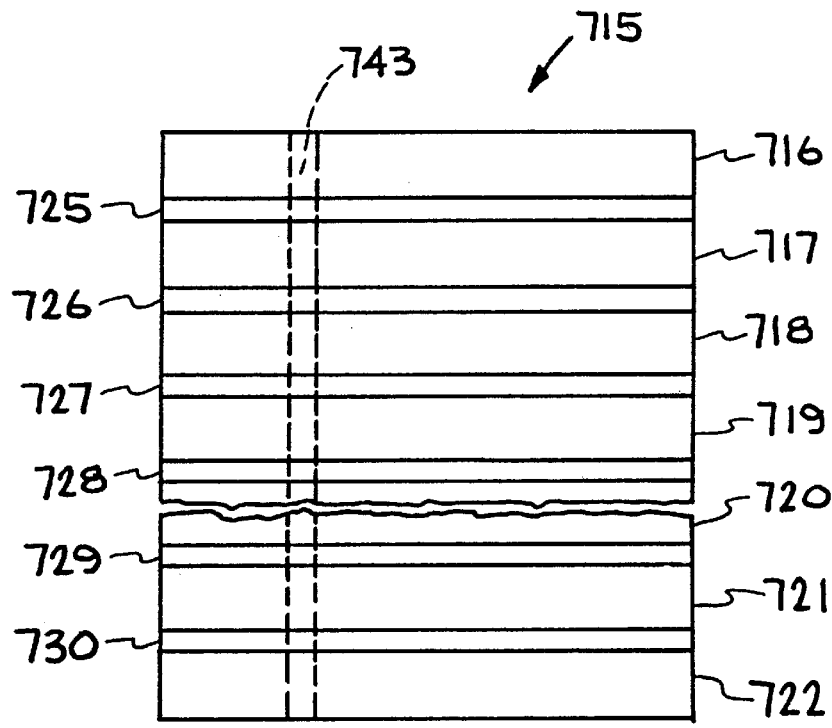
FIG. 33 is a side elevational view of another electrode.

FIG. 33 shows another electrode 715 which includes a stack of generally identical films 716–722, that are alternately interleaved with a stack of spacers 725–730. Films 716–722 are porous, and have a similar construction to film 701 (FIG. 31). In order for the solution to infiltrate through the stack of films 716–722, the holes, as illustrated by a single hole 734, extend through the entire depth of films 716–722. Spacers 725–730 are thin and porous, and can be metallic or nonmetallic. In one embodiment, spacers 725–730 consist of filter papers.

It is possible to select the number of films forming electrode 715 such that the volumetric specific surface area of electrode 715 approaches that of a carbon aerogel electrode, and in certain applications, it is possible to replace the carbon aerogel electrode. An additional advantage of the present electrode design is that it is now possible to accurately regulate the desired volumetric specific area of the electrode, by either increasing or decreasing the number of constituent films. The films described in FIGS. 31–33 are also referred to as graphic sheets.

Figure 34:
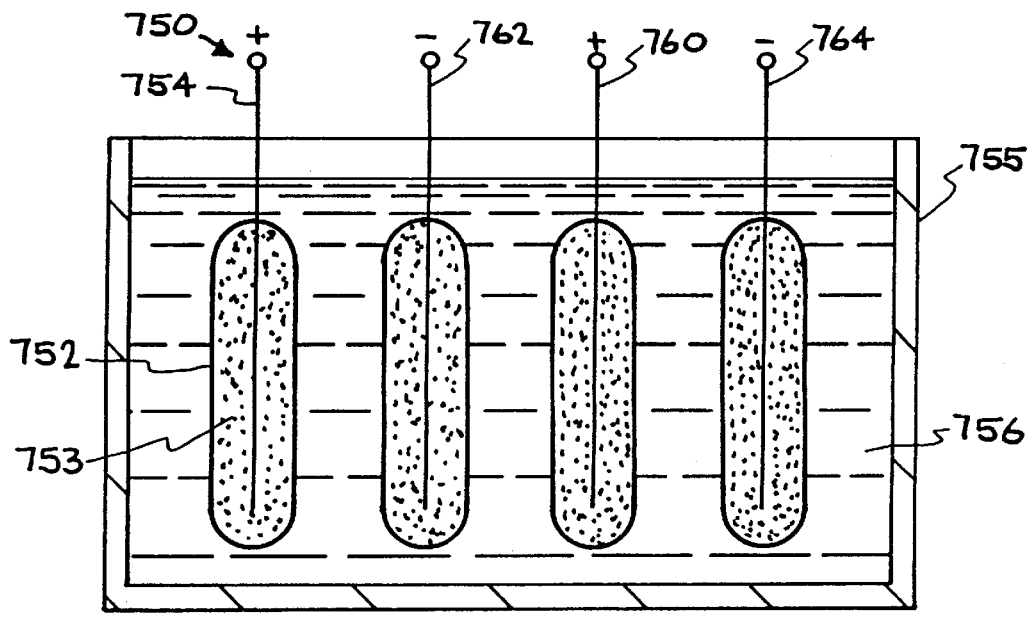
FIG. 34 is a schematic view of a tea bag electrode.

FIG. 34 shows yet another embodiment of an electrode 750 called a tea bag electrode. Electrode 750 includes a closed dielectric (ion conductive or ion exchange) or porous,, flexible, bag 752 that contains and restrains an electrically conductive material 753. Conductive material 753 may be any conductive powder, and in particular any one of the conductors listed herein, for example carbon aerogel. An electrical conductor or wire 754 extends inside bag 752 in contact with conductive material 753. When in use, wire 754 is connected to one pole of a D.C. power source.

In use, a single tea bag electrode 750 is dropped in a container 755 containing a fluid 756 to be processed or analyzed. In this most basic example, electrode 750 is positively charged and acts as an anode, while container 755 is negatively charged and acts as a cathode. As explained above with respect to the various CDI systems and cells, electrode 750 electrosorbs the anions contained in fluid 756 inside bag 750.

Once a desired ionic concentration is reached, bag 752 is removed from fluid 756 and processed. In one example, the concentrated ions are hazardous and bag 752 is disposed of. In another example, the concentrated ions captured within bag 752 can be released, analyzed and processed. Therefore, electrode 750 can have several uses, including but not limited to capacitive deionization and ion concentration.

Two or more tea bag electrodes of the same polarity can also be used, with the container having the opposite polarity. The container can be electrically neutral and several tea bag electrodes 750, 760 act as anodes, while other tea bag electrodes 762, 764 act as cathodes. In this particular illustration the anodes and cathodes are interleaved; however, the anodes and cathodes can be placed in a variety of different arrangements. For example, the anodes may be arranged along an outer circular pattern, while the cathodes may be arranged in a coaxial inner circular pattern. In another example, the container may be negatively charged, and used as a cathode with the concentric circular patterns described in the latter example. Other patterns may also be selected. While the number of anodes and cathodes may, in many applications, be the same, this equality is not always required.

Figure 35:
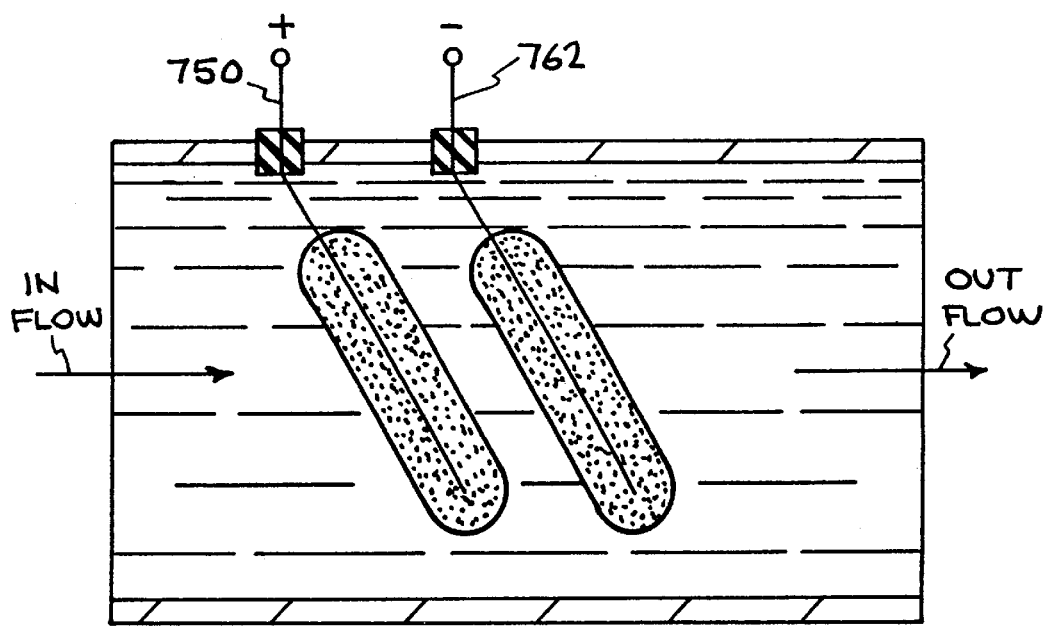
FIG. 35 illustrates a pair of tea bag electrodes of FIG. 34 placed in a fluid stream within a vessel.

FIG. 35 illustrates a pair of tea bag electrodes 750, 762 placed in a fluid stream within a vessel or pipe for sampling the fluid stream. This sampling can take place periodically, at predetermined or programmed time intervals, by the controlled application of a voltage across electrodes 750, 762.

Figure 36:
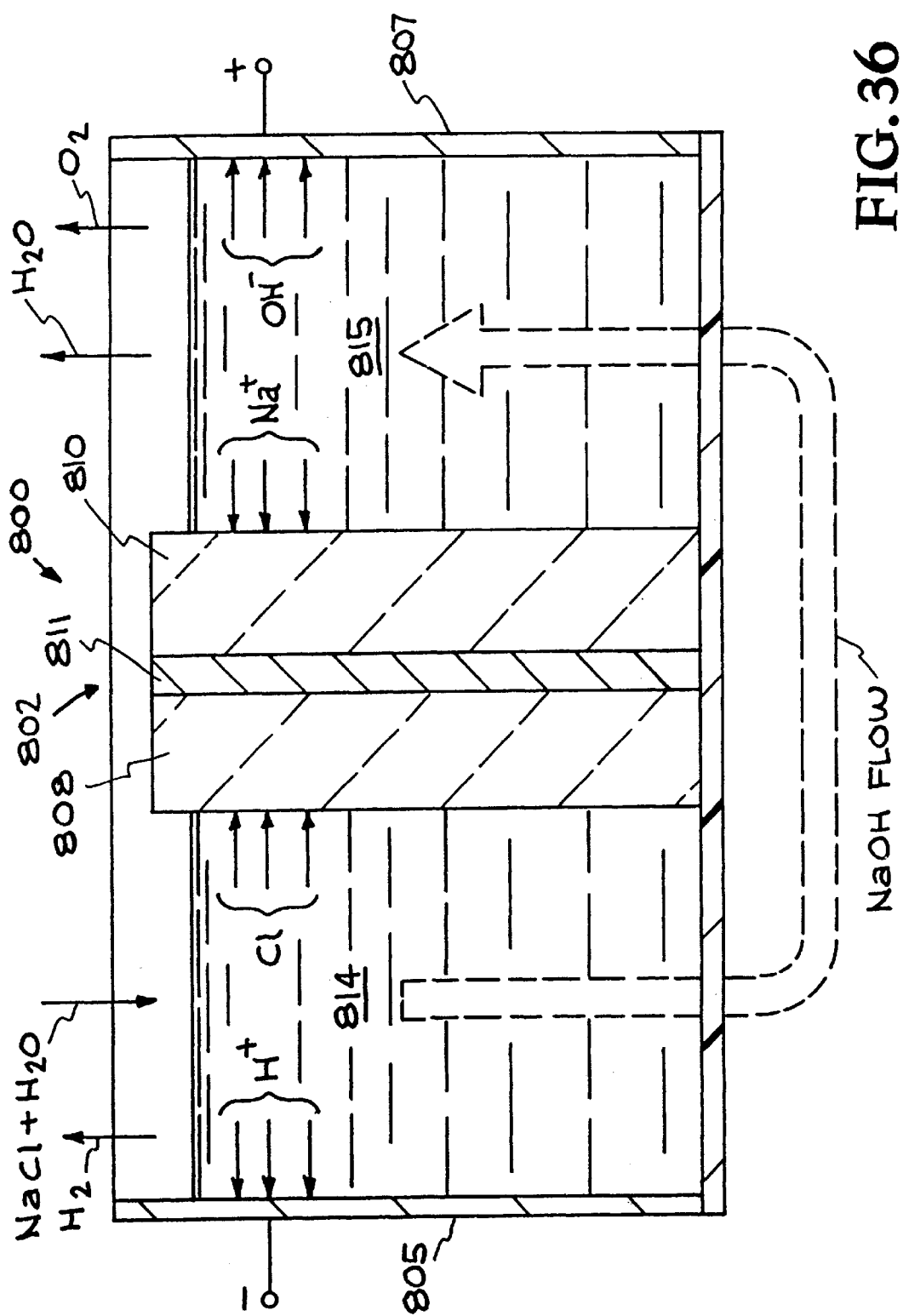
FIG. 36 is a schematic sectional view of an electrophoresis cell.

FIG. 36 shows an electrodialysis cell 800 which includes a bipolar electrode 802 disposed intermediate a cathode 805 and an anode 807. Bipolar electrode 802 includes two films, screens, plates, etc. 808, 810 disposed on either side of a conductive barrier 811. Films 808, 810 can be any high specific surface area material, similar to the materials described above, for instance, carbon aerogel or porous carbon. Bipolar electrode 802 acts as a central divider and defines a cathode compartment 814 and an anode compartment 815.

In use, the electrical current flows from anode 807, through anode compartment 815, through bipolar electrode 802, through cathode compartment 814, toward cathode 805. For illustration purpose only, the fluid, solution or electrolyte to be processed by cell 800 is salt or sea water (NaCl and $H_2O$). The solution flows from cathode compartment 814 to anode compartment 815 in the direction of the arrow shown in broken lines.

Within cathode compartment 814, the electrode reaction at cathode 805 is hydrogen ($H_2$) evolution, while the chloride ions ($Cl^-$) precipitate toward bipolar electrode 802 and are electrosorbed by film 808. This results in an alkaline solution of sodium hydroxide (NaOH), which then flows to anode compartment 807, where the sodium ions ($Na^+$) precipitate toward bipolar electrode 802 and are electrosorbed by film 810. The electrode reaction at anode 807 is oxygen ($O_2$) evolution. The effluent solution consists of purified, desalted water ($H_2O$).

An important advantage of cell 800 is that the salt, i.e., NaCl, or various radioactive salts, can be removed from the solution and immobilized or stored within bipolar electrode 802. In one embodiment, bipolar electrode 802 may be removed and disposed of. In another embodiment, bipolar electrode 802 may be removed to a different location and regenerated. In yet another embodiment, conductive barrier 811 is removed, and the cations, i.e., sodium ions (Na+) and the anions, i.e., chloride ions (Cl−), form a salt, i.e., sodium chloride (NaCl), which precipitates on the porous films 808, 810, and which is then removed and either disposed of, or processed further.

The foregoing applications may be particularly important in the treatment of radioactive wastes. For instance, the radioactive salts, such as $CsCl(^{137}Cs)$, may be caused to precipitate on carbon aerogel films 808, 810. The volume of these films 808, 810 can then be significantly reduced by crushing them, or by oxidizing the carbon to form carbon dioxide.

Figure 37:
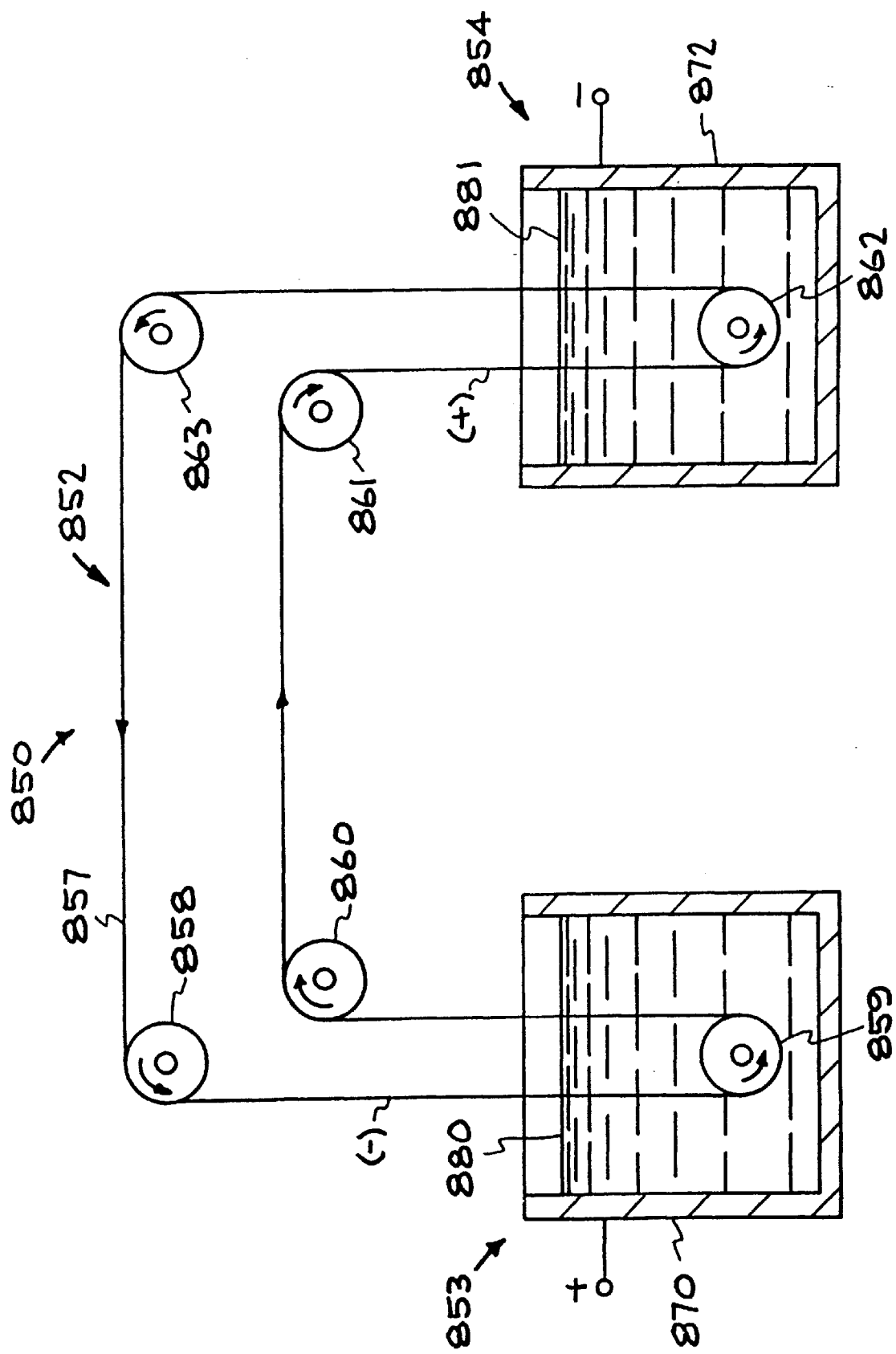
FIG. 37 is a schematic view of a capacitive deionization system using a moving electrode.

FIG. 37 is a schematic view of a capacitive deionization system 850 employing a moving electrode 852. The capacitive deionization system 850 generally includes moving electrode 852 that travels between an anode cell 853 and a cathode cell 854. Moving electrode 852 includes a conductor 857 such as a wire, sheet, fluidized beads, which is supported by, and moved by a plurality of wheels 858–863. Anode cell 853 includes a container 870 that is held at a positive potential relative to conductor 857 of moving electrode 852. Cathode cell 854 includes a container 872 that is maintained at a negative potential relative to conductor 857. As an example, the potential difference between the anode container 870 and the moving conductor 857 is about 1.2 volts, while the potential difference between the cathode container 872 and the moving conductor 857 is about 1.2 volts.

In this particular example, anode cell 853 contains a solution or fluid 880 to be processed; however, in other applications, the solution may be contained in cathode cell 854.

In operation, the electrical current passes from container 870, through fluid 880, to conductor 857. Consequently, the positively charged ions in the solution 880 move to conductor 857 and are electrosorbed thereon. These ions will be carried along conductor 857 into cathode cell 854, where the electrosorbed positive ions are drawn toward the negatively charged container 872, and are released from conductor 857 into solution 881.

One advantage of CDI system 850 is that the required actual surface area of moving electrode 852 does not need to be relatively high, i.e., not as high as that of carbon aerogel.

It is possible to increase the surface area that solution 880 sees per unit time, by increasing the velocity of the moving electrode 852. As a result, it is now possible to perform processes such as CDI without a high porosity electrode.

COMMERCIAL APPLICATIONS

By using the cells and systems according to the present invention, it is possible to remove the following and other impurities and ions from fluids, including body fluids, and aqueous streams, and to subsequently regenerate the cells:

1. Non oxidizable organic and inorganic anions. Inorganic anions include: $OH^-$, $Cl^-$, $I^-$, $F^-$, $NO_3^-$, $SO_4^{2-}$, $HCO_3^-$, $CO_3^{2-}$, $H_2PO_4^-$, $HPO_4^{2-}$, and $PO_4^{3-}$. In this case, the operative mechanism is electrostatic double layer charging. For this purpose, it would be desirable to maintain the terminal potential across the electrodes lower than that required for electrolysis of the solvent in order to avoid gas evolution. The optimum potential is in the range between 1.0 and 1.2 volts, relative to the normal hydrogen electrode (NHE). In general, the recommended range of potential for water treatment lies between 0.6 and 1.2 volts.

2. Non reducible cations, such as $Li^+$, $Na^+$, $K^+$, $Cs^+$, $Mg^{++}$, $Ca^{++}$. Here too the operative mechanism is electrostatic double layer charging.

3. Reducible cations, such as: $Cu^{++}$, $Fe^{++}$, $Pb^{++}$, $Zn^{++}$, $Cd^{++}$. In this case, the operative mechanism is electrodeposition.

4. Reducible anions.

5. Colloidal particles such as bacteria, viruses, oxide particles, dirt, dust. In this case, the operative mechanism is electrophoresis.

6. Chemisorption of organic molecules onto the carbon composite electrode 44. This adsorption process might be relatively irreversible. Regeneration in this case would involve the use of strong oxidants, such as hydrogen peroxide, for the purposes of destroying the adsorbed organics (i.e., PCB).

In particular, the present systems and cells enable the electrodeposition of any metal, including but not limited to silver, gold, platinum, iridium, rhodium, and the removal of contaminants from body fluids, such as blood. These contaminants could range from organic and inorganic ions to fine particles including viruses.

The present separation processes and systems have several important applications, including:

1. Removal of various ions from waste water without the generation of acid, base, or other similar secondary wastes. This application may be especially important in cases involving radionuclides, where the inventive capacitive deionization process could be used to remove low-level radioactive inorganic materials.

2. Treatment of boiler water in nuclear and fossil power plants. Such treatment is essential for the prevention of pitting, stress corrosion cracking, and scaling of heat transfer surfaces. Such a process may be particularly attractive for nuclear powered ships and submarines where electrical power is readily available and where there are space limitations, thereby restricting the inventory of chemicals required for regeneration of ion exchange resins.

3. Production of high-purity water for semiconductor processing. In addition to removing conductivity without the addition of other chemical impurities, the system is capable of removing small, suspended solids by electrophoresis. Furthermore, the organic impurities chemisorb to the carbon.

4. Electrically-driven water softener for homes. The CDI system would soften home drinking water without the introduction of sodium chloride, and does not require salt additions for regeneration.

5. Removal of salt from water for agricultural irrigation.

6. Desalination of sea water.

By using the CDI separation systems of the present invention, it is now possible to remove organic and inorganic contaminants and impurities from liquid streams by the following physiochemical processes: the reversible electrostatic removal of organic or inorganic ions from water or any other dielectric solvent; the reversible or irreversible removal of any organic or inorganic impurity by any other adsorption process, including but not limited to underpotential metal deposition, chemisorption, and physisorption; the removal of any organic or inorganic impurity by electrodeposition, which could involve either electrochemical reduction or electrochemical oxidation; and the electrophoretic deposition and trappings of small suspended solids, including but not limited to colloids, at the surface of the electrodes. Induced electric dipoles will be forced to the electrode surfaces by the imposed electric field.

More specific applications for the CDI system and process include any application where the capacitive deionizer is used to assist a gas scrubbing column; for example, if $CO^2$ were removed from a gas stream into an aqueous stream, it would convert into $HCO_3^-$ and $CO_3^{2-}$. These ions could be removed from the scrubbing solution by capacitive deionization. Such applications include any large scale parallel use of the capacitive deionizer to assist in load leveling applications since it is recognized that the present invention can simultaneously serve as an energy storage device. Other applications include analytical instruments that combine the principles of capacitive deionization and ion chromatography, and chromatographic instruments based upon ion adsorption on carbon aerogel electrodes, either monolithic or powder beds.

The chromatographs of the present invention have various applications, including: 1. Separation and identification of amino acids, peptides, proteins, and related compounds. 2. Separation of carbohydrates and carbohydrate derivatives. 3. Analysis of various organic acids such as aliphatic and aromatic acids. 4. Separation of aliphatic, heterocyclic and aromatic amines. 5. Separation of nuclide acid components. 6. Separation of nucleosides, nucleotides and bases, such as purine and pyrimidine bases, and mono-, di-, and triphosphate nucleotides. 7. Analysis of alkali and alkaline earth metals in the complex and uncomplex forms. 8. Separation of some rare earth elements. 9. Separation of halides, such as chloride, bromide and iodide. 10. Separation of phosphorous oxyanions, such as complex polyphosphate mixtures, and mixtures containing lower phosphorus anions, thiophosphates, imido-phosphates. 11. Separation of AIC components from hemoglobin in blood. See U.S. Pat. No. 5,294,336 to Mizuno et al. 12. Separation and isolation of human plasma procoaguolant protein factor VIII from biological factors. See U.S. Pat. No. 4,675,385 to Herring. 13. Analysis of Hemoglobins. See U.S. Pat. No. 5,358,639 to Yasuda et al. 14. Isolation of various constituents in blood, including but not limited to the FIV virus.

The intensifier can be used for the analysis of various fluids, including blood and other body fluids, and aqueous solutions of organic and inorganic salts, e.g. to prove compliance with environmental laws, and for the control of plating baths used in the manufacture of printed circuit boards.

EXAMPLE 1

Figure 1:
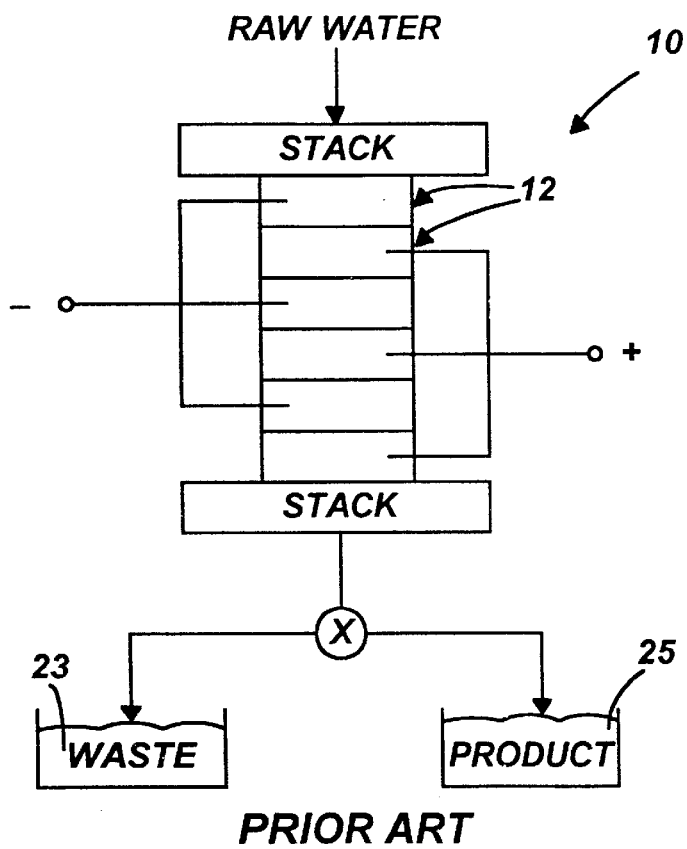
FIG. 1 is a diagrammatic view of a prior art desalination system.
Figure 2:
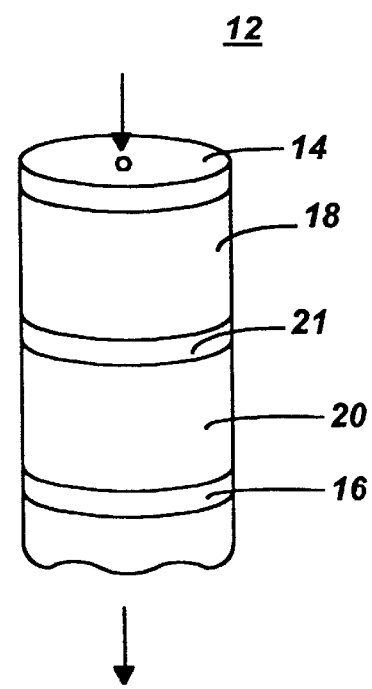
FIG. 2 is an enlarged schematic, isometric, elevational view of a cell used in the model desalination system of FIG. 1.

Comparative deionization-regeneration runs are conducted to illustrate a stopped flow technique during regeneration to achieve equivalent electrode regeneration capacity while decreasing the total volume of waste produced as much as 20% or more. An electrochemical deionization-regeneration cell of the invention similar to that of battery 30 (FIG. 1) is employed, except that each battery contains 150 pairs of electrodes, each containing 10-cm wide by 20-cm long by 0.0127-cm thick carbon aerogel sheet, and can hold 5.5 liters (L) of fluid volume (hold-up volume).

The experimental runs involve treatment (deionization) of an aqueous solution obtained from a contaminated well from Alameda County Farwell well as the raw fluid stream into the battery. Either the raw fluid stream, deionized water, or a mixture thereof, is used as the regenerant solution (i.e., the solution used to regenerate the battery that is fully or partially loaded with ions after the deionization step, i.e., purification step). The conductivity of the raw fluid stream is approximately 2500–2700 micromhos/cm. and the deionized (i.e., newly purified) water product has a conductivity targeted at approximately 500 (or less) micromhos/cm. In the runs, a conversion factor of 1.7 micromhos/cm per 1 mg of total dissolved solids (TDS) is applied. (Such a conversion factor is typical for a solution containing NaCl as the dissolved solid species.)

In a reference run, during the deionization step, the contaminated solution of 2700 micromhos/cm (raw fluid stream) is flown or passed through a clean battery which has been pre-filled with deionized water and precharged at +1.2 V. After passing the 5.5 L of deionized water associated with the initial hold-up volume, 3 L of newly purified product is collected before the outlet conductivity target is reached, i.e., above approximately 500 micromhos/cm. The deionization step is considered complete at this point and regeneration is initiated.

In the reference regeneration run, the battery is then shorted at 0.0 V and the raw fluid feed stream remaining in the battery is used as the initial regenerant solution. Additional volumes of the raw fluid stream are continuously passed through the battery and collected as waste. After between 4–8 hours and approximately 40 L of waste solution collected, the battery is completely regenerated and ready for the next deionization step. In the second deionization-regeneration cycle, another 3 L of newly purified product is collected. This indicates that the regeneration in the previous cycle is complete. Thus, each deionization-regeneration cycle produces about 3 L of newly purified product and generates approximately 40 L of waste solution.

In the regeneration method of the invention, after the 3 L of newly purified product is recovered, the flow to the partially saturated battery is stopped and the battery is discharged to 0.0V. The raw fluid stream remaining in the battery is used as the regenerant solution. During regeneration, the battery is initially charged at reverse potential for 5 minutes at −1.2V to accelerate the ion removal from the electrodes. After one hour (an additional 55 minutes at 0.0V), the regenerant solution in the battery is rapidly replaced as waste with another volume (i.e., 5.5 liters) of raw fluid stream (i.e., regenerant solution) necessary to replace it in the battery. The flow is stopped again for another 1 hour with the initial 5 minute reverse polarity. The waste solution is again replaced with another volume of regenerant solution and soaked for 1 hour with the initial 5 minute reverse polarity at the onset of the 1 hour soak. Thus, a total of three stopped flow, 1-hour regeneration cycles (5 minutes at −1.2V and 55 minutes at 0.0V) utilizing enough regenerant volume to fill the battery, i.e., 5.5 L, produces a total of 16.5 L of collected waste solution and the battery is completely regenerated and ready for the next deionizationregeneration cycle.

In the same manner as in the initial deionization step, a second deionization step after the initial regeneration step of the invention yields another approximately 3 L of collected newly purified product with a conductivity below approximately 500 micromhos/cm. Thus, each deionization-regeneration cycle of the method of the invention produces approximately 3 L of purified product while generating only 16.5 L of waste solution.

Such results indicate that comparable regeneration capacity of the stopped flow method of the invention can be achieved with a production of less than 50% of the waste solution required by that from the continuous regeneration method whereby the regenerant solution is continuously passed through the shorted battery for the duration of the regeneration step. Accordingly, a substantial reduction in the volume of waste fluid is accomplished by utilizing a stopped flow regeneration method.

EXAMPLE 2

Comparative runs are conducted to demonstrate the use of an oxidizing agent, $H_2O_2$, for restoring the electrosorption capacity of a capacitive deionization battery of cells that has been degraded due to organic biofouling from exposure to contaminated ground water during processing. The battery of 150 cells employed in Example 1 is employed in desalination and its electrodes regenerated. The electrodes of this battery have been exposed to aged contaminated ground water that has resulted in a reduction of the salt removal capacity of the battery compared to a battery having electrodes which have not been exposed to such organic contamination.

Similar to Example 1, the present runs involve inletting the battery with the raw fluid stream obtained from a contaminated well from Alameda County Farwell well. Again, either the raw fluid stream solution, deionized water, or a mixture thereof, is employed as the regenerant solution. The conductivity of the solution is about 2500–2700 micromhos/cm. and the newly purified water product conductivity is approximately 500 (or less) micromhos/cm. (The conversion factor of 1.7 micromhos/cm per 1 mg of total dissolved solids (TDS) is used.)

In the reference process, during the deionization step, the contaminated solution having a conductivity of 2700 micromhos/cm is flown or passed through a cleaned battery which has been initially filled with deionized water and precharged at +1.2 V. The battery had been previously exposed to contaminated solution that had been aged for several months, been under repeated use with the raw fluid stream in several runs, and its performance had degraded significantly. For example, when a solution having a conductivity of 1500 micromhos/cm is inleted continuously through the battery, only a total of 2.5 L of newly purified product is collected before the outlet conductivity reaches 686 micromhos/cm. Previous regeneration runs to regenerate the degraded battery have not increased the capacity of the electrodes of the battery.

The regeneration method of the invention employs a regeneration solution containing an oxidizing agent, in this case, 3% by volume of hydrogen peroxide, dissolved in water. When the electrodes of the battery are saturated with ions, the battery is then regenerated by discharge at the applied voltage of 0.0 V. During the regeneration period, the oxidizing solution is inleted into the battery to displace the volume of the battery (i.e., 5.5 liters). Flow is then stopped and the electrosorption media (aerogel) on the electrodes is soaked in the oxidizing solution for four hours. The time normally depends on the level of degradation and frequency of chemical-enhanced treatment. During this soak or stopped period, the outlet valve is left partially open to allow gaseous compounds evolved from the oxidation of the adsorbed chemical (organic) species on the surface of the aerogel electrodes to escape. A small amount of the oxidizing agent is pumped into the battery to replace any solution loss at the outlet. The time of the oxidizing treatment is similar to the prior purification cycle—or shorter if the electrodes are not saturated with ions. At the conclusion of the oxidizing treatment under static flow conditions, the regenerant/waste solution is removed from the battery using a minimal amount of rinsing clean water, e.g., deionized water. Feed solutions, such as contaminated ground water, can also be used as the rinsing water. After the amount of peroxide-containing liquid is completely replaced with the rinsing solution, the flow is again stopped and the battery soaked under static conditions (at 0.0 V) for an additional 1 hour. The rinsed solution is again displaced with another battery volume of rinsing deionized water and soaked at static conditions for another 30 minutes.

The purification step is resumed for the battery of rejuvenated ($H_2O_2$-treated) electrode material. The contaminated fluid inlet stream (at 2700 micromhos/cm) is again passed between charged electrodes at 1.2V. A total of 2 L of newly collected purified product fluid having a conductivity below 700 micromhos/cm is collected. Compared to the capacity before the treatment, this represents a 47% increase in electrosorption capacity as a result of the oxidizing treatment. It is expected that a longer treatment and/or higher $H_2O_2$ concentration can further increase the capacity of such a degraded battery and restore its total salt removal ability to the original capacity level.

The foregoing description of the embodiments of the present invention has been presented for purposes of illustration and description. It is not intended to be exhaustive or to limit the invention to the precise forms described.

What is claimed is:

1. An electrochemical method for deionizing a fluid comprising ions and regenerating electrodes employed in said method, said method comprising:

(1) flowing said fluid through at least one open channel defined between at least three pair of intermediate electrodes of a battery of electrochemical cells to deionize said fluid to produce a deionized fluid, said open channel having no dimension open to the exterior of said battery;

(2) slowing or stopping the flow of said fluid;

(3) contacting said electrodes with a regenerant fluid and regenerating said electrodes of said battery to produce a waste fluid comprising said ions; and (4) flowing more of said fluid through said battery after step (3) to deionize more of said fluid.

2. The method of claim 1 wherein said fluid is passed through said cells of said battery in a serpentine path and said regenerating includes electrically discharging the electrodes to release accumulated ions from said electrodes.

3. The method of claim 2 wherein said electrodes comprise a carbon aerogel composite.

4. The method of claim 2 wherein said regenerating of said electrodes in step (3) is conducted by shorting said cells of said battery or reversing the polarity of said cells of said battery from that of a polarity applied to said cells in step (1).

5. The method of claim 4 wherein said regenerant fluid is selected from the group consisting of an oxidizing agent, chelating agent, organic acid, and surfactant, and is contacted with said electrodes in step (3).

6. The method of claim 2 further comprising step (5), stopping or slowing the deionization of more of said fluid flowing through said battery during step (4), to regenerate said electrodes of said battery.

7. The method of claim 1 wherein said cells comprise a plurality of double-sided intermediate electrodes and said regenerant comprises an oxidizing agent selected from the group consisting of ozone, hydrogen peroxide, Fenton's reagent, silver (II), cobalt (III), iron (III), hypochlorite ($ClO^-$), peroxymonosulfate and peroxydisulfate ($S_2O_8^{-2}$).

8. The method of claim 1 wherein said flow is stopped for at least 5 minutes in step (3) and said electrodes are soaked in said regenerant fluid.

9. The method of claim 1 wherein said regenerant fluid comprising a concentration of ions which is the same or less than that contained in said fluid is passed through said battery in step (3).

10. The method of claim 1 wherein said regenerant fluid comprising a concentration of ions which is the same or greater than that in said fluid is passed through said battery in step (3) at a rate at least as fast as a flow rate of said fluid through said battery in step (1), to regenerate said electrodes.

11. The method of claim 1 wherein said regenerant fluid is passed through said battery subsequent to step (2) in step (3) at a flow rate which is greater than that of said fluid passed through said battery in step (1).

12. The method of claim 1 wherein said regenerant fluid is selected from the group consisting of deionized water, recycled deionized fluid obtained from step (1), and recycled portions of said waste fluid obtained from step (3).

13. The method of claim 1 wherein said fluid is passed through said cells of said battery in a serpentine path.

14. The method of claim 13 wherein said electrodes comprise a carbon aerogel composite.

15. An electrochemical method for deionizing a fluid comprising ions and regenerating electrodes employed in said method, said method comprising:
(1) flowing said fluid through an open channel defined between at least three pair of intermediate electrodes of a battery of electrochemical cells to deionize said fluid, said open channel having no dimension open to the exterior of said battery;
(2) interrupting the flow of said fluid;
(3) contacting said electrodes with a regenerant fluid comprising an oxidizing agent to regenerate said electrodes of said battery; and
(4) flowing more of said fluid through said battery after step (3) to deionize more of said fluid.

16. The method of claim 15 wherein said fluid is passed through said cells of said battery in a serpentine path and said electrodes are electrically regenerated in step (3).

17. The method of claim 16 wherein said cells comprise a plurality of double-sided intermediate electrodes and said flow is stopped for at least 15 minutes in step (2) and said electrodes are soaked in said regenerant fluid in step (3).

18. The method of claim 15 wherein in step (3) includes electrically regenerating said electrodes by shorting said cells of said battery or reversing the polarity of said cells of said battery from a polarity applied to said cells in step (1).

19. The method of claim 15 wherein said electrodes comprise an carbon aerogel composite.

20. The method of claim 15 wherein said regenerant comprises an oxidizing agent selected from the group consisting of ozone, hydrogen peroxide, Fenton's reagent, silver (II), cobalt (III), iron (III), hypochlorite ($ClO^-$), peroxymonosulfate and peroxydisulfate ($S_2O_8^{-2}$).

21. An electrochemical method for deionizing a fluid comprising ions and regenerating electrodes employed in said method, said method comprising:
(1) flowing said fluid through at least one open channel defined between at least three pair of intermediate electrodes of a battery of electrochemical cells to deionize said fluid at a given applied polarity above about 1.2 V to about 1.8V across said open channels, said open channels having no dimension open to the exterior of said battery and said electrodes comprising a carbon aerogel composite;
(2) slowing or stopping the flow of said fluid for a period of at least 5 minutes;
(3) contacting said electrodes with a regenerant fluid and regenerating said electrodes of said battery at a shorted or reversed polarity to produce a waste fluid comprising said ions;
(4) flowing more of said fluid through said battery after step (3) to deionize more of said fluid; and
(5) interrupting said flow of more of said fluid to electrically regenerate said electrodes in the presence of a second regenerant fluid comprising (a) recycled portions of said waste fluid, (b) inleted or recycled portions of said fluid and/or (c) a fluid comprising a lower concentration of said ions than contained in said waste fluid.

22. The method of claim 21 wherein said waste fluid is fast flushed from said battery.

23. A capacitive deionization-regeneration system adapted for operating a deionization cycle and a regeneration cycle, comprising in combination:
(1) a battery of at least four electrochemical cells, each cell comprising at least one pair of adjacent electrodes including an electrosorptive medium having a high specific surface area and sorption capacity, formed on one or more surfaces of said electrodes;
each pair of said adjacent electrodes including at least one aperture; and
each pair of said adjacent electrodes forming an open channel, said open channel adapted to fluidly communicate with a subsequent open channel via said aperture to allow a fluid to flow across said electrosorptive medium and through the battery in a serpentine path,
(2) an electrical circuit for controlling the operation of said battery of cells, said electrical circuit adapted for shorting or switching the polarity of each pair of said electrodes during said regeneration cycle of said electrodes; and
(3) a fluid circuit for regulating the flow of a fluid through said battery under the control of said electrical circuit, in order to slow or stop a fluid flow through said cells for predetermined time intervals during said regeneration cycle, said fluid circuit comprises an outlet adapted for deionized fluid obtained from a deionization cycle operable at a given polarity, and a second outlet adapted for regenerated waste fluid obtained from said regeneration cycle operable at a shorted or reversed polarity relative to said given polarity and at a slower flow rate than the one used during said deionization cycle.

24. The system of claim 23 wherein said electrosorptive medium of said electrodes comprise a carbon aerogel composite.

25. The system of claim 23 wherein said electrosorptive medium is composed essentially of any, or a combination of: carbon aerogel composite; a packed volume of particulate carbon, carbon aerogel, metal, or Buckminster fullerene; a carbide or a composite of carbides that are stable at high temperatures, chemically resistant, and highly conductive with a resistivity ranging between about 10 $\mu$ohm-cm and 2000 $\mu$ohm-cm, selected from a group consisting essentially of TiC, ZrC, VC, NbC, TaC, UC, MoC, WC, $Mo_2C$, $Cr_3C_2$, or $Ta_2C$; a packed volume of porous titanium, platinum or other metal; a metal sponge, or metallic foam; reticulated vitreous carbon (RVC) impregnated in resorcinal/formaldehyde carbon aerogel; or a porous, conductive screen including an array of holes that have been photolithographically formed to optimize the volumetric specific surface area of said screen.

26. The system of claim 23 wherein said fluid circuit comprises a recycle conduit from said second outlet for said waste fluid to a fluid inlet to said battery.

27. The system of claim 23 wherein said fluid circuit comprises a recycle conduit from said second outlet for said waste fluid to an inlet to said battery.

28. The system of claim 23 wherein said fluid circuit comprises a recycle conduit from said outlet for said deionized fluid to an inlet to said battery.

29. An electrically regeneratable electrochemical cell for use in a capacitive deionization apparatus, said cell comprising the following corrosion resistant components:

two end plates, one at each end of the cell;

two end electrodes comprising ceramics, one at each end of the cell, adjacent to the end plates;

an insulator layer interposed between one end plate and an adjacent one of said end electrodes;

an insulator layer interposed between the other end plate and the other one of said end electrodes;

two or more intermediate electrodes comprising ceramics, disposed between said two end electrodes;

each end electrode and intermediate electrodes including an electrosorptive medium having a high specific surface area and sorption capacity; and wherein said corrosion resistant components adapted to withstand deleterious effects of oxidative regenerants contacting said end electrodes or said intermediate electrodes.

30. An electrochemical method for deionizing a fluid comprising ions and regenerating electrodes employed in said method, said method comprising:

(1) flowing said fluid through at least one open channel defined between at least three pair of intermediate electrodes of a battery of electrochemical cells to deionize said fluid to produce a deionized fluid, said open channel having no dimension open to the exterior of said battery;

(2) contacting said electrodes with a regenerant fluid added to said fluid and regenerating said electrodes of said battery to produce a waste fluid comprising said ions; and (3) flowing said regenerant fluid through said battery at a faster rate than said flowing of said fluid through said battery in step (1).

* * * * *